United States Patent
Wang et al.

(10) Patent No.: US 11,202,782 B2
(45) Date of Patent: Dec. 21, 2021

(54) TREATMENT CANCERS USING A COMBINATION COMPRISING PARP INHIBITORS

(71) Applicant: BeiGene, Ltd., Grand Cayman (KY)

(72) Inventors: Lai Wang, Beijing (CN); Zhiyu Tang, Beijing (CN); Lusong Luo, Beijing (CN); Min Wei, Beijing (CN); Kang Li, Beijing (CN); Jing Song, Beijing (CN); Tong Zhang, Beijing (CN); Hexiang Wang, Beijing (CN); Bo Ren, Beijing (CN); Changyou Zhou, Princeton, NJ (US)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 16/337,124

(22) PCT Filed: Sep. 27, 2017

(86) PCT No.: PCT/CN2017/103660
§ 371 (c)(1),
(2) Date: Mar. 27, 2019

(87) PCT Pub. No.: WO2018/059437
PCT Pub. Date: Apr. 5, 2018

(65) Prior Publication Data
US 2020/0030339 A1 Jan. 30, 2020

(30) Foreign Application Priority Data
Sep. 27, 2016 (CN) .................. PCT/CN2016/100320

(51) Int. Cl.
| A61K 31/551 | (2006.01) |
| A61K 45/00 | (2006.01) |
| A61P 35/00 | (2006.01) |
| C07D 471/16 | (2006.01) |
| C07D 487/06 | (2006.01) |
| C07D 487/16 | (2006.01) |
| A61K 31/282 | (2006.01) |
| A61K 31/337 | (2006.01) |
| A61K 31/357 | (2006.01) |
| A61K 39/395 | (2006.01) |
| C07K 16/28 | (2006.01) |

(52) U.S. Cl.
CPC .......... *A61K 31/551* (2013.01); *A61K 31/282* (2013.01); *A61K 31/337* (2013.01); *A61K 31/357* (2013.01); *A61K 39/3955* (2013.01); *A61P 35/00* (2018.01); *C07K 16/2818* (2013.01)

(58) Field of Classification Search
CPC ....... A61K 31/551; A61K 45/00; A61P 35/00; C07D 471/16; C07D 487/06; C07D 487/16
See application file for complete search history.

(56) References Cited

U.S. PATENT DOCUMENTS

| 9,260,440 B2 * | 2/2016 | Zhou ................. C07D 487/06 |
| 9,617,273 B2 * | 4/2017 | Zhou ................. C07D 487/06 |
| 10,112,952 B2 * | 10/2018 | Zhou ................. C07D 487/04 |
| 10,457,680 B2 * | 10/2019 | Wang ..................... A61P 35/04 |
| 10,501,467 B2 | 12/2019 | Zhou et al. |
| 10,899,763 B2 | 1/2021 | Wang et al. |
| 2008/0146638 A1 | 6/2008 | Giranda et al. |
| 2015/0175617 A1 | 6/2015 | Zhou et al. |
| 2016/0159811 A1 | 6/2016 | Zhou et al. |
| 2016/0222012 A1 | 8/2016 | Ruan |
| 2017/0305921 A1 | 10/2017 | Zhou et al. |
| 2019/0016731 A1 | 1/2019 | Zhou et al. |
| 2019/0177325 A1 | 6/2019 | Wang et al. |
| 2020/0155567 A1 * | 5/2020 | Wang ..................... A61P 35/00 |
| 2020/0157103 A1 * | 5/2020 | Wang ..................... A61P 35/00 |

FOREIGN PATENT DOCUMENTS

| CN | 103703004 A | 4/2014 |
| CN | 106220635 A | 12/2016 |
| JP | 2002-534523 | 10/2002 |
| WO | WO 2000/042040 | 7/2000 |
| WO | WO 2002/044183 | 6/2002 |
| WO | WO 2004/063198 | 7/2004 |
| WO | WO 2010/017055 | 2/2010 |
| WO | WO 2013/097225 | 7/2013 |

(Continued)

OTHER PUBLICATIONS

Extended European Search Report for European Application No. 11878508.8, dated Sep. 22, 2015, 3 pages.
Extended European Search Report for European Application No. 17183473.2, dated Apr. 4, 2018, 6 pages.
International Preliminary Report on Patentability for International Application No. PCT/CN2011/085148, dated Jul. 1, 2014, 7 pages.
International Search Report and Written Opinion for International Application No. PCT/CN2011/085148, dated Sep. 27, 2012, 12 pages.

(Continued)

*Primary Examiner* — Brenda L Coleman
(74) *Attorney, Agent, or Firm* — Cooley LLP

(57) ABSTRACT

Disclosed herein is a method for the prevention, delay of progression or treatment of cancer in a subject, comprising administering to the subject in need thereof a PARP inhibitor, particularly, (R)-2-fluoro-10a-methyl-7,8,9,10,10a,11-hexahydro-5,6,7a,11-tetraazacyclohepta[def]cyclopenta[a]fluoren-4(5H)-one, a sesqui-hydrate thereof, or a pharmaceutically acceptable salt thereof, in combination with an immune checkpoint inhibitor or a chemotherapeutic agent. Also, disclosed a pharmaceutical combination comprising a PARP inhibitor, particularly, (R)-2-fluoro-10a-methyl-7,8,9,10,10a,11-hexahydro-5,6,7a,11-tetraazacyclohepta[def]cyclopenta[a]fluoren-4(5H)-one, a sesqui-hydrate thereof, or a pharmaceutically acceptable salt thereof, in combination with an immune checkpoint inhibitor, or a chemotherapeutic agent and the use thereof.

29 Claims, 12 Drawing Sheets

Specification includes a Sequence Listing.

(56) References Cited

FOREIGN PATENT DOCUMENTS

| WO | WO 2015/035606 | 3/2015 |
|----|----------------|--------|
| WO | WO 2016/000619 | 1/2016 |
| WO | WO 2017/032289 | 3/2017 |
| WO | WO 2017/075091 | 5/2017 |
| WO | WO 2018/059437 | 4/2018 |
| WO | WO 2018/157794 | 9/2018 |
| WO | WO 2019/015561 | 1/2019 |
| WO | WO 2019/228499 | 12/2019 |

OTHER PUBLICATIONS

Extended European Search Report for European Application No. 16838548.2, dated Dec. 19, 2018, 8 pages.

International Search Report and Written Opinion for International Application No. PCT/CN2016/096200, dated Nov. 11, 2016, 12 pages.

Extended European Search Report for European Application No. 17854887.1, dated May 25, 2020, 9 pages.

International Search Report and Written Opinion for International Application No. PCT/CN2017/103660, dated Jan. 9, 2018, 11 pages.

International Search Report and Written Opinion for International Application No. PCT/CN2018/077433, dated Jun. 5, 2018, 11 pages.

International Search Report and Written Opinion for International Application No. PCT/CN2018/095911, dated Oct. 26, 2018, 9 pages.

Chen, A., "PARP inhibitors: its role in treatment of cancer," Chinese Journal of Cancer, 2011, vol. 30, Issue 7, pp. 463-471.

Higuchi, T. et al., "CTLA-4 Blockade Synergizes Therapeutically with PARP Inhibition in BRCA1-Deficient Ovarian Cancer," Cancer Immunol. Res., Nov. 2015, 3(11):1257-1268 (Author Manuscript).

Tang, Z. et al., "Abstract 1653: BGB-290: A highly potent and specific PARP1/2 inhibitor potentiates anti-tumor activity of chemotherapeutics in patient biopsy derived SCLC models," In: Proceedings of the 106th Annual Meeting of the American Association of Cancer Research; Apr. 18-22, 2015; Philadelphia, PA: AACR; Cancer Res. 2015;75(15 Suppl.);Abstract nr 1653, 5 pages.

U.S. National Library of Medicine, "History of Changes for Study: NCT02660034. The Safety, Pharmacokinetics and Antitumor Activity of the BGB-A317 in Combination With the BGB-290 in Subject With Tumors", ClinicalTrials.gov archive [Online], Aug. 27, 2016, Retrieved from the Internet: <URL: https://clinicaltrials.gov/ct2/history/NCT02660034?V_3=View#StudyPageTop>, Retrieved on Jun. 5, 2020, 4 pages.

Morissette, S. L., "High-throughput crystallization: polymorphs, salts, co-crystals and solvates of pharmaceutical solids," Advanced Drug Delivery Reviews, vol. 56, No. 3, Feb. 2004, pp. 275-300.

Fujiwara, M. et al., "First-principles and direct design approaches for the control of pharmaceutical crystallization," Journal of Process Control, vol. 15, No. 5, Aug. 2005, pp. 493-504.

Variankaval, N. et al., "From form to function: Crystallization of active pharmaceutical ingredients," AiChE Journal, vol. 54, No. 7, Jul. 2008, pp. 1682-1688.

Caira, M. R., "Crystalline polymorphism of organic compounds," Topics in Current Chemistry, vol. 198, 1998, pp. 163-208.

Underhill, C. et al., "A review of PARP inhibitors: from bench to bedside," Annals of Oncology, Advance Access published Jul. 19, 2010, doi:10.1093/annonc/mdq322, Retrieved from the Internet: <URL: http://annonc.oxfordjournals.org/>. Retrieved from the Internet on Jun. 14, 2016, 12 pages.

STN International, RN: 1858211-28-5, STN Registry, Feb. 2, 2016, 2 pages.

Extended European Search Report for European Application No. 18835555.6, dated Mar. 4, 2021, 11 pages.

International Search Report and Written Opinion for International Application No. PCT/CN2019/089523, dated Sep. 5, 2019, 9 pages.

Bang, Y-J. et al., "Randomized, double-blind phase II trial with prospective classification by ATM protein level to evaluate the efficacy and tolerability of olaparib plus paclitaxel in patients with recurrent or metastatic gastric cancer," Journal of Clinical Oncology, vol. 33, No. 33, Nov. 2015, pp. 3858-3865.

Tang, Z. et al., "Abstract 1651: BGB-290, a novel PARP inhibitor with unique brain penetration ability, demonstrated strong synergism with temozolomide in subcutaneous and intracranial xenograft models," Cancer Research, Aug. 2015, AACR 106th Annual Meeting 2015; Apr. 18-22, 2015, Philadelphia, PA, Retrieved from the Internet: <URL: https://cancerres.aacrjournals.org/content/75/15_Supplement/1651 [retrieved on May 6, 2020], 4 pages.

Gupta, S. K. et al., "Abstract 3505: Inhibition of PARP activity by BGB-290 potentiates efficacy of temozolomide in patient derived xenografts of glioblastoma multiforme," Cancer Research, Aug. 2015, AACR 106th Annual Meeting 2015; Apr. 18-22, 2015, Philadelphia, PA, Retrieved from the Internet: <URL:https://cancerres.aacrjournals.org/content/75/15 Supplement/3505.short>, [retrieved-on May 5, 2020], 4 pages.

Lok, B. H. et al., "PARP Inhibitor Activity Correlates with SLFN11 Expression and Demonstrates Synergy with Temozolomide in Small Cell Lung Cancer," Clinical Cancer Research, vol. 23, No. 2, Jul. 2016, pp. 523-535.

Chabot, P. et al., "Veliparib in combination with whole-brain radiation therapy for patients with brain metastases from non-small cell lung cancer: results of a randomized, global, placebo-controlled study," Journal of Neurooncology, vol. 131, No. 1, 2017, pp. 105-115.

Parrish, K. E. et al., "Efficacy of PARP Inhibitor Rucaparib in Orthotopic Glioblastoma Xenografts Is Limited by Ineffective Drug Penetration into the Central Nervous System," Molecular Cancer Therapeutics, vol. 14, No. 12, Oct. 2015, pp. 2735-2743.

* cited by examiner

TREATMENT CANCERS USING A COMBINATION COMPRISING PARP INHIBITORS

CROSS-REFERENCE TO RELATED APPLICATIONS

This application is U.S. national stage application to International Patent Application No. PCT/CN2017/103660, filed Sep. 27, 2017, which claims the benefit of priority to International Patent Application No. PCT/CN2016/100320 filed on Sep. 27, 2016, the entire contents of each of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BEIG_019_01US_SeqList.txt, date recorded: Mar. 26, 2019, file size 79 kilobytes).

FIELD OF THE INVENTION

Disclosed herein is a method for the prevention, delay of progression or treatment of cancer in a subject, comprising administering to the subject in need thereof a PARP inhibitor (in particularly (R)-2-fluoro-10a-methyl-7,8,9,10,10a,11-hexahydro-5,6,7a,11-tetraazacyclohepta[def]cyclopenta[a]fluoren-4(5H)-one or a pharmaceutically acceptable salt thereof, (R)-2-fluoro-10a-methyl-7,8,9,10,10a,11-hexahydro-5,6,7a,11-tetraazacyclohepta[def]cyclopenta[a]fluoren-4(5H)-one sesqui-hydrate) in combination with an immune checkpoint inhibitor or a chemotherapeutic agent. Disclosed herein is also a pharmaceutical combination comprising a PARP inhibitor (in particularly (R)-2-fluoro-10a-methyl-7,8,9,10,10a,11-hexahydro-5,6,7a,11-tetraazacyclohepta[def]cyclopenta[a]fluoren-4(5H)-one or a pharmaceutically acceptable salt thereof, (R)-2-fluoro-10a-methyl-7,8,9,10,10a,11-hexahydro-5,6,7a,11-tetraazacyclohepta[def]cyclopenta[a]fluoren-4(5H)-one sesqui-hydrate) in combination with an immune checkpoint inhibitor, or a chemotherapeutic agent and the use thereof.

BACKGROUND OF THE INVENTION

One of the hallmarks and driving forces of cancer is genetic instability [Hanahan D and Weinberg R A, *Hallmarks of cancer: the next generation. Cell,* 2011. 144(5): p. 646-74.]. Specifically in familial cancers, mutations in the breast cancer susceptibility BRCA1 and BRCA2 tumor suppressor genes, key players in homologous recombination (HR), have been associated with an increased risk of developing breast or ovarian cancer [Li X and Heyer W D, *Homologous recombination in DNA repair and DNA damage tolerance. Cell Res,* 2008. 18(1): p. 99-113.]. It is in this patient population that inhibitors of poly (ADP-ribose) polymerase (PARP) have gained recent attention. PARP family members PARP1 and PARP2 play important roles in DNA replication, transcriptional regulation, and DNA damage repair [Rouleau M, Patel A, Hendzel M J, et al., *PARP inhibition: PARP1 and beyond. Nat Rev Cancer,* 2010. 10(4): p. 293-301.]. In 2005, two breakthrough Nature papers showed that PARP inhibitors given alone could kill cancer cells with pre-existing DNA repair defects, specifically mutations in BRCA1/2 genes [Bryant H E, Schultz N, Thomas H D, et al., *Specific killing of BRCA2-deficient tumors with inhibitors of poly(ADP-ribose) polymerase. Nature,* 2005. 434(7035): p. 913-7; Farmer H, McCabe N, Lord C J, et al., *Targeting the DNA repair defect in BRCA mutant cells as a therapeutic strategy. Nature,* 2005. 434 (7035): p. 917-21].

PARP inhibition and mutant BRCA were synthetically lethal in preclinical models, suggesting an elegant, targeted and minimally toxic way to treat patients.

WO2013/097225A1 disclosed a series of PARP inhibitor having the following general Formula (I) or a stereoisomer thereof, or a pharmaceutically acceptable salt thereof,

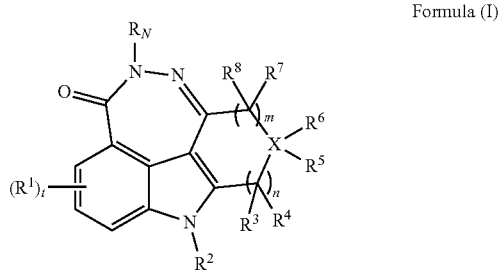

Formula (I)

In particularly, (R)-2-fluoro-10a-methyl-7,8,9,10,10a,11-hexahydro-5,6,7a,11-tetraazacyclohepta[def]cyclopenta[a]fluoren-4(5H)-one (hereinafter Compound A), disclosed in WO2013/097225A1, has highly selective and potent PARP1/2 inhibitory activities.

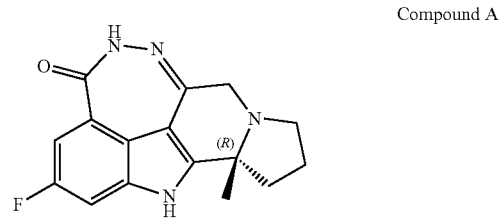

Compound A

PCT application PCT/CN2016/096200 also discloses crystalline forms of Compound A, particularly, (R)-2-fluoro-10a-methyl-7,8,9,10,10a,11-hexahydro-5,6,7a,11-tetraazacyclohepta[def]cyclopenta[a]fluoren-4(5H)-one sesqui-hydrate (hereinafter Compound B).

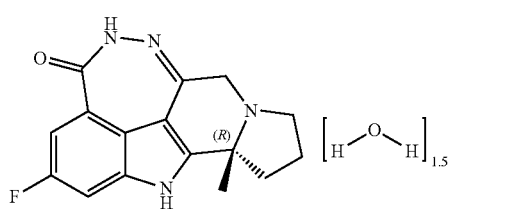

Compound B

The inventors of the present application have found that the combination treatment of a PARP inhibitor (in particular, the above-mentioned Compound A or Compound B) with an immunotherapy agent (for example, an immune checkpoint inhibitor) or a chemotherapeutic agent demonstrates better anti-tumor activity than the monotherapy of each of the above active pharmaceutical agent alone, without severe toxicity.

SUMMARY OF THE INVENTION

In a first aspect, disclosed herein is a method for the prevention, delay of progression or treatment of cancer in a subject, comprising administering to the subject in need thereof a therapeutically effective amount of a PARP inhibitor of Formula (I) or a stereoisomer thereof, a pharmaceutically acceptable salt thereof or a solvate thereof, in combination with a therapeutically effective amount of an immune checkpoint inhibitor or a chemotherapeutic agent.

In a second aspect, disclosed herein is a pharmaceutical combination for use in the prevention, delay of progression or treatment of cancer, comprising a PARP inhibitor of Formula (I) or a stereoisomer thereof, a pharmaceutically acceptable salt thereof or a solvate thereof, in combination with a therapeutically effective amount of an immune checkpoint inhibitor or a chemotherapeutic agent.

In a third aspect, disclosed herein is a PARP inhibitor of Formula (I) or a stereoisomer thereof, a pharmaceutically acceptable salt thereof or a solvate thereof, for use in the prevention, delay of progression or treatment of cancer in combination with a therapeutically effective amount of an immune checkpoint inhibitor or a chemotherapeutic agent. In one embodiment of this aspect, disclosed herein is an immune checkpoint inhibitor or a chemotherapeutic agent for use in the prevention, delay of progression or treatment of cancer in combination with a PARP inhibitor of Formula (I) or a stereoisomer thereof, a pharmaceutically acceptable salts thereof or a solvate thereof.

In a fourth aspect, disclosed herein is a use of a pharmaceutical combination in the manufacture of a medicament for use in the prevention, delay of progression or treatment of cancer, said pharmaceutical combination comprising a PARP inhibitor of Formula (I) or a stereoisomer thereof, a pharmaceutically acceptable salt thereof, or a solvate thereof, and an immune checkpoint inhibitor or a chemotherapeutic agent.

In a fifth aspect, disclosed herein is an article of manufacture, or "kit" comprising a first container, a second container and a package insert, wherein the first container comprises at least one dose of a medicament comprising a PARP inhibitor of Formula (I) or a stereoisomer thereof, a pharmaceutically acceptable salt thereof, or a solvate thereof; the second container comprises at least one dose of a medicament comprising an immune checkpoint inhibitor or a chemotherapeutic agent, and the package insert comprises instructions for treating cancer a subject using the medicaments.

In a sixth aspect, disclosed herein is a method for the prevention, delay of progression or treatment of cancer in a subject, comprising:
(i) in the treatment cycle, administering to the subject in need thereof a chemotherapeutic agent together with a first amount of the PARP inhibitor of Formula (I); and
(ii) in the maintenance phase, administering to the subject which has been treated in the above treatment cycle a second amount of the PARP inhibitor of Formula (I).

In some embodiments, the PARP inhibitor is Compound A. In other embodiments, the PARP inhibitor is Compound B.

In some embodiments, the PARP inhibitor is administered continuously or intermittently during the treatment cycle.

In some embodiments, the method comprises 1 to 3 treatment cycles, and each treatment cycle comprises 1 to 4 weeks.

In some embodiments, the chemotherapeutic agent is selected from paclitaxel, or etopside plus carboplatin (E/C).

In some embodiments, the chemotherapeutic agent is administered at a standard dosing regimen. In particular, the standard dosing schedule for C/E includes cisplatin 75 mg/m$^2$ on day 1, etoposide 100 mg/m$^2$ on day 1, 2, 3 of every 21 days, 21 days per Cycle; or carboplatin AUC 5-6 on day 1, etoposide 100 mg/m$^2$ on day 1, 2, 3 of every 2ldays, 21 days per Cycle; and the standard dosing schedule for paclitaxel: 80 mg/m$^2$ iv on day 1, 8, 15 of every 28 days, 28 days per Cycle.

In some embodiments, the first amount of the PARP inhibitor in the treatment cycle is different from the second amount of the PARP inhibitor in the maintenance phase.

In some embodiments, the first amount of the PARP inhibitor in the treatment cycle is lower from the second amount of the PARP inhibitor in the maintenance phase.

In some embodiments, the second amount of the PARP inhibitor in the maintenance phase is 1-120 mg (in terms of the parent compound) with the administration frequency of once to twice a day; preferably, the administered dosage of the PARP inhibitor is 1-80 mg (in terms of the parent compound), and the administration frequency is twice a day (BID). In other embodiments, the second amount of the PARP inhibitor in the maintenance phase is about 120-240 mg once a day (QD) and the first amount of the PARP inhibitor in the treatment cycle is about 60-120 mg once a day (QD).

The method and pharmaceutical combination disclosed herein, as a combination therapy, produce more efficacious anti-tumor response than either single agent alone. In particular, the combination of the anti-PD-1 antibody (Mab-1) and Compound B was confirmed to exhibit synergistic effect. So was the combination of Compound A or Compound B with paclitaxel or etoposide plus carboplatin (E/C).

In an embodiment of each of the above six aspects, the chemotherapeutic agent is selected from paclitaxel, or etopside plus carboplatin (E/C). In an embodiment of each of the above six aspects, the immune checkpoint inhibitor is an antibody. In an embodiment of each of the above six aspects, the immune checkpoint inhibitor is a monoclonal antibody. In an embodiments of each of the above six aspects, the immune checkpoint inhibitor is an inhibitor of PD-1. In an embodiment of each of the above six aspects, the cancer is selected from colorectal cancer, gastric cancer, lung cancer, small cell lung cancer, bladder cancer, breast cancer, ovarian cancer, fallopian tube carcinoma, cervical cancer, peritoneal carcinoma, prostate cancer, castration-resistant prostate, bile duct cancer, gastric/gastro-esophageal junction cancer, urothelial cancer, pancreatic cancer, peripheral nerve sheath cancer, uterine cancer, melanoma or lymphoma. In an embodiment of each of the above six aspects, the PARP inhibitor is (R)-2-fluoro-10a-methyl-7,8,9,10,10a,11-hexahydro-5,6,7a,11-tetraazacyclohepta[def]cyclopenta[a]fluoren-4(5H)-one (Compound A), or a pharmaceutically acceptable salt thereof. In an embodiment of each of the above six aspects, the PARP inhibitor is (R)-2-fluoro-10a-methyl-7,8,9,10,10a,11-hexahydro-5,6,7a,11-tetraazacyclohepta[def]cyclopenta[a]fluoren-4(5H)-one sesqui-hydrate (Compound B). In an embodiment of each of the above six aspects, the PARP inhibitor and the immune checkpoint inhibitor, or a chemotherapeutic agent, are administered simultaneously, sequentially or intermittently.

DETAILED DESCRIPTION OF THE INVENTION

Definitions

Figure 1:
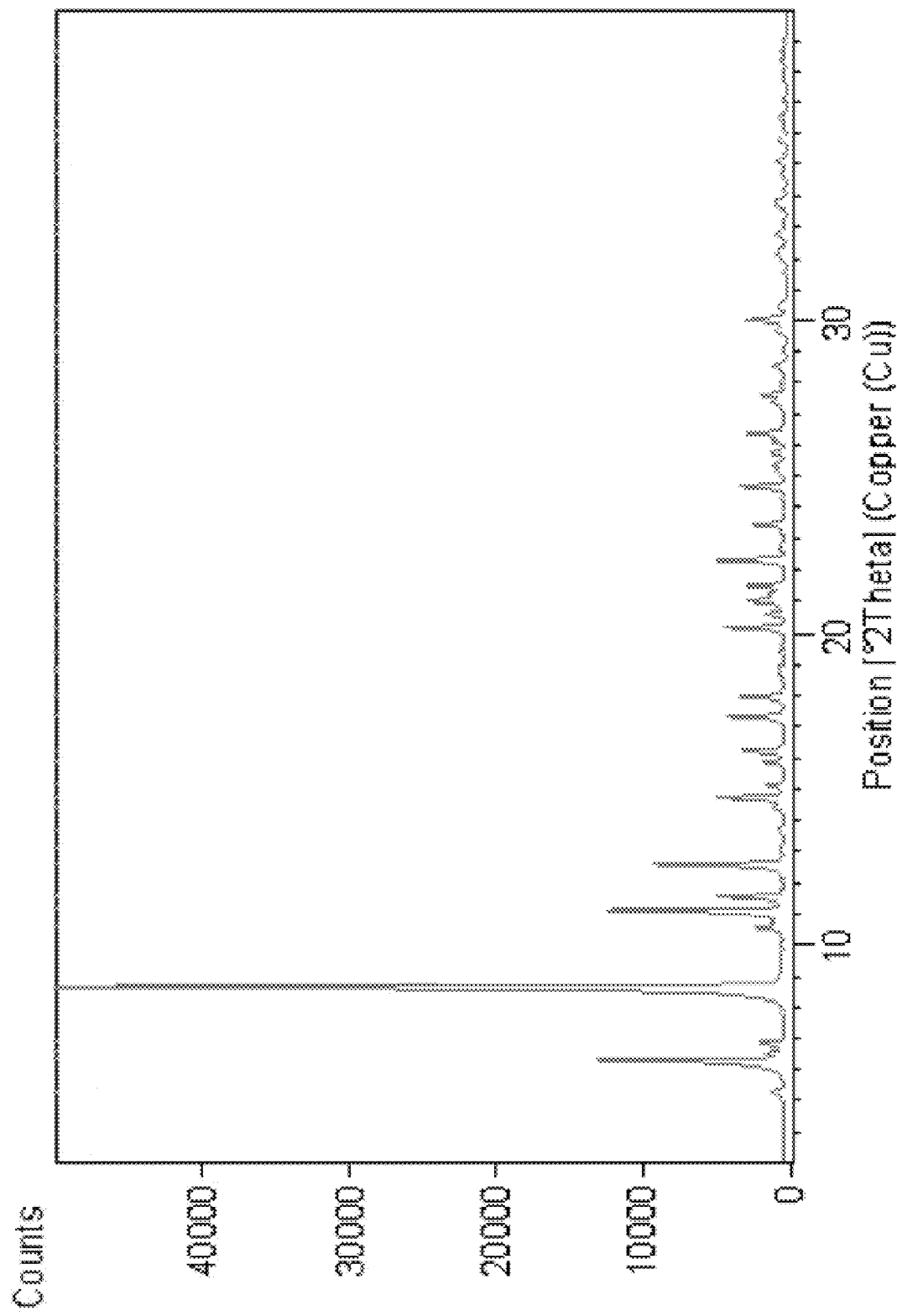
FIG. 1 shows the X-ray diffraction pattern of crystal Compound B.

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

Throughout this specification and the claims which follow, unless the context requires otherwise, the word "comprise", and variations such as "comprises" and "comprising", will be understood to imply the inclusion of an active agent (e.g., a mAb or a Btk inhibitor) or a stated amino acid sequence, but not the exclusion of any other active ingredient or amino acid sequence. When used herein the term "comprising" can be interchangeable with the term "containing" or "including".

The term "alkyl" herein refers to a hydrocarbon group selected from linear and branched saturated hydrocarbon groups comprising from 1 to 18, such as from 1 to 12, further such as from 1 to 6, carbon atoms. Examples of the alkyl group can be selected from methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)2), 2-methyl-2-butyl (—C(CH$_3$)2CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$) and 3,3-dimethyl-2-butyl (—CH(CH$_3$)C(CH$_3$)$_3$ groups.

The term "alkenyl" herein refers to a hydrocarbon group selected from linear and branched hydrocarbon groups comprising at least one C=C double bond and from 2 to 18, such as from 2 to 6, carbon atoms. Examples of the alkenyl group may be selected from ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as from 2 to 6, carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e., partially unsaturated), but is not fully conjugated, and is not aromatic, as aromatic is defined herein.

The term "aryl" herein refers to a group selected from:
  5- and 6-membered carbocyclic aromatic rings, for example, phenyl;

bicyclic ring systems such as 7 to 12 membered bicyclic ring systems wherein at least one ring is carbocyclic and aromatic, selected, for example, from naphthalene and indane; and tricyclic ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals.

Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "arylalkyl" herein refers to an alkyl group as defined above substituted by an aryl group as defined above.

The term "halogen" or "halo" herein refers to F, Cl, Br or I.

The term "heteroaryl" herein refers to a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and /or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e., partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl,1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and /or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and /or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review.*" *J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

"Pharmaceutically acceptable salts" include, but are not limited to salts with inorganic acids, selected, for example, from hydrochlorides, phosphates, diphosphates, hydrobromides, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "pharmaceutically acceptable salts thereof" include salts of at least one compound of Formulas I, II (including II-1, II-2 or II-3) or III, and salts of the stereoisomers of at least one compound of Formulas I, II (including II-1, II-2 or II-3) or III, such as salts of enantiomers, and /or salts of diastereomers.

"Treating", "treat", or "treatment" or "alleviation" refers to administering at least one compound and/or at least one pharmaceutically acceptable salt thereof disclosed herein to a subject in recognized need thereof that has, for example, cancer disease, or has a symptom of, for example, cancer disease, or has a predisposition toward, for example, cancer disease, with the purpose to cure, heal, alleviate, relieve, alter, remedy, ameliorate, improve, or affect, for example, cancer disease, the symptoms of, for example, cancer disease, or the predisposition toward, for example, cancer disease.

The term "effective amount" refers to an amount of at least one compound, stereoisomers thereof, pharmaceutically acceptable salts thereof and solvates thereof, disclosed herein effective to "treat," as defined above, a disease or disorder in a subject. In the case of cancer, the effective amount may cause any of the changes observable or measurable in a subject as described in the definition of "treating", "treat", "treatment" and "alleviation" above. For example, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of PARP. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents.

The term "inhibition" indicates a decrease in the baseline activity of a biological activity or process. "Inhibition of PARP" refers to a decrease in the activity of PARP as a direct or indirect response to the presence of at least one compound and/or at least one pharmaceutically acceptable salt disclosed herein, relative to the activity of PARP in the absence of the at least one compound and/or the at least one pharmaceutically acceptable salt thereof. The decrease in activity is not bound by theory and may be due to the direct interaction of the at least one compound, stereoisomers thereof, and pharmaceutically acceptable salts thereof disclosed herein with PARP, or due to the interaction of the at least one compound and/or at least one pharmaceutically acceptable salt disclosed herein, with one or more other factors that in turn affect PARP activity. For example, the presence of at least one compound, stereoisomers thereof, and pharmaceutically acceptable salts thereof disclosed herein, may decrease PARP activity by directly binding to the PARP, by causing (directly or indirectly) another factor to decrease PARP activity, or by (directly or indirectly) decreasing the amount of PARP present in the cell or organism.

The term "at least one substituent" disclosed herein includes, for example, from 1 to 4, such as from 1 to 3, further as 1 or 2, substituents. For example, "at least one substituent $R^2$" disclosed herein includes from 1 to 4, such as from 1 to 3, further as 1 or 2, substituents selected from the list of $R^{12}$ as described herein.

The terms "administration", "administering" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "antibody" herein is used in the broadest sense and specifically covers antibodies (including full length monoclonal antibodies) and antibody fragments so long as they recognize antigen, such as, a target antigen (e.g., CD20) or an immune checkpoint (e.g., PD-1). An antibody molecule is usually monospecific, but may also be described as idiospecific, heterospecific, or polyspecific. Antibody molecules bind by means of specific binding sites to specific antigenic determinants or epitopes on antigens.

The term "monoclonal antibody" or "mAb" or "Mab" herein means a population of substantially homogeneous antibodies, i.e., the antibody molecules comprised in the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. Monoclonal antibodies (mAbs) may be obtained by methods known to those skilled in the art. See, for example, U.S. Pat. No. 4,376,110. The mAbs disclosed herein may be of any immunoglobulin class including IgG, IgM, IgD, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxyl-terminal portion of the heavy chain may define a constant region primarily responsible for effector function. Typically, human light chains are classified as kappa and lambda light chains. Furthermore, human heavy chains are typically classified as α, δ, ε, γ, or μ, and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (Vl/Vh) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)", which are located between relatively conserved framework regions (FR). The CDRs are usually aligned by the framework regions, enabling binding to a specific epitope. In general, from N-terminal to C-terminal, both light and heavy chain variable domains comprise FR-1 (or FR1), CDR-1 (or CDR1), FR-2 (FR2), CDR-2 (CDR2), FR-3 (or FR3), CDR-3 (CDR3), and FR-4 (or FR4). The assignment of amino acids to each domain is, generally, in accordance with the definitions of Sequences of Proteins of Immunological Interest, Kabat, et al., *National Institutes of Health*, Bethesda, Md. ; 5<m> ed.; *NIH Publ*. No. 91-3242 (1991); Kabat (1978) *Adv. Prot. Chem.* 32: 1-75; Kabat, et al., (1977) *J. Biol. Chem.* 252:6609-6616; Chothia, et al, (1987) *J Mol. Biol.* 196:901-917 or Chothia, et al, (1989) *Nature* 342:878-883.

The term "hypervariable region" means the amino acid residues of an antibody that are responsible for antigen-binding. The hypervariable region comprises amino acid residues from a "complementarity determining region" or "CDR" (i.e., CDR-L1, CDR-L2 and CDR-L3 in the light chain variable domain and CDR-H1, CDR-H2 and CDR-H3 in the heavy chain variable domain). See, Kabat et al. (1991) *Sequences of Proteins of Immunological Interest*, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). The term "framework" or "FR" means those variable domain residues other than the hypervariable region residues defined herein as CDR residues.

Unless otherwise indicated, "antibody fragment" or "antigen-binding fragment" means antigen binding fragments of antibodies, i.e. antibody fragments that retain the ability to bind specifically to the antigen bound by the full-length antibody, e.g. fragments that retain one or more CDR regions. Examples of antigen binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a mature human PD-1 molecule, if it binds to polypeptides comprising that sequence but does not bind to proteins lacking that sequence.

The term "human antibody" herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" mean an antibody that comprises only mouse or rat immunoglobulin protein sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu", "Hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer" or "tumor" herein mean or describe the physiological condition involving abnormal cell growth with the potential to invade or spread to other parts of the body. The "disease" refers to any disease, discomfort, illness, symptoms or indications, and can be substituted with the term "disorder" or "condition".

In some embodiments, the cancer is colorectal cancer, gastric cancer, lung cancer, small cell lung cancer, bladder cancer, breast cancer, ovarian cancer, fallopian tube carcinoma, cervical cancer, peritoneal carcinoma, prostate cancer, castration-resistant prostate, bile duct cancer, gastric/gastro-esophageal junction cancer, urothelial cancer, pancreatic cancer, peripheral nerve sheath cancer, uterine cancer, melanoma or lymphoma.

The term "CDRs" means complementarity determining region(s) in an immunoglobulin variable region, defined using the Kabat numbering system, unless otherwise indicated.

Immune Checkpoint Inhibitors

In some embodiments, the Parp inhibitor is co-administered with an immune checkpoint inhibitor, which is an inhibitor of PD-1, PD-L1, PD-L2, TIM-3, Gal-9, CTLA-4, CD80, CD86, A2AR, B7-H3, B7-H4, BTLA, BTLA, HVEM, IDO1, IDO2, TDO, LAG3, VISTA, KIR, 2B4, CD2, CD27, CD28, CD30, CD40, CD90,CD137, CD226, CD276, DR3, GITR, ICOS, LAIR1, LIGHT, MARCO, PS, OX-40, SLAM TIGHT, CTCNI, or a combination thereof.

"Immune checkpoints (checkpoint proteins)"are molecules in the immune system that either turn up a signal (co-stimulatory molecules) or turn down a signal. And they also regulate T-cell activation or function. Many cancers protect themselves from the immune system by inhibiting the T cell signal. An "immune checkpoint inhibitor", which totally or partially reduces, inhibits, interferes with or modulates one or more checkpoint proteins, has been increasing considered as targets for cancer immunotherapies. Numerous checkpoint proteins are known, such as PD-1 (Programmed Death 1, CD279) with its ligands PD-L1 (also named CD274 or B7-H1) and PD-L2; TIM-3 (T-cell Immunoglobulin domain and Mucin domain 3, also known as HAVCR2) and its ligand Gal-9; CTLA-4 (Cytotoxic T-Lymphocyte-Associated protein 4, CD152) and its ligands CD80 and CD86; and A2AR (Adenosine A2A receptor); B7-H3 (CD276); B7-H4 (VTCN1); BTLA (B and T Lymphocyte Attenuator, CD272) and its ligand HVEM (Herpesvirus Entry Mediator); IDO (Indoleamine 2,3-dioxygenase); LAG3 (Lymphocyte Activation Gene-3); VISTA (V-domain Ig suppressor of T-cell activation); KIR (Killer-cell Immunoglobulin-like Receptor). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

The immune system has multiple inhibitory pathways that are critical for maintaining self-tolerance and modulating immune responses. In T-cells, the amplitude and quality of response is initiated through antigen recognition by the T-cell receptor and is regulated by immune checkpoint proteins that balance co-stimulatory and inhibitory signals.

PD-1 is an immune checkpoint protein, that limits the activity of T cells in peripheral tissues at the time of an inflammatory response to infection and to limit autoimmunity PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (*Pardoll, Nature Reviews Cancer*, 12: 252-264, 2012). PD-1 blockade can be accomplished by a variety of mechanisms including antibodies that bind PD-1 or its ligands. Examples of PD-1 and PD-L1 blockers, also named PD-1 and PD-L1 inhibitors, are described in U.S. Pat. Nos. 7,488,802; 7,943,743; 8,008,449; 8,168,757; 8,217,149, and WO03042402, WO2008156712, WO2010089411, WO2010036959, WO2011066342, WO2011159877, WO2011082400, WO2011161699, and WO2015035606. In some embodiments the PD-1 inhibitors include an antibody or a fragment antigen binding thereof, which specifically binds to PD-1. In certain other embodiments the PD-1 blockers include anti-PD-1 antibodies and similar binding proteins such as nivolumab (MDX 1106, BMS 936558, ONO-4538, Opdivo®) described in U.S. Pat. No. 8,008,449B2, a fully human IgG4 antibody that binds to and blocks the activation of PD-1 by its ligands PD-L1 and PD-L2; pembrolizumab (lambrolizumab, MK-3475 or SCH 900475, Keytruda®) disclosed in U.S. Pat. No. 8,168,757B2, a humanized monoclonal IgG4 antibody against PD-1; pidilizumab (CT-011), a humanized antibody that binds PD-1; AMP-224, a fusion protein of B7-DC; an antibody Fc portion; BMS-936559 (MDX-1105-01) for PD-L1 (B7-H1) blockade for PD-1 blockade.

In some embodiments, the immune checkpoint inhibitor is an antibody or a fragment antigen binding thereof, or a chemical molecule drug. In some embodiments, the immune checkpoint inhibitor is a chemical molecule drug, which is an inhibitor of PD-1, PD-L1, PD-L2, TIM-3, Gal-9, CTLA-4, CD80, CD86, A2AR, B7-H3, B7-H4, BTLA, BTLA, HVEM, IDO1, IDO2, TDO, LAG3, VISTA, KIR, 2B4, CD2, CD27, CD28, CD30, CD40, CD90, CD137, CD226, CD276, DR3, GITR, ICOS, LAIR1, LIGHT, MARCO, PS, OX-40, SLAM TIGHT, CTCNI, or a combination thereof; or an antibody or a fragment antigen binding thereof, which specifically binds to one or more checkpoint proteins selected from PD-1, PD-L1, PD-L2, TIM-3, Gal-9, CTLA-4, CD80, CD86, A2AR, B7-H3, B7-H4, BTLA, BTLA, HVEM, IDO1, IDO2, TDO, LAG3, VISTA, KIR, 2B4, CD2, CD27, CD28, CD30, CD40, CD90, CD137, CD226, CD276, DR3, GITR, ICOS, LAIR1, LIGHT, MARCO, PS, OX-40, SLAM TIGHT, or CTCNI. In some embodiments, the immune checkpoint inhibitor is an anti-PD-1 antibody.

In some embodiments, the immune checkpoint inhibitor is a monoclonal antibody or a fragment thereof, disclosed in WO 2015/035606 A1.

Preferably, the anti-PD-1 monoclonal antibody is an antibody which comprises a heavy chain variable region (Vh) and a light chain variable region (Vl) that contain complement determinant regions (CDRs) listed as follows:

| | | |
|---|---|---|
| a) mu317 | | CDR-H1, CDR-H2 and CDR-H3 (SEQ ID NOs: 11, 12, 13, respectively); and CDR-L1, CDR-L2 and CDR-L3 (SEQ ID NOs: 14, 15, 16, respectively); |
| b) mu326 | | CDR-H1, CDR-H2 and CDR-H3 (SEQ ID NOs: 17, 18, 19, respectively); and CDR-L1, CDR-L2 and CDR-L3 (SEQ ID NOs: 20, 21, 22, respectively); |
| c) 317-4B6 | | CDR-H1, CDR-H2 and CDR-H3 (SEQ ID NOs: 31, 32, 33, respectively); and CDR-L1, CDR-L2 and CDR-L3 (SEQ ID NOs: 34, 35, 36, respectively); |
| d) 326-4A3 | | CDR-H1, CDR-H2 and CDR-H3 (SEQ ID NOs: 37, 38, 39, respectively); and CDR-L1, CDR--L2 and CDR-L3 (SEQ ID NOs: 40, 41, 42, respectively); |
| e) 317-1H | | CDR-H1, CDR-H2 and CDR-H3 (SEQ ID NOs: 11, 59, 13, respectively); and CDR-L1, CDR-L2 and CDR-L3 (SEQ ID NOs: 14, 15, 16, respectively); |
| f) 317-4B2 | | CDR-HL CDR-H2 and CDR-H3 (SEQ ID NOs: 11, 60, 13, respectively); and CDR-L1, CDR-L2 and CDR-L3 (SEQ ID NOs: 61, 15, 16, respectively); |
| g) 317-4B5 | | CDR-Hl, CDR-H2 and CDR-H3 (SEQ ID NOs: 11, 60, 13, respectively); and CDR-L1, CDR-L2 and CDR-L3 (SEQ ID NOs: 61, 15, 16, respectively); |
| h) 317-4B6 | | CDR-H1, CDR-H2 and CDR-H3 (SEQ ID NOs: 11, 32, 13, respectively); and CDR-L1, CDR-L2 and CDR-L3 (SEQ ID NOs: 61, 15, 16, respectively); |
| i) 326-1 | | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| j) 326-3B1 | | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| or k) 326-3G1 | | CDR-H1, CDR-H2 and CDR-H3 (SEQ ID NOs: 17, 62, 19, respectively); and CDR-L1, CDR-I 2 and CDR-L3 (SEQ ID NOs: 20, 21, 22, respectively). |

Preferably, the anti-PD-1 monoclonal antibody is an antibody which comprises a heavy chain variable region (Vh) and a light chain variable region (Vl) that contain any combinations of CDRs listed as follows:

(a) CDR-H1 (SEQ ID NO 31), CDR-H2 (SEQ ID NO 12, 32, 59 or 60) and CDR-H3 (SEQ ID NO 33),
CDR-L1 (SEQ ID NO 14, 34 or 61), CDR-L2 (SEQ ID NO 35) and CDR-L3 (SEQ ID NO 36); or
(b) CDR-H1 (SEQ ID NO 37), CDR-H2 (SEQ ID NO 18, 38 or 62) and CDR-H3 (SEQ ID NO 39),
CDR-L1 (SEQ ID NO 40), CDR-L2 (SEQ ID NO 41) and CDR-L3 (SEQ ID NO 42).

Preferably, the anti-PD-1 monoclonal antibody is an antibody which comprises a heavy chain variable region (Vh) and a light chain variable region (Vl) comprising:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);

-continued q) 317-311 (SEQ ID NOs: 70 and 26, respectively);
r) 317-4B1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

Preferably, the anti-PD-1 monoclonal antibody is an antibody which comprises an IgG4 heavy chain effector or constant domain comprising any of SEQ ID NOs: 83-88.

Preferably, the anti-PD-1 monoclonal antibody is an antibody which contains a F(ab) or F(ab)2 comprising a domain said above, including a heavy chain variable region (Vh), a light chain variable region (Vl) and a IgG4 heavy chain effector or constant domain.

Preferably, the anti-PD-1 monoclonal antibody is an antibody which comprise a heavy chain variable region (Vh) and a light chain variable region (Vl), and a IgG4 heavy chain effector or constant domain comprising SEQ ID NOs: 87 or 88, wherein the heavy chain variable region (Vh) and the light chain variable region (Vl) comprise:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

Preferably, the anti-PD-1 monoclonal antibody is an antibody which comprises a heavy chain variable region (Vh) and a light chain variable region (Vl) (comprising SEQ ID No 24 and SEQ ID No 26, respectively) and a IgG4 heavy chain effector or constant domain (comprising SEQ ID NO 88), hereinafter Mab1, which specifically binds to PD-1, especially PD-1 residues including K45 and 193; or, 193, L95 and P97, and inhibits PD-1-medidated cellular signaling and activities in immune cells, antibodies binding to a set of amino acid residues required for its ligand binding.

The anti-PD1 monoclonal antibodies and antibody fragments thereof may be prepared in accordance with the disclosure of WO2015/035606 A1, the entire disclosure of which is expressly incorporated herein by reference.

Chemotherapeutic Agent

In some embodiment, the PARP inhibitor is co-administered with a chemotherapeutic agent.

Chemotherapy is a category of cancer treatment that uses one or more anti-cancer drugs (chemotherapeutic agents) as part of a standardized chemotherapy regimen. In some embodiments, the chemotherapeutic agent is selected from paclitaxel, or etopside plus carboplatin (E/C).

PARP Inhibitors

"PARP inhibitor" means a compound of Formula (I), or a stereoisomer thereof, a pharmaceutically acceptable salt thereof, or a solvate thereof.

As disclosed in each of the above six aspects, the PARP inhibitor is a compound of Formula (I),

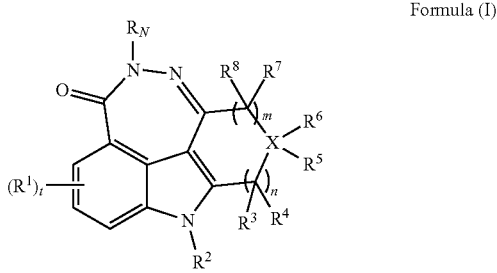

Formula (I)

a stereoisomer thereof, a pharmaceutically acceptable salts thereof, or a solvate thereof, wherein:

$R_N$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

X is selected from the group consisting of C, N, O, and S;

m and n, which may be the same or different, are each an integer of 0, 1, 2, or 3;

t is an integer of 0, 1, 2, or 3;

$R^1$, at each occurrence, is independently selected from halogen, CN, $NO_2$, $OR^9$, $NR_9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one sub stituent $R^{12}$;

$R^2$ is selected from hydrogen, $COR^9$, $CONR^9R^{10}$, $CO_2R^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^6$, $R^7$ and $R^8$, which may be the same or different, are each independently selected from hydrogen, halogen, —$NR^9R^{10}$, —$OR^9$, oxo, —$COR^9$, —$CO_2R^9$, —$CONR^9R^{10}$, —$NR^9CONR^{10}R^{11}$, —$NR^9CO_2R^{10}$, —$NR^9SO_2R^{10}$, —$SO_2R^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and 10, and/or ($R^7$ and $R^8$), together with the atom(s) they are attached, form a 3- to 8-membered saturated, partially or fully unsaturated ring having 0, 1 or 2 heteroatoms independently selected from —NR$^{13}$—, —O—, —S—, —SO— or —SO$_2$—, and said ring is optionally substituted with at least one substituent R$^{12}$, provided that when X is O, R$^5$ and R$^6$ are absent,
when X is N, R$^6$ is absent, an
when X is S, R$^5$ and R$^6$ are absent, or at least one of R$^5$ and R$^6$ is oxo,
when one of R$^3$ and R$^4$ is oxo, the other is absent,
when one of R$^7$ and R$^8$ is oxo, the other is absent, and
when X is C and one of R$^5$ and R$^6$ is oxo, the other is absent;

R$^9$, R$^{10}$, and R$^{11}$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one sub stituent R$^{12}$;

R$^{12}$ is selected from CN, halogen, haloalkyl, NO$_2$, —NR'R", —OR', oxo, —COR', —CO$_2$R', —CONR'R", —NR'CONR"R'", —NR'CO$_2$R", —NR'SO$_2$R", —SO$_2$R', alkyl, alkenyl, alkynyl, cycloalkyl, heterocyclyl, aryl, and heteroaryl, wherein R', R", and R'" are independently selected from hydrogen, haloalkyl, alkyl, arylalkyl, alkenyl, alkynyl, cycloalkyl, heterocyclyl, aryl, and heteroaryl, or (R' and R"), and/or (R" and R'") together with the atoms to which they are attached, form a 3- to 8-membered saturated, partially or fully unsaturated ring having 0, 1 or 2 additional heteroatoms independently selected from —NR$^{13}$—, —O—, —S—, —SO— and —SO$_2$—, R$^{13}$ is selected from hydrogen, alkyl, cycloalkyl, aryl, heteroaryl, and heterocyclyl.

In some embodiments, the PARP inhibitor is a compound of Formula (II),

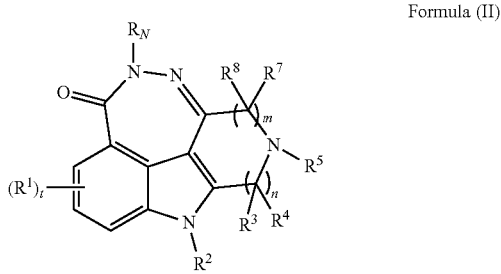

Formula (II)

a stereoisomer thereof, a pharmaceutically acceptable salts thereof, or a solvate thereof, wherein:

R$_N$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

m and n, which may be the same or different, are each an integer of 0, 1, 2, or 3;

t is an integer of 0, 1, 2, or 3;

R$^1$, at each occurrence, is independently selected from halogen, CN, NO$_2$, OR$_9$, NR$^9$R$^{10}$, NR$^9$CO$_2$R$^{10}$, —NR$^9$SO$_2$R$^{10}$, CONR$^9$R$^{10}$, COOR$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

R$^2$ is selected from hydrogen, COR$^9$, CONR$^9$R$^{10}$, CO$_2$R$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

R$^3$, R$^4$, R$^5$, R$^7$ and R$^8$, which may be the same or different, are each independently selected from hydrogen, halogen, —NR$^9$R$^{10}$, —OR$^9$, oxo, —COR$^9$, —CO$_2$R$^9$, —CONR$^9$R$^{10}$, —NR$^9$CO$_2$R$^{10}$, —NR$^9$SO$_2$R$^{10}$, —SO$_2$R$^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent R$^{12}$, or (R$^3$ and R$^4$), and/or (R$^4$ and R$^5$), and/or (R$^5$ and R$^7$), and/or (R$^7$ and R$^8$), together with the atom(s) they are attached, form a 3- to 8-membered saturated, partially or fully unsaturated ring having 0, 1 or 2 heteroatoms independently selected from —NR$^{13}$—, —O—, —S—, —SO—, and —SO$_2$—, and said ring is optionally substituted with at leaset one substituent R$^{12}$, provided that when one of R$^3$ and R$^4$ is oxo, the other is absent, and
when one of R$^7$ and R$^8$ is oxo, the other is absent; R$^9$, R$^{10}$, and R$^{11}$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

R$^{12}$ is selected from CN, halogen, haloalkyl, NO$_2$, —NR'R", —OR', oxo, —COR', —CO$_2$R', —CONR'R", —NR'CONR"R'", —NR'CO$_2$R", —NR'SO$_2$R", —SO$_2$R', alkyl, alkenyl, alkynyl, cycloalkyl, heterocyclyl, aryl, and heteroaryl, wherein R', R", and R'" are independently selected from hydrogen, haloalkyl, alkyl, arylalkyl, alkenyl, alkynyl, cycloalkyl, heterocyclyl, aryl, and heteroaryl, or (R' and R"), and/or (R" and R'") together with the atoms to which they are attached, form a 3- to 8-membered saturated, partially or fully unsaturated ring having 0, 1 or 2 additional heteroatoms independently selected from —NR$^{13}$—, —O—, —S—, —SO— or —SO$_2$—; and R$^{13}$ is selected from hydrogen, alkyl, cycloalkyl, aryl, heteroaryl, and heterocyclyl.

In some embodiments, the PARP inhibitor is selected from the compound the following compounds,

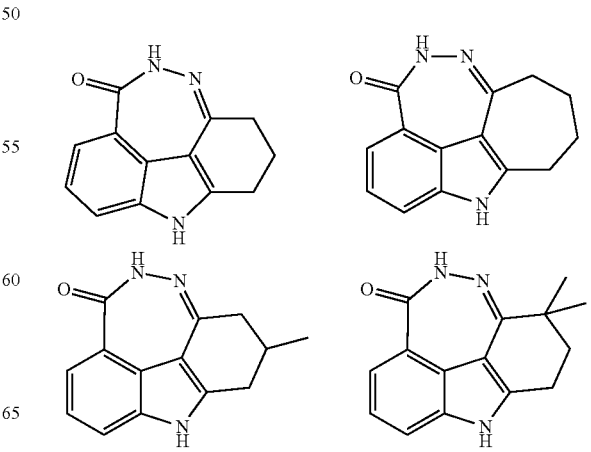

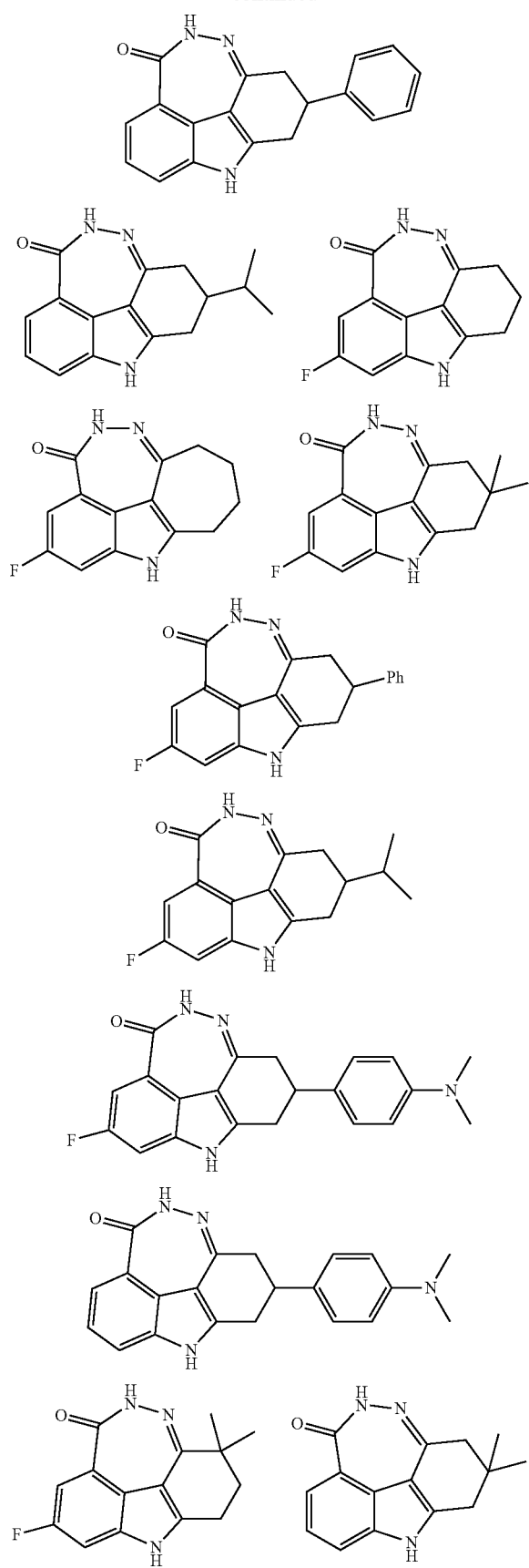
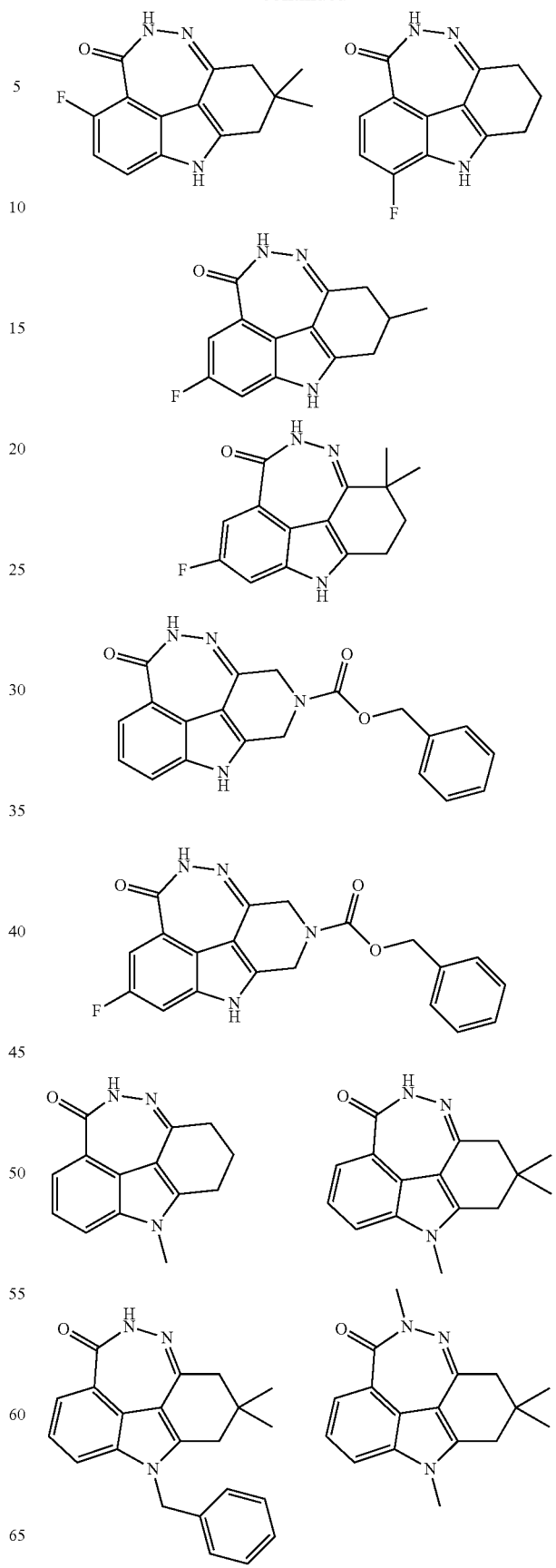

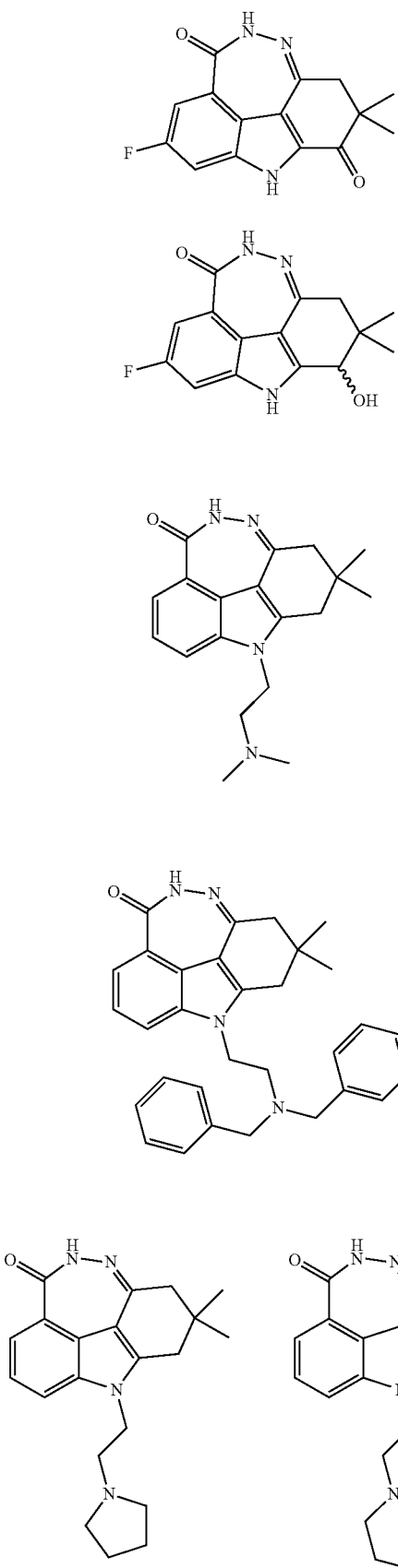
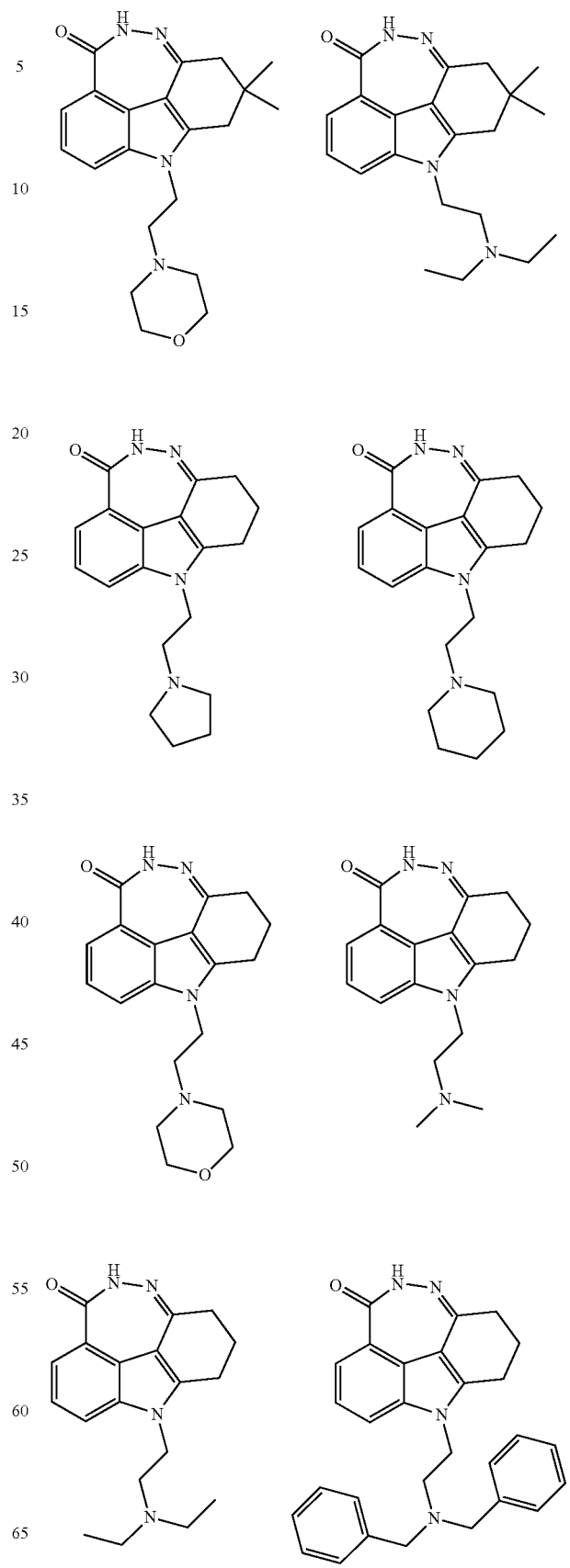

-continued
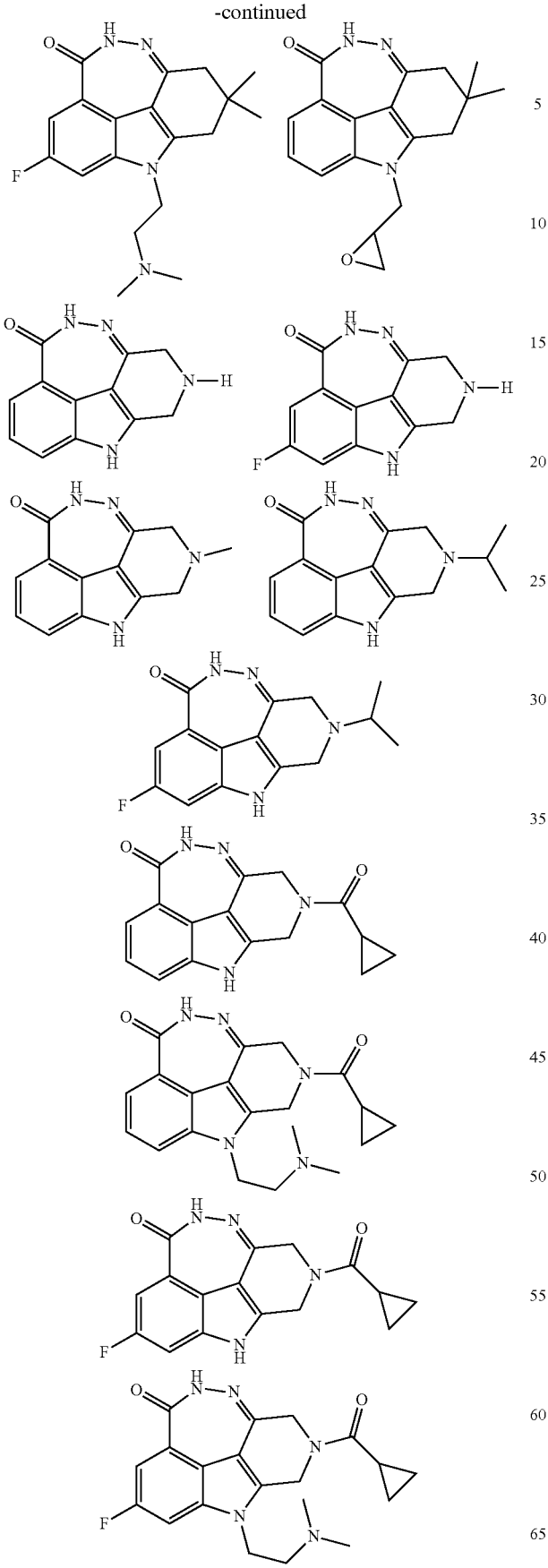
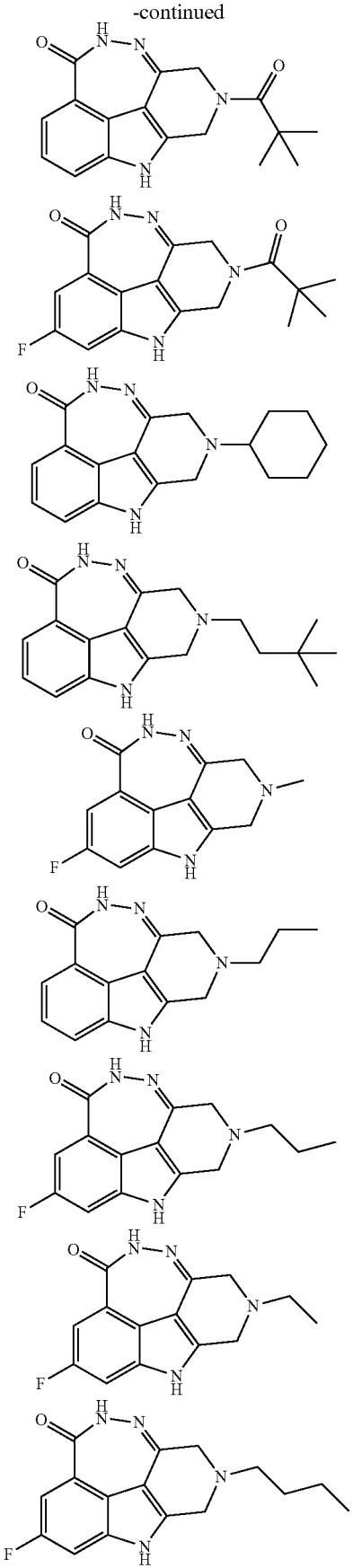

-continued

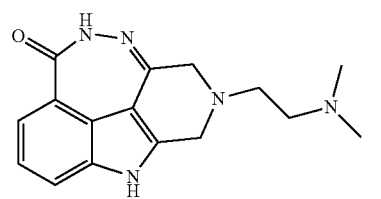

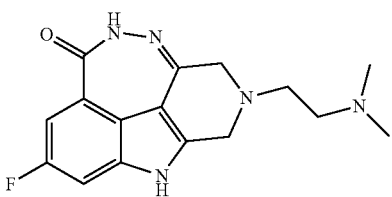

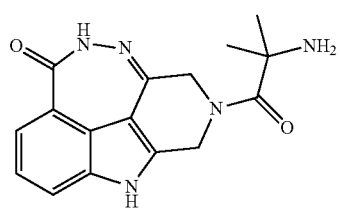

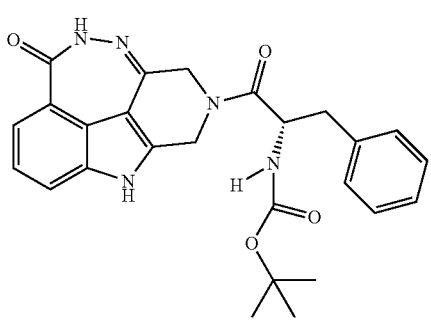

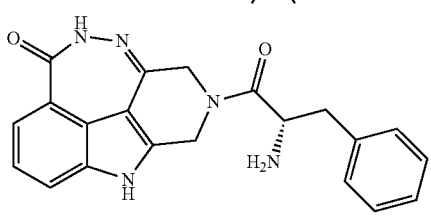

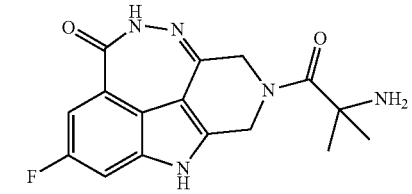

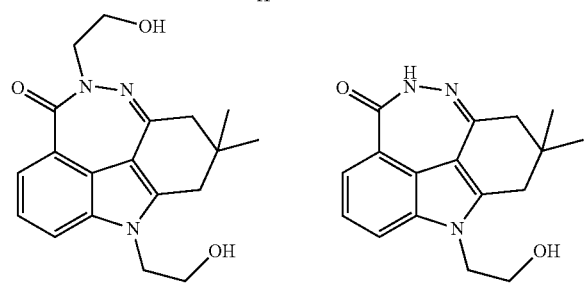

-continued

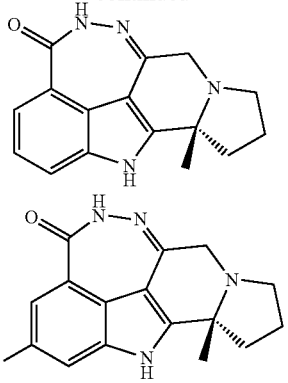

a stereoisomer thereof, a pharmaceutically acceptable salts thereof, or a solvate thereof.

As disclosed in each of the above six aspects, the PARP inhibitor is a compound of Formula (III)—i.e., Compound A, Formula (III)

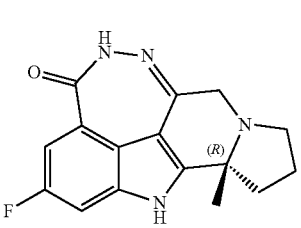

or a pharmaceutically acceptable salt thereof.

As disclosed in each of the above six aspects, the PARP inhibitor is a compound of Formula (IV)—i.e., Compound B.

Formula (IV)

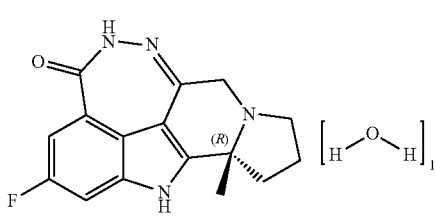

The PARP inhibitor disclosed herein, such as the compound of Formula (III) and (IV), may be synthesized by synthetic routes disclosed in WO2013/097225A1 and PCT application PCT/CN2016/096200, the entire disclosure of which is expressly incorporated herein by reference.

Combination Therapy

The combination therapy may be administered as a simultaneous, or separate or sequential regimen. When administered sequentially, the combination may be administered in two or more administrations. The combined administration includes co-administration, using separate formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the PARP inhibitor and the chemotherapeutic agent or the immune checkpoint inhibitor, such as to increase the therapeutic index or mitigate toxicity or other side-effects or consequences.

In a particular embodiment of anti-cancer therapy, the PARP inhibitor and the chemotherapeutic agent or the immune checkpoint inhibitor may be further combined with surgical therapy and radiotherapy.

In an embodiment of each of the above six aspects, the amounts of the PARP inhibitor and the chemotherapeutic agent or the immune checkpoint inhibitor disclosed herein and the relative timings of administration be determined by the individual needs of the patient to be treated, administration route, severity of disease or illness, dosing schedule, as well as evaluation and judgment of the designated doctor.

For example, the administered dosage of the PARP inhibitor is 1-120 mg (in terms of the parent compound), preferably, 1-80 mg (in terms of the parent compound), and the administration frequency is twice a day (BID); the administered dosage of the PARP inhibitor is 1-120-240 mg (in terms of the parent compound), preferably, 60-120 mg (in terms of the parent compound), and the administration frequency is once a day (QD). In some cases, it is more suitable to apply the lower end of the above described dosage ranges, while in other cases the higher dosages may be used without causing harmful side effects.

The PD-1 antagonist is administered at a dose of 0.5-30 mg/kg, such as 0.5-20 mg/kg, further such as 0.5-10 mg/kg once weekly (QW), or every two weeks (Q2W), or every three weeks (Q3W), or every four weeks (Q4W). Preferably, the PD-1 antagonist is administered at dose of 2 mg/kg every three weeks (Q3W), or at dose of 200 mg every three weeks (Q3W).

The PARP inhibitor and the chemotherapeutic agent or the immune checkpoint inhibitor disclosed herein may be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

In one embodiment of each of the above six aspects, the PARP inhibitor and the chemotherapeutic agent or the immune checkpoint inhibitor disclosed herein may be administered in different route. In a preferred embodiment, the PARP inhibitor is administered orally, and the chemotherapeutic agent or the immune checkpoint inhibitor is administered parenterally such as subcutaneously, intracutaneously, intravenously or intraperitoneally.

In an embodiment of each of the above six aspects, the anti-PD-1 monoclonal antibody is an antibody named as Mab-1, which comprises a heavy chain variable region (Vh) and a light chain variable region (V1) (comprising SEQ ID No 24 and SEQ ID No 26, respectively) and a IgG4 heavy chain effector or constant domain (comprising SEQ ID NO 88); and the PARP inhibitor is the compound of Formula (III) or (IV) disclosed herein.

In an embodiment of each of the above six aspects, the PD-1 antagonist Mab-1 is administrated to a subject at a dose of 0.5-20 mg/kg i.v. or i.p. QW or Q2W or Q3W or Q4W, and the PARP inhibitor Compound A or Compound B is administrated to a subject at a dose of 1-120 mg BID. In some preferred embodiments, the PD-1 antagonist Mab-1 is administrated to a subject at a dose of 0.5-10 mg/kg i.v. or i.p. QW or Q2W or Q3W or Q4W, and the PARP inhibitor Compound A or Compound B is administrated to a subject at a dose of 1-80 mg BID. In some embodiment of each of the above six aspects, the PD-1 antagonist Mab-1 is administrated to a subject at a dose of 2 mg/kg every three weeks (Q3W), and the PARP inhibitor Compound A or Compound B is administrated to a subject at a dose of 1-80 mg BID. In some embodiment of each of the above six aspects, the PD-1 antagonist Mab-1 is administrated to a subject at a dose of 2 mg/kg Q3W, and the PARP inhibitor Compound A or Compound B is administrated to a subject at a dose of at the PARP inhibitor at 20 mg, 40 mg or 60 mg BID, preferably, at a dose of 40 mg BID. In some embodiment of each of the above six aspects, the PD-1 antagonist Mab-1 is administrated to a subject at a dose of 200 mg Q3W, and the PARP inhibitor Compound A or Compound B is administrated to a subject at a dose of 40 or 60 mg BID, preferably, at a dose of 40 mg BID.

EXAMPLES

The present invention is further exemplified, but not limited, by the following examples that illustrate the invention. In the examples of the present invention, the techniques or methods, unless expressly stated otherwise, are conventional techniques or methods in the art.

Example 1. Preparation of Compound A and Compound B

Step 1: Synthesis of Compound-2

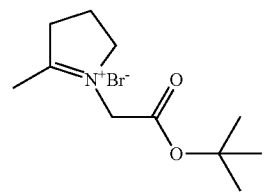

t-Butyl bromoacetate (51.7 Kg) was dissolved in anhydrous acetonitrile (72 Kg). The temperature was raised to 65-75° C., then methyl pyrroline (22 Kg) was added. The reaction mixture was condensed after the reaction was completed, the residual acetonitrile was removed by adding THF and then condensing. After GC showed a complete removal of acetonitrile, more THF was added and stirred. The resulting solid was filtered and collected. 44.1 Kg of off white solid Compound-2 was obtained. $^1$H NMR (400 MHz, DMSO-d6) δ 4.91 (s, 2H), 4.15 (m, 2H), 3.29 (m, 2H), 2.46 (s, 3H),), 2.14 (m, 2H), 1.46 (s, 9H)ppm.

Step 2: Synthesis of Compound-3

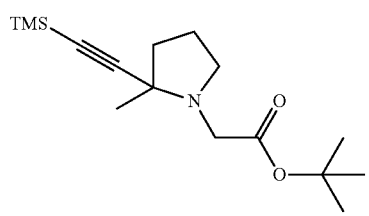

To a cool (−60° C.) solution of trimethylsilyl acetyne (12.4 Kg) in THF was added a solution of n-butyl lithium in hexane (43.4 Kg). After complete addition of n-butyl lithium solution, the resulting mixture was stirred for additional 1-2 h and then the entire solution was transferred into a suspension of Compound-2 (31 Kg) in THF cooled at −60° C. After transfer completion, the resulting mixture was warmed to room temperature and stirred for 1 h. The reaction was quenched with water, extracted with petroleum. The organic phase was washed with brine, dried over sodium sulfate, condensed to give 25.1 Kg of Compound-3. $^1$H NMR (400 MHz, DMSO-d6) δ 3.34 (d, J=16.0 Hz, 1H), 3.15 (m, 1H), 2.78 (d, J=16.0 Hz, 1H), 2.27 (m, 1H), 1.93 (m, 1H), 1.68 (m, 3H), 1.41 (s, 9H), 1.24 (s, 3H), 0.13 (s, 9 H) ppm.

Step 3: Synthesis of Compound-4

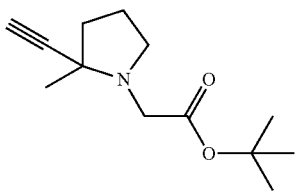

4

To a cool (0-5° C.) solution of 70.1 Kg of Compound-3 in THF was added tetrabutylammonium fluoride (13.3 Kg) in THF. After de-silylation was completed, the reaction was quenched with water, extracted with petroleum (290 Kg) and the organic phase was condensed and passed through a pad of silica gel. The filtrate was condensed to give 48 Kg of Compound-4. $^1$H NMR (400 MHz, DMSO-d6) δ 3.36 (d, J=16.0 Hz, 1H), 3.15 (m, 1H), 2.82 (d, J=16.0 Hz, 1H), 2.28 (m, 1H), 1.97 (m, 1H), 1.70 (m, 3H), 1.41 (s, 9H), 1.26 (s, 3H) ppm.

Step 4: Syntheses of Compound-5

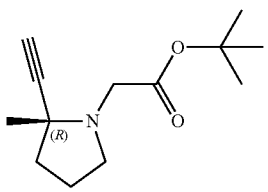

5

A solution of Compound-4 (48 Kg) in THF was warmed to 50-60° C. To the above solution was added a solution of (−)-di-p-methylbenzoyl-L-tartaric acid (69.6 Kg) in THF. The resulting mixture was stirred at 50-60° C. 1-2 h and then gradually cooled to 0-10° C. The resulting salt solid was filtered and re-suspended in methyl tert-butyl ether and heated at 50-60° C. for 1 h. The mixture was gradually cooled to 0-5° C. The resulting solid was filtered to give 13.1 Kg of off-white solid. The solid was treated with aqueous sodium hydroxide, extracted with petroleum, condensed to give 13.1 Kg of Compound-5 (ee NMR (400 MHz, DMSO-d6) δ 3.36 (d, J=16.0 Hz, 1H), 3.15 (m, 1H), 2.82 (d, J=16.0 Hz, 1H), 2.29 (m, 1H), 1.97 (m, 1H), 1.70 (m, 3H), 1.41 (s, 9H), 1.26 (s, 3H) ppm.

Step 5: Syntheses of Compound-6

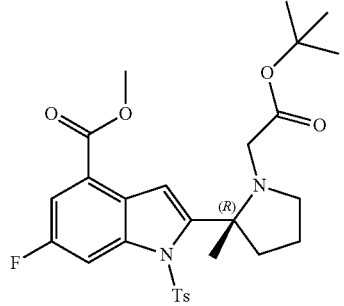

6

Intermediate B (14 Kg), bis(triphenyl)palladium dichloride (0.7 Kg), CuI (0.42 Kg) and tetramethyl guanidine (11.5 Kg) were dissolved in DMF (48.1 Kg). The resulting solution was stirred and de-gassed and then heated under nitrogen. A solution of Compound-5 (9.24 Kg) in DMF (16 Kg) was added dropwise. After coupling, the organic phase was condensed, the resiue was stirred with water (145 Kg) and methyl t-butyl ether (104 Kg), the entire mixture passed trough a pad of celite, separated. The organic phase was washed with a solution of thiourea (14 Kg) in water (165 kg) and brine (100 Kg), condensed. The residue was dissolved in a mixture of n-heptane (120 Kg) and ethyl acetate (28 Kg). The solution was mixed with charcoal (1.4 kg), heated at 40-50° C. for 1-2 h, fltered though a pad of silica gel. The filtrate was condensed to give Compound-6 solid (14.89 Kg) and the liquid filtrate (13 Kg heptane solution, contains 1.24 Kg of Compound-6). $^1$H NMR (400 MHz, DMSO-d6) δ 7.85 (d, J=9.6 Hz, 1H), 7.55 (m, 3H), 7.32 (m, 2H), 3.87 (s, 3H), 3.37 (d, J=16.0 Hz, 1H), 3.22 (m, 1H), 2.94 (d, J=16.0, Hz, 1H), 2.60 (m, 1H), 2.48 (m, 1H), 2.29 (s, 3h), 2.26 (m,1H), 1.82 (m, 2H), 1.49 (s, 3H), 1.43 (s, 9H) ppm.

Step 6: Syntheses of Compound-7

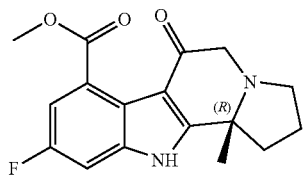

7

The above heptane solution of Compound-6 was added into a cold trifluoromethane sulfonic acid (66.1 Kg) while maintaining the internal temperature below 25° C. Then solid Compound-6 (14.87 Kg) was added batchwise. After complete addition of Compound-6, the reaction mixture was warmed to 25-30° C. and stirred until the reaction was completed. The entire mixture was poured into a solution of sodium acetate (123.5 Kg) in water (240 Kg). pH of the solution was then adjusted to 7-8 by adding solid potassium carbonate (46.1 Kg). The mixture was extracted with dichloromethane (509 Kg), condensed. The residue was mixed with n-heptane (41 Kg), condensed again to give the precipitate which was filtered and washed by n-heptane (8 Kg) and dried. 8.78 Kg of Compound-7 was obtained. $^1$H NMR (400 MHz, DMSO-d6) δ 12.30 (s, 1H), 7.35 (dd, J=9.2, 1.6 Hz, 1H), 7.08 (dd, J=9.2, 1.6 Hz, 1H), 3.79 (s, 3H), 3.68 (d, J=17.2 Hz, 1H), 3.21 (d, J=17.2 Hz, 1H), 3.06 (m, 1H), 2.68 (m, 1H), 1.96 (m, 1H), 1.74 (m, 1H), 1.49 (s, 3H) ppm.

Step 7: Syntheses of Compound A-Crude 1

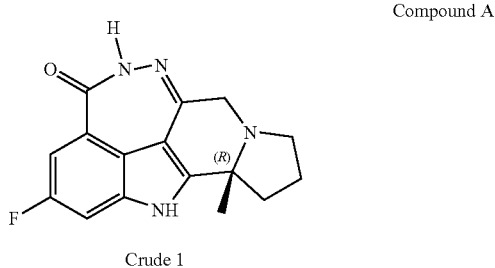

Crude 1

Compound-7 (8.76 Kg) was dissolved in methanol (69 Kg) and internally cooled below 25° C. Acetic acid (9.3 Kg) and hydrazine hydrate (7.4 Kg, 85%) were added while maintaining internal temperature below 25° C. After degassed and re-filled with nitrogen (repeated three times), the reaction mixture was stirred at 55-60° C. for 4 h. After a complete reaction, the mixture was mixed with water (29 Kg). The organic phase was condensed and potassium carbonate (12.5 Kg) in water (40 Kg) was added. The resulting solid was filtered, washed with water (18.3 Kg). The solid was slurred with water (110 Kg), centrifuged, dried and slurred with ethanol (9.4 Kg), centrifuged, filtered, washed with ethanol, dried in vaccum to give Compound A-Crude 1 (7.91 Kg). $^1$H-NMR (600 MHz, DMSO-d6) δ 12.0 (s, 1H), 10.2 (s, 1H), 7.31 (dd, 1H, J=9.6, 2.0 Hz), 7.19 (dd, 1H, J=9.6, 2.0 Hz), 3.77 (d, 1H, J=16.4 Hz), 3.34 (d,1H, J=16.4 Hz), 2.97-3.02 (m, 1H), 2.54-2.58 (m, 1H), 2.35-2.40 (m, 1H), 1.90-1.94 (m, 1H), 1.73-1.75 (m, 1H), 1.47 (s, 3H), 1.43-1.45(m, 1H) ppm. MS (ESI) m/e [M+1]$^+$299.

Step 8: Synthesis of Compound A-Crude 2

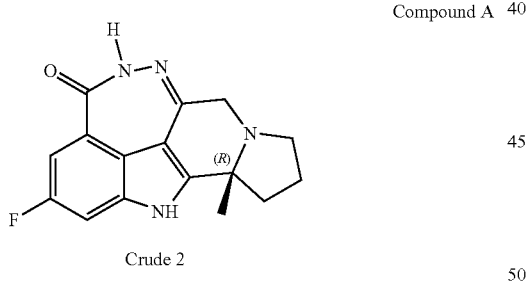

Crude 2

Under nitrogen protection, Compound A (Crude 1) (7.88 Kg) was stirred with isopropanol (422 Kg) and heated at 70-80° C. for 1-2 h until the solid disappeared completely. A solution of (+)-di-p-methylbenzoyl-D-tartaric acid (10.25 Kg) in isopropanol (84.4 Kg) was added. The mixture was stirred for 14-16 h, filtered and washed with isopropanol (16 Kg), dried. The resulting salt was added into a stirred solution of potassium carbonate (6.15 Kg) in water (118 Kg). The precipitate was centrifuged, filtered, washed with water (18 Kg). The solid was slurred with water (110 Kg), centrifuged, dried. The solid was dissolved in THF (75 Kg), active carbon (0.8 Kg) was added. The mixture was degassed and re-protected by nitrogen, stirred and heated at 40-45° C. for 1-2 h, cooled, filtered through celite, condensed to give the solid which was further slurred with ethanol (6.5 Kg), filtered to give 5.6 Kg of Compound A crude 2. $^1$H NMR (400 MHz, DMSO-d6) δ 12.0 (s, 1H), 10.2 (s, 1H), 7.31 (dd, 1H, J=9.6, 2.0 Hz), 7.19 (dd, 1H, J=9.6, 2.0 Hz), 3.77 (d, 1H, J=16.4 Hz), 3.34 (d,1H, J=16.4 Hz), 2.97-3.02 (m, 1H), 2.54-2.58 (m, 1H), 2.35-2.40 (m, 1H), 1.90-1.94 (m, 1H), 1.73-1.75 (m, 1H), 1.47 (s, 3H), 1.43-1.45(m, 1H) ppm. MS (ESI) m/e [M+1]$^+$299.

Step 9: Synthesis of Compound B

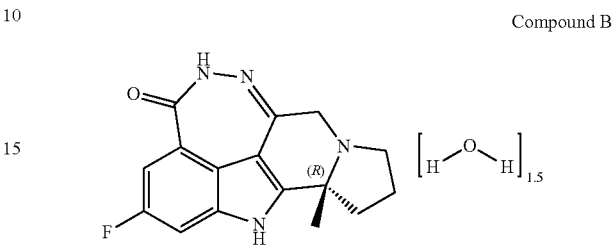

Compound A-Crude 2 (5.3 Kg) was mixed with a solution of isopropanol (41.6 Kg) and water (15.9 Kg). The mixture was degassed and re-protected under nitrogen and then heated to 60° C. and stirred for 2-4 h until the solid was dissolved completely. The temperature was raised to 70-80° C. and water (143 Kg) was added. The resulting mixture was heated to the internal temperature of 70-80° C. and then the heating was stopped but stirred gently for 16 h. The precipitate was filtered, washed with water (19 Kg) and slurred with water (21 kg) for 2 h. The resulting solid was filtered, washed with water (20 Kg). The filtered solid was dried at the temperature below 45° C. for 24-36 h. Compound A sesqui-hydrate (4.22 kg) was obtained with particle sizes of D90=51.51 um, D50=18.62 um, D10=7.63 um. This range of PSD is almost ideal for formulation development.

Figure 2:
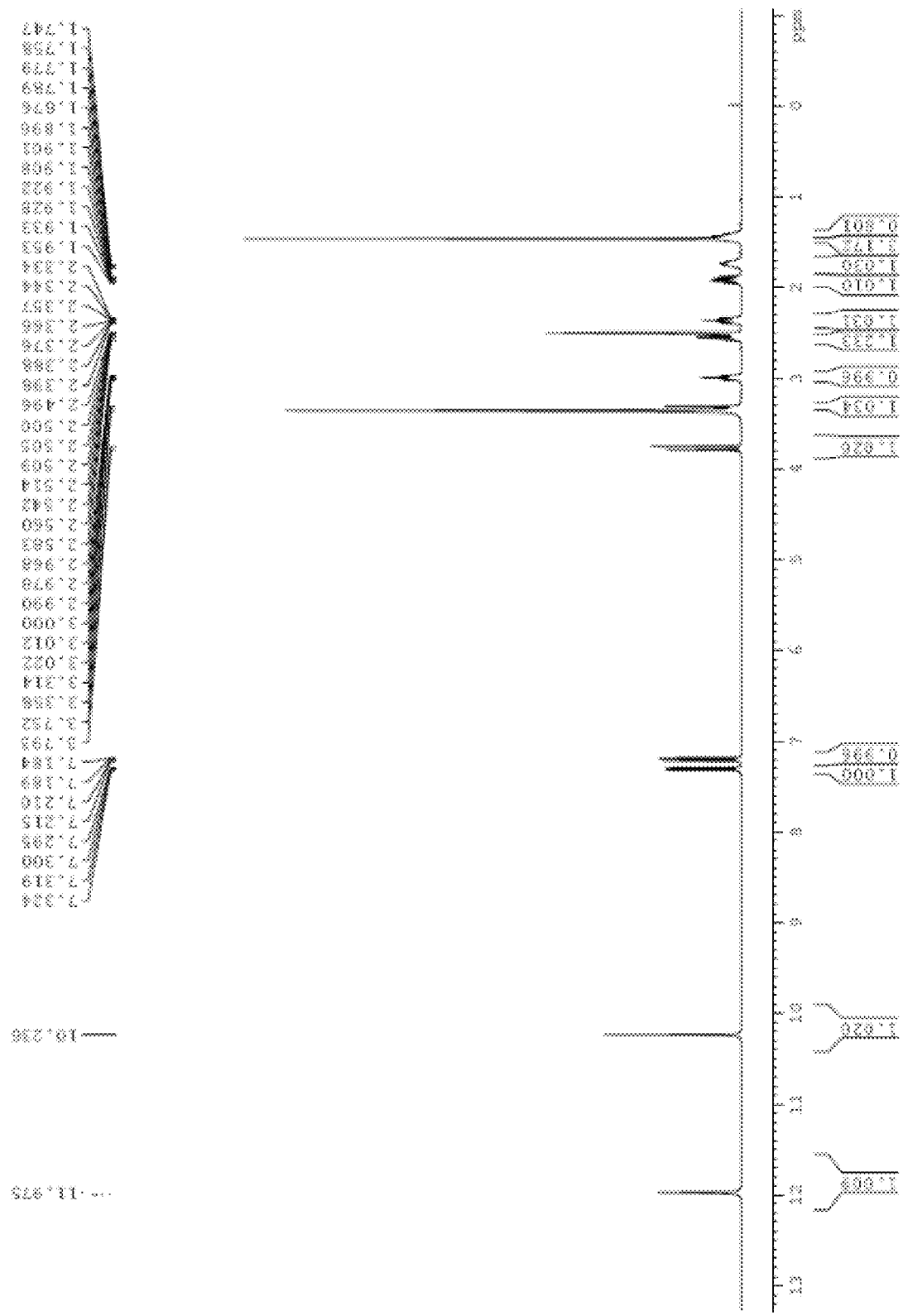
FIG. 2 shows the $^1$H-NMR of crystal Compound B.
Figure 3:
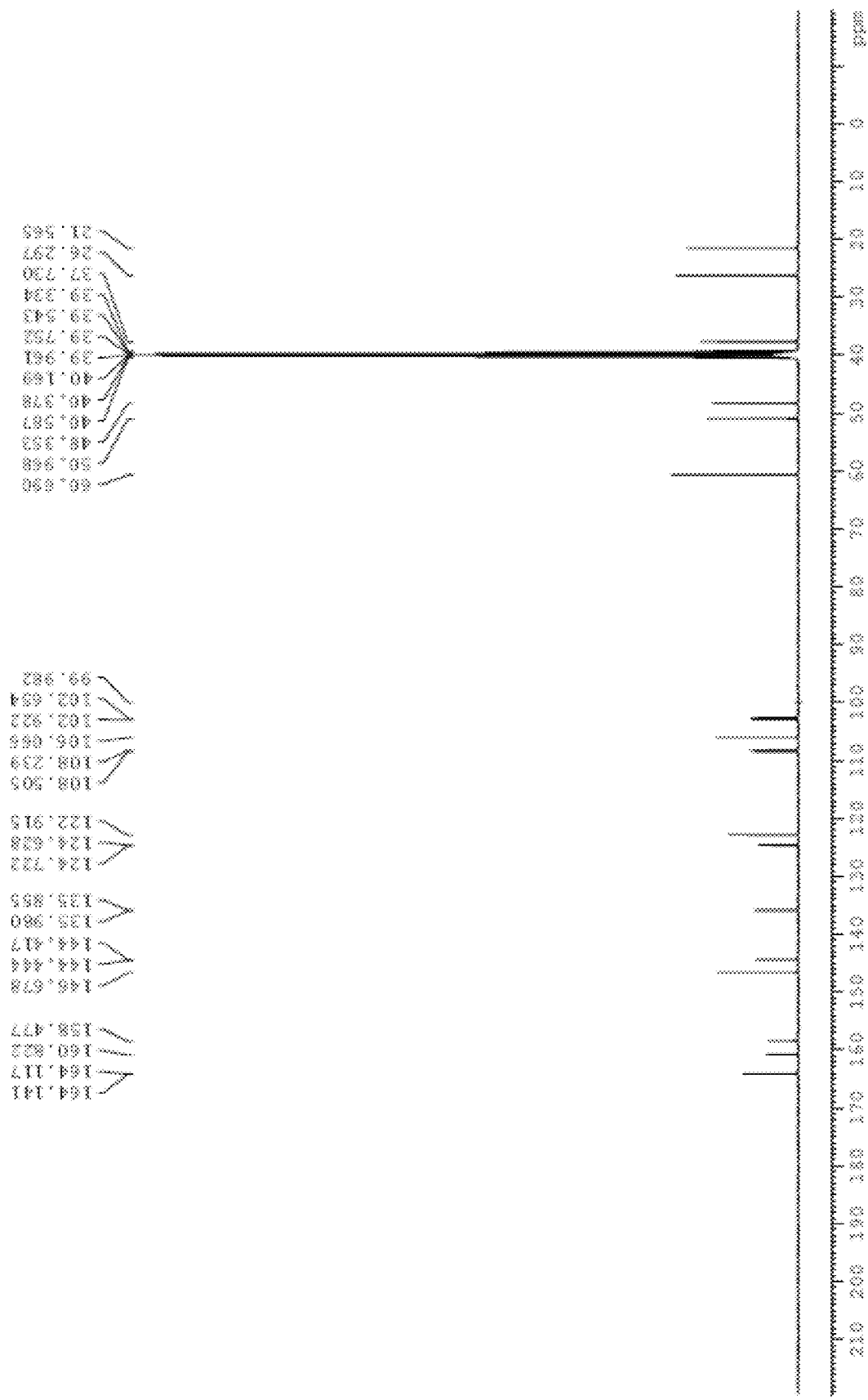
FIG. 3 shows the $^{13}$C-NMR of crystal Compound B.

The powder X-ray diffraction pattern (PXRD) was used to characterize Crystal Compound 2, see FIG. 1. $^1$H-NMR for Crystal Compound 2, is shown in FIG. 2. $^{13}$C-NMR for Crystal Compound 2 is shown in, see FIG. 3.

Example 2 Effect of the Combination of PARP Inhibitor and Anti-PD-1 mAb

Materials and Methods

PBMC Isolation and Activation

After signed the informed consent, healthy human donor's blood was collected and PBMCs were isolated with Ficoll (GE Healthcare, 17-1440-02) according to the manufacturer's protocol with small modification. Briefly, fresh blood was diluted with equivalent volume of 1×DPBS (Gibco®, 14190-144), added equivalent volume of Ficoll into a 50 mL sterile tube, and added diluted blood very carefully onto the surface of the Ficoll. Then centrifuged at 400 g for 40 minutes at room temperature. Carefully removed the upper layer and pipetted the lymphocyte layer to a clean sterile tube, added 3 volumes of 1×DPBS and centrifuge at 200 g for 10 minutes at room temperature. After discarded the supernatant, suspended cells with 10 mL 1×DPBS and washed 2 times more. Suspended cells with 5 mL RPMI-1640 (Gibco®, 22400-089) complete medium (added with 10% fetal bovine serum (Gibco®, 10099-141).

For the activation of PBMCs, 5 mL 1×DPBS with 1 μg/mL anti-CD3 antibody (eBioscience, 16-0037-85) was added to a T25 plate (Corning, 430168), incubate at 4° C. overnight. Liquid in the T25 plate was discarded and the plate was washed with 5 mL 1×DPBS for 2 times, discarded 1×DPBS and added fresh isolated 6-8×10$^6$ PBMCs suspended in 5 mL RPMI-1640 complete medium. Put the plate at 37° C., 5% $CO_2$ cell incubator. 2 to 3 days later, cells was collected and counted amount.

Primary Human Tumor Cell Isolation

After a patient with cancer signed the informed consent, tumor biopsy or surgical tumor tissue sample from patient was collected. At the day of tumor collection, tumor was sterilely minced to small pieces at a biosafety cabinet. Then tumor pieces was suspended with 10 mL digestion buffer, digested at 37° C. and 200 rpm for 0.5-1 hour. Undigested tumor pieces were removed by filtering with a 70 μm strainer. Liquid with tumor cells passed the strainer was centrifuged at 300 g for 5 minutes at room temperature. Discarded the supernatant and suspended cells with 10 mL 1×DPBS and washed 2 times more. The cells are re-suspended with Medium BGB.

The medium is Medium BGB comprises a substance listed as follows:
1) F12/DMEM 1:1 medium 500 mL (Gibco®, 31765-035);
2) Fetal Bovine Serum 50 ml (Gibco®, 10099-141);
3) B-27 supplement 1× (Gibco®, 17504-044);
4) B2 supplement 1× (Gibco®, 17502-048);
5) Insulin-Transferrin-Selenium (ITS-G) 0.5× (Gibco®, 41400045);
6) N-Acty-L-Cysteine 1.25 mM (Sigma®, V900429);
7) L-Ascorbic acid 25 ug/ml (Sigma®, V900134);
8) Folic acid 3.5 uM (Sigma®, V900422);
9) Putrescine 180 uM (Sigma®, V900377);
10) [Leu15]-Gastrin 10 nM (Sigma®, SCP0151);
11) Selenium 1.2 uM (Gibco®, 51300-044);
12) Glucose 25 mM (Sigma®, V900392);
13) Beta-ME 0.2 mM (Sigma®, M7522-100ML);
14) Recombinant Human HB-EGF 10 ng/ml (Peprotech, 100-47);
15) Recombinant Human R-Spondin-1 1 μg/ml (Peprotech, 120-38);
16) Recombinant Human Noggin 100 ng/ml (Peprotech, 120-10C);
17) HEPES 1× (Gibco®, 15630080);
18) Glutamine 2 mM (Gibco®, 25030081);
19) MEM Non-Essential Amino Acids Solution 1× (Gibco®, 11140050);
20) Sodium pyruvate 1× (Gibco®, 11360070);
21) Penicillin-Streptomycin 1× (Gibco, 15140122); and
22) ROCK inhibitor y-27632 10 μM (Sigma®, Y0503).

Flow Cytometry Analysis

Activated PBMCs were collected and washed with 1×DPBS. $3×10^5$ cells were stained with a fluorescent probe conjugated anti-PD-1 antibody (eBioscience, 12-2799-42). The PD-1 expressed on PBMCs was analyzed by flow cytometry.

Culturing Primary Human Tumor Cells on Feeder Cells

C3H10T1/2 cell (ATCC, ATCC® CCL-226™) is a mouse embryo cell line and used as feeder cell. When the confluence of C3H10T1/2 cell was about 90%, cells were treated with 10 μg/mL mitomycin C (MCC, Sigma®, M0503) at 37° C. for 2 hours. Then discarded the medium with MMC and washed with 1×DPBS for 3 times. Cells were collected and stored in liquid-nitrogen. 4 hours before isolated primary tumor cells were seeded, MMC treated C3H10T1/2 cells were seeded into a 6-well plate. Two days after tumor cells were seeded, changed medium to remove unattached cells. Medium was changed according to the medium color. When the confluence was about 70-90%, primary tumor cells were trypsinized and subcultured to 96-well plate which was pre-seeded with MMC treated C3H10T1/2. Culture primary tumor cells to the confluence sufficient to co-culture with PBMCs Culturing Primary Human Tumor Cells in Matrigel®

Isolated primary tumor cells suspended in medium were mixed with 2% Matrigel® (BD, 356234) and then seeded in a 48-well plate. Medium was changed according to the medium color. When cells should be subcultured, organoids in Matrigel® were collected and pipetted to dispense the Matrigel® to small pieces and subcultured to a 96-well plate to co-cultrue with PBMCs.

ELISA for Human IFN-γ

Coated a 96-well high binding plate (Corning, 9018) with purified anti-human IFN-γ (Biolegend, 502402) at 37° C. for 2 hours or overnight, after washed the plate with 1×PBST (PBS added with 0.5% Tween 20 (Sigma®, P1379) for 3 times, plate was blocked with 3% BSA (ChemCruz®, sc-2323) resolved in 1×PBST. Then supernatant of the co-culture system was incubated at room temperature for 2 hours or overnight. After washed the plate with 1×PBST for 3 times, plate was incubated with biotin conjugated anti-human IFN-γ (Biolegend, 502504) at room temperature for 1 hour. After washed the plate with 1×PBST for 3 times, plate was incubated with HRP conjugated streptavidin (Themo Scientific, 21130) at room temperature for 30 minutes. After washed the plate with 1×PBST for 5 times, 100 μL 1×TMB (ebioscience, 00-4201-56) was added to each well of the plate, 5 to 15 minutes later, each well was added with 50 μL of 2 mM $H_2SO_4$ to stop the reaction. Read absorbance at 450 nm.

Effect of the Combination of PARP Inhibitor and Anti-PD-1 mAb

Figure 4:
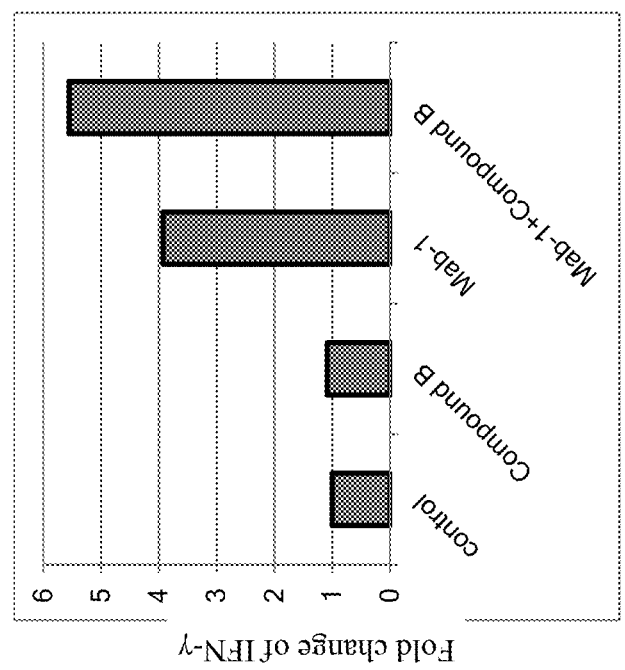
FIG. 4 shows the level of IFN-γ produced from PBMCs in primary human tumor cells cultured in Matrigel®/PBMCs co-culture system treatment with Compound B, Mab-1 or the combination of Mab-1 and Compound B), in the EpCAM×CD3 bispecific T cell engager platform.
Figure 4:
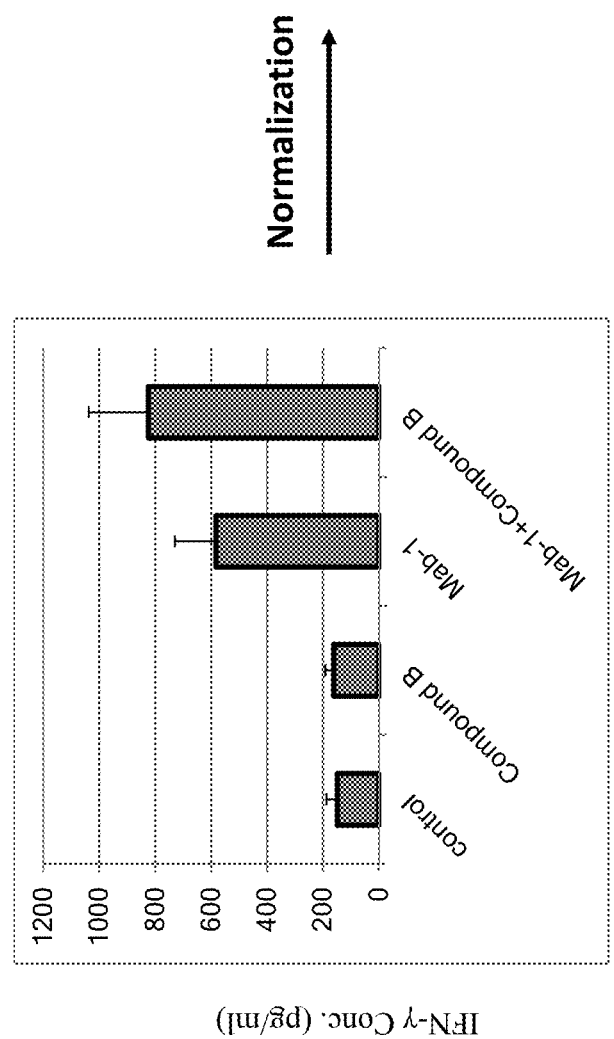

Primary tumor cells from a patient with colorectal cancer cultured in Matrigel® were co-cultured with non pre-activated allogeneic human PBMCs, with 50 ng/ml EpCAM× CD3 bispecific T cell engager and with or without an PARP inhibitor named Compound B (30 nM) or an anti-PD-1 antibody named Mab-1 (1 μg/mL), or their combination (named as Mab-1+ Compound B, for short), and cultured for 72 hours. Human IFN-γ in the supernatant of the co-culture system was measured and as the readout (See FIG. 4). The IFN-γ concentration of each bispecific T cell engager concentration group was normalized to fold change by antibody treatment group concentration dividing by control group concentration. Primary tumor cells cultured in Matrigel® responded to anti-PD-1 antibody.

With 50 ng/mL bispecific T cell engager, the fold changes of IFN-γ of Compound B group was only almost close to 1 (the value is 1.08), which indicates that the primary tumor cells probably not respond to 30 nM Compound B alone. While the fold changes of anti-PD-1 antibody and the combination treatment groups were all bigger than 1.3, the fold changes of combination was bigger than anti-PD-1 antibody alone treatment groups, which indicated that the primary tumor cells not only responded to anti-PD-1 antibody alone, but also there was significant synergistic effect of anti-PD-1 antibody and Compound B on primary tumor cells cultured in Matrigel®. The results indicated that this cancer patient not only responded to the tested anti-PD-1 antibody, but also responded to the effect of its combination with Compound B. The effect of the combination of Mab-1 and Compound B showed better activity than the single anti-PD-1 antibody treatment, indicating there was significant synergistic effect of the anti-PD-1 antibody (Mab-1) and Compound B on primary tumor cells cultured in Matrigel®.

Example 3 Effect of the Combination of PARP Inhibitor and Paclitaxel in a Primary Human Gastric Tumor Xenograft Model Method Tumor tissues surgically removed from a patient with gastric cancer. Within 2 to 4 hours following patient surgery, small fragments of tumor (3×3×3 mm$^3$) were subcutaneously engrafted into the scapular area of anesthetized NOD/SCID mice. After tumors grew to around 300-1000 mm$^3$, tumors were surgically removed and fragments were passaged in NOD/SCID mice by subsequent engraftments. Engraftment in BALB/c nude mice was conducted after 3 successfully passages in NOD/SCID mice. The right axilla region of each BALB/C nude mouse was cleaned with 70% ethanol prior to tumor fragments inoculation. Each animal was implanted subcutaneously with a fragment (around 3×3×3 mm$^3$) of the gastric cancer in the right flank via 20-gauge trocar needle.

When average tumor size reached ~200 mm$^3$, animals were assigned into 7 groups with 8 mice per group using a stratified randomization procedure. Mice were then treated twice daily (BID) with vehicle (0.5% methylcellulose), 12 mg/kg Compound A, or once every four days (Q4D) with 15 mg/kg paclitaxel (30 mg/5 ml, diluted to 1.5 mg/ml with saline just before use), Beijing Union Pharmaceutical Factory), or the combination of paclitaxel (15 mg/kg) and Compound A (6 or 12 mg/kg BID). All doses were based on free-base weight. Treatments were administered by oral gavage (p.o.) for vehicle and Compound A or intraperitoneal (i.p.) for paclitaxel in a volume of 10 ml/kg body weight. Body weight was assessed immediately before dosing and volume dosed was adjusted accordingly.

Individual body weight and tumor volume were recorded twice weekly, with mice being monitored daily for clinical signs of toxicity for the duration of the study. Mice were euthanized using carbon dioxide once their tumor volume reached ≥2,000 mm$^3$, the tumor was ulcerated, or body weight loss exceeded 25%.

After implantation, primary tumor volume was measured in two dimensions using a calliper. Tumor volume was calculated using the formula: V=0.5×(a×b$^2$) where a and b are the long and short diameters of the tumor, respectively. Tumor growth inhibition (TGI) was calculated using the following formula:

$$\% \text{ growth inhibition} = 100\% \times \left(1 - \left(\frac{(\text{treated } t) - (\text{treated } t_0)}{(\text{placebo } t) - (\text{placebo } t_0)}\right)\right) \quad (1)$$

treated $t$ = treated tumor volume at time t treated $t_0$ = treated tumor volume at time 0 placebo $t$ = placebo tumor volume at time t placebo $t_0$ = placebo tumor volume at time 0

Statistical analysis was conducted using the student T-test. P<0.05 was considered statistically significant.

Figure 5:
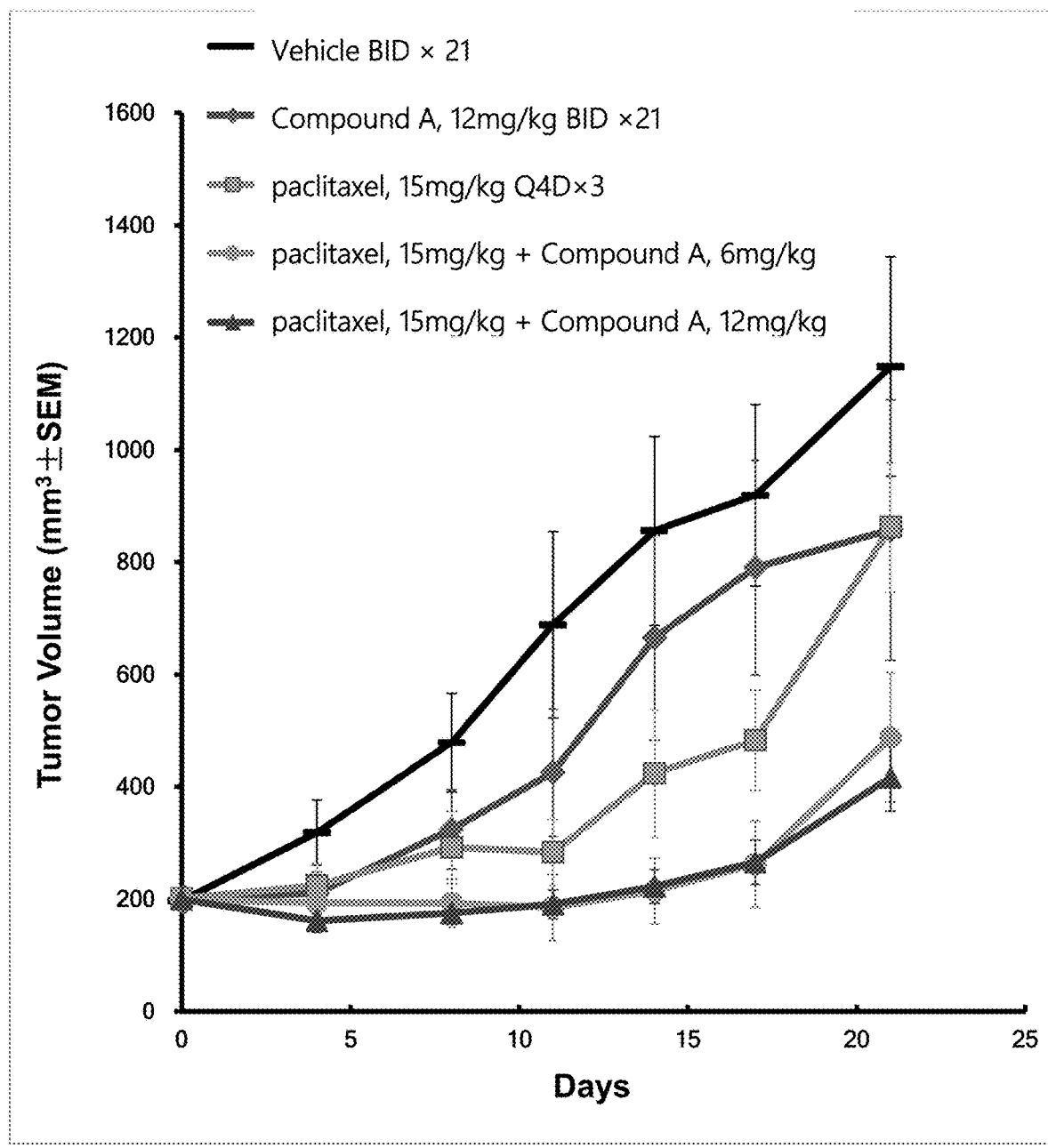
FIG. 5 shows the effect of Compound A, paclitaxel and (Compound A+paclitaxel) on tumor growth in human primary gastric cancer xenograft model.
Figure 6:
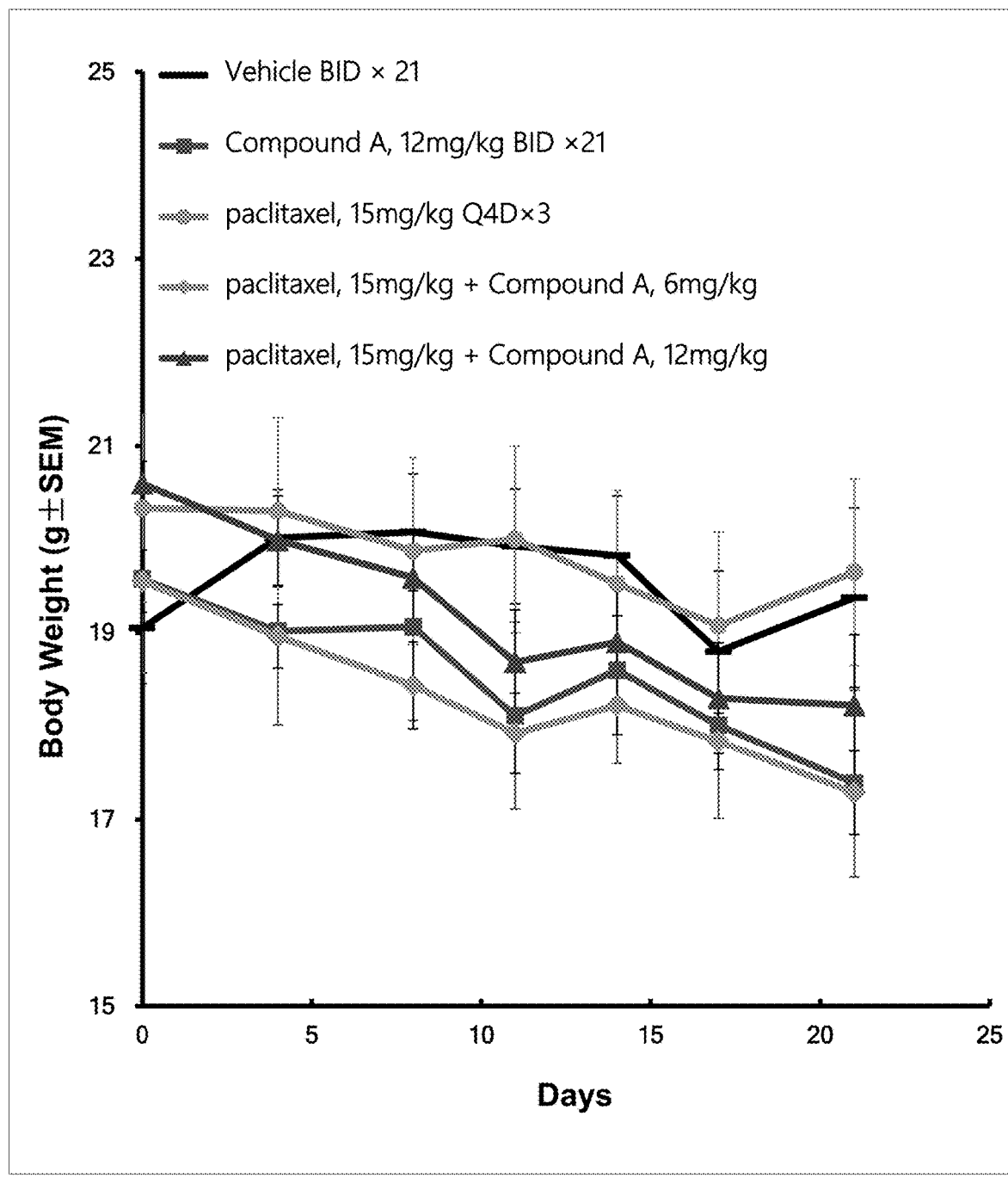
FIG. 6 shows the effect of Compound A, paclitaxel and (Compound A+paclitaxel) on body weight in primary human gastric cancer xenograft model.

Result:

In vivo anti-tumor efficacy of the combination of Compound A and paclitaxel was shown in FIGS. 5 and 6. Single agent treatments, paclitaxel (15 mg/kg Q4D×3), and Compound A (12 mg/kg BID) had weak or no effect on tumor growth, with 31%, −29% and 30% of tumor growth inhibition (TGI) on day 21, respectively (not statistically different from vehicle group). All combination treatments, paclitaxel with Compound A (6 and 12 mg/kg BID) showed significantly better anti-tumor activity, with 80%, 70% and 77% of TGI on day 21, respectively (p<0.05 vs. paclitaxel single agent treatment). In all single agent and combination treatment groups, no significant effect on body weight was observed throughout the study compared to the vehicle group. Compound A also demonstrated better anti-tumor activity in combination with paclitaxel than paclitaxel single agent in a primary gastric cancer xenograft model, without severe toxicity.

Example 4 Effect of the Combination of PARP Inhibitor and Etoposide/carboplatin (E/C) in a Primary Human SCLC Tumor Xenograft Model Method Tumor tissues surgically removed from a patient with limited-stage small cell lung cancer (SCLC). Within 2 to 4 hours following patient biopsy, the tumor samples were subcutaneously engrafted into the scapular area of anesthetized NOD/SCID mice. After tumors grew to around 300-1000 mm$^3$, tumors were surgically removed and fragments were passaged in NOD/SCID mice by subsequent engraftments. Engraftment in BALB/c nude mice was conducted after 3 successfully passages in NOD/SCID mice. The right axilla region of each BALB/C nude mouse was cleaned with 70% ethanol prior to tumor fragments inoculation. Each animal was implanted subcutaneously with a fragment (around 3×3×3 mm$^3$) of the lung cancer in the right flank via 20-gauge trocar needle.

When average tumor size reached ~230 mm$^3$, animals were assigned into 4 groups with 10 mice per group using a stratified randomization procedure. Mice were then treated with vehicle (0.5% methylcellulose) twice daily (BID) for 42 days, or etoposide (Adamas Reagent Co., Ltd. CAS #33419-44-0)/carboplatin (CAS #41575-94-4, from Beijing Fei Long Rui Co., Ltd.) [etoposide at 12 mg/kg (Day1-3)+ carboplatin at 60 mg/kg (Day1) of a 7 day cycle] for 3 cycles then vehicle BID for 21 days (Day22-42), or the combination of E/C with Compound B at 1.36 mg/kg BID [Day1-7 (continuous) or Day1-4(intermittent) of the 7 day cycle] for 3 cycles then Compound B maintenance therapy at 5.45 mg/kg BID for 21 days (Day22-42). All doses were based on free-base weight. Treatments were administered by oral gavage (p.o.) for vehicle and Compound B or intraperitoneal (ip) for etoposide, or intravenous for carboplatin in a volume of 10 ml/kg body weight. Body weight was assessed immediately before dosing and volume dosed was adjusted accordingly.

Individual body weight and tumor volume were recorded twice weekly from Day1-31 and then once weekly thereafter, with mice being monitored daily for clinical signs of toxicity for the duration of the study. Mice were euthanized using carbon dioxide once their tumor volume reached ≥2000 mm$^3$ or the tumor was ulcerated.

After implantation, primary tumor volume was measured in two dimensions using a caliper. Tumor volume was calculated using the formula: V=0.5× (a×b$^2$) where a and b are the long and short diameters of the tumor, respectively. Partial regression (PR) was defined as tumor volume smaller than 50% of the starting tumor volume on the first day of dosing in three consecutive measurements and complete regression (CR) was defined as tumor volume less than 14 mm$^3$ in three consecutive measurements. In animal with PR tumor, progressive disease was defined as tumor volume bigger than 50% of the starting tumor volume in two consecutive measurements. In animal with CR tumor, progressive disease was defined as tumor volume bigger than 14 mm$^3$ in two consecutive measurements. Tumor free was defined as tumor volume less than 14 mm$^3$ on the day 72 of end of the study.

Tumor growth inhibition (TGI) was calculated using the following formula:

$$\% \text{ growth inhibition} = 100\% \times \left(1 - \left(\frac{(\text{treated } t) - (\text{treated } t_0)}{(\text{placebo } t) - (\text{placebo } t_0)}\right)\right) \quad (2)$$

treated $t$ = treated tumor volume at time t treated $t_0$ = treated tumor volume at time 0 placebo $t$ = placebo tumor volume at time t placebo $t_0$ = placebo tumor volume at time 0

Figure 7:
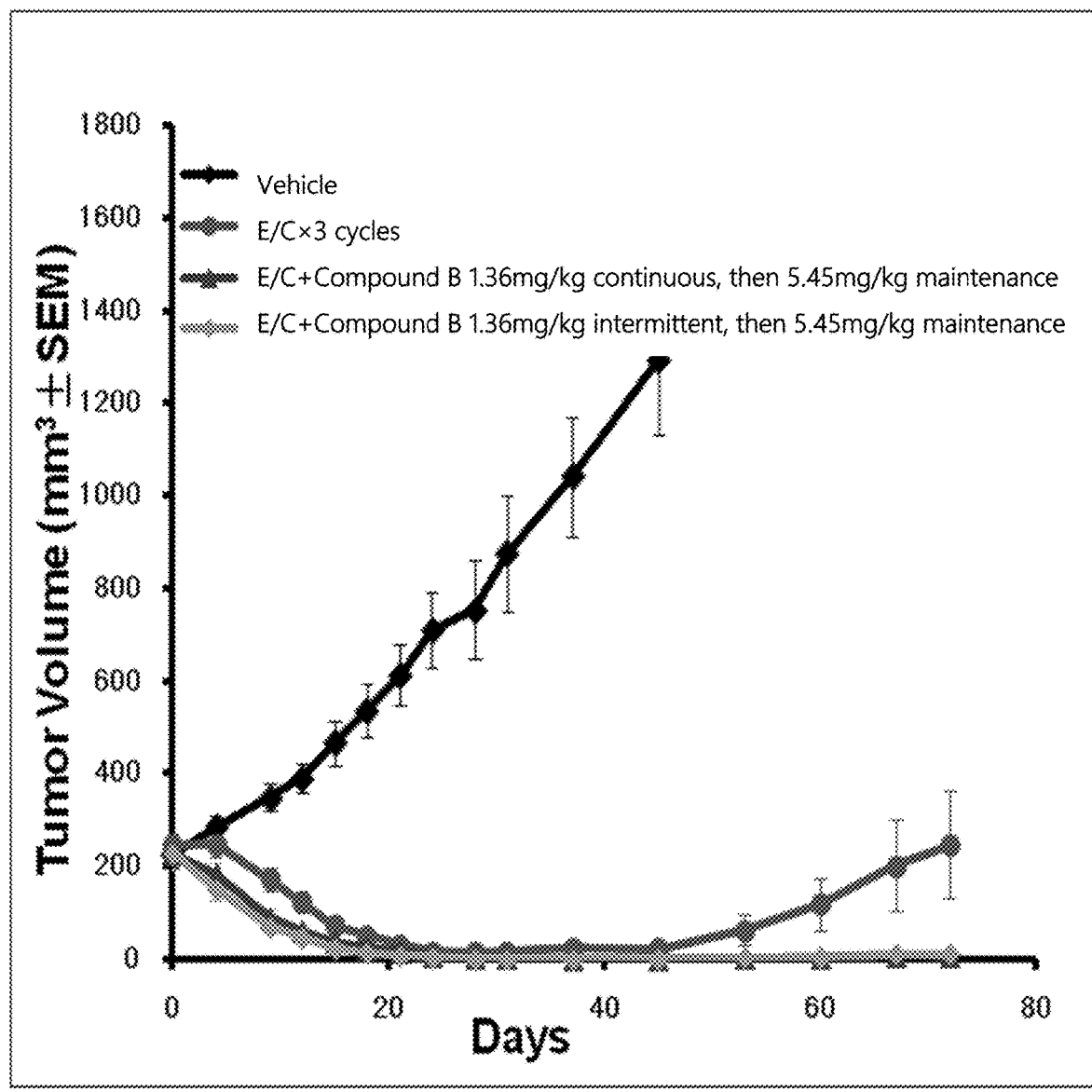
FIG. 7 shows the effect of etoposide and carboplatin (E/C), and Compound B in combination with E/C on tumor growth in primary human SCLC (limited-stage) xenograft model.
Figure 8:
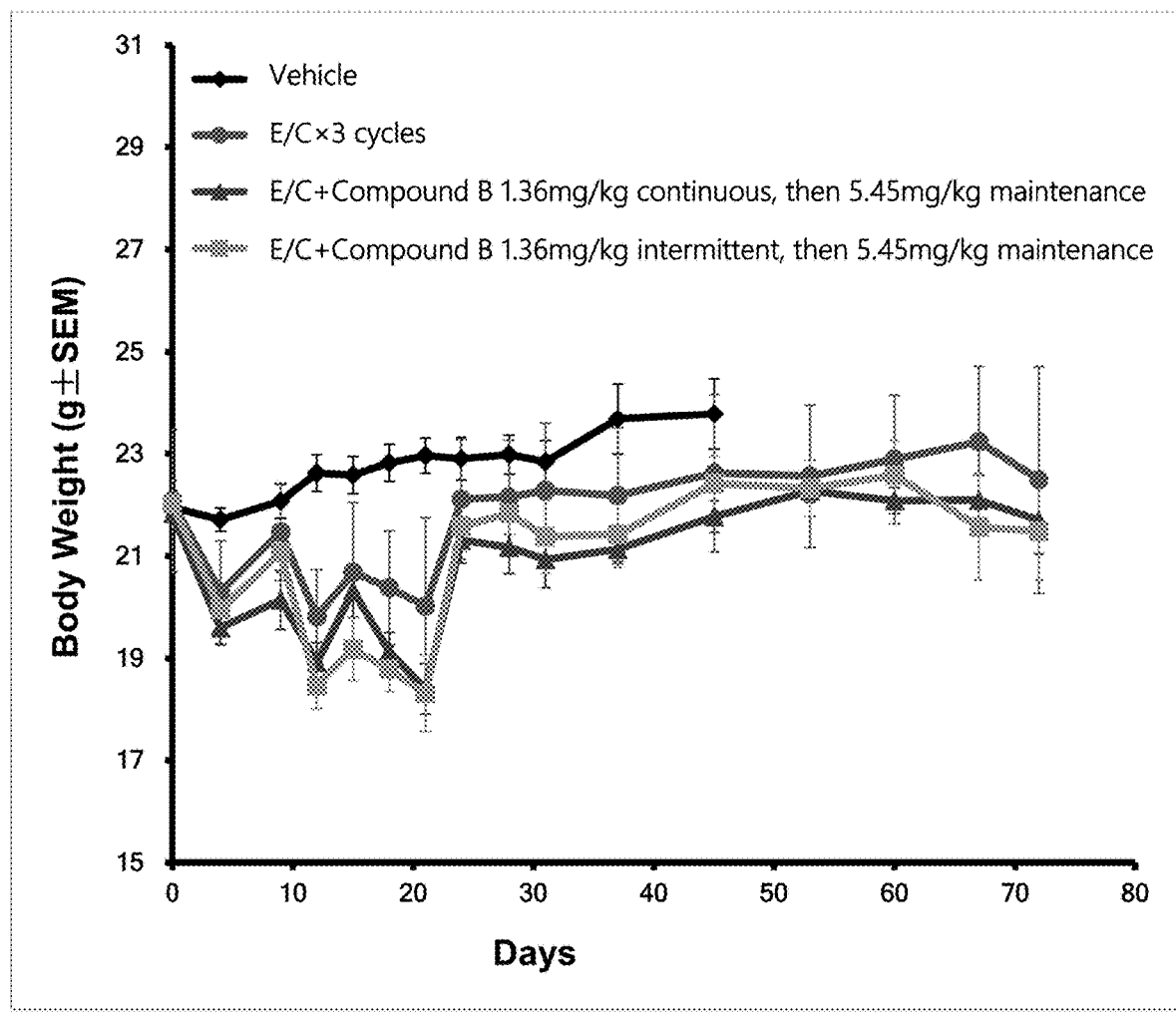
FIG. 8 shows the effect of etoposide and carboplatin (E/C), and Compound B in combination with E/C on body weight in primary human SCLC (limited-stage) xenograft model.
Figure 9:
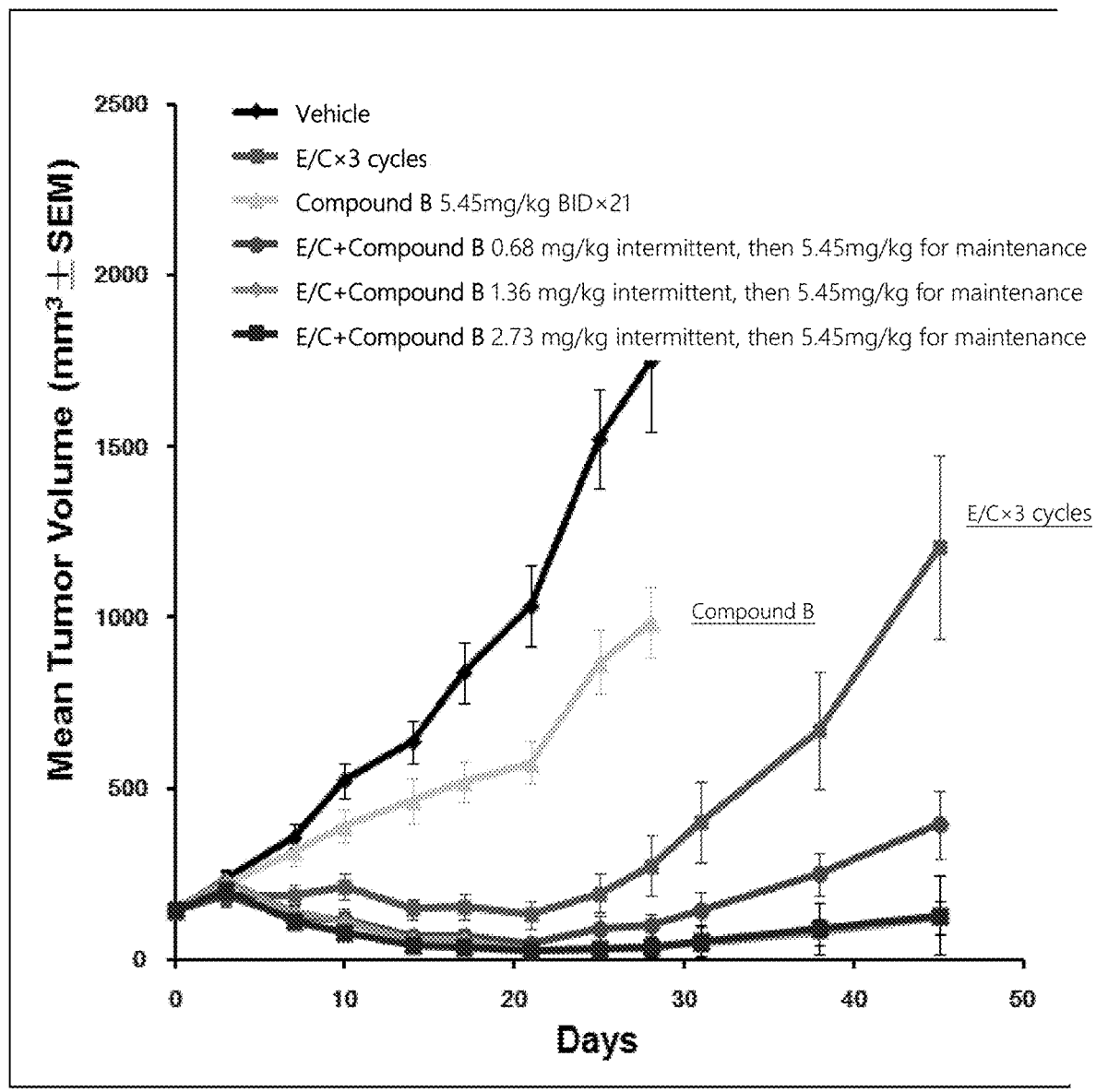
FIG. 9 shows the effect of Compound B, etoposide and carboplatin (E/C), and Compound B in combination with E/C on tumor growth in primary human SCLC (extensive-stage) xenograft model.
Figure 10:
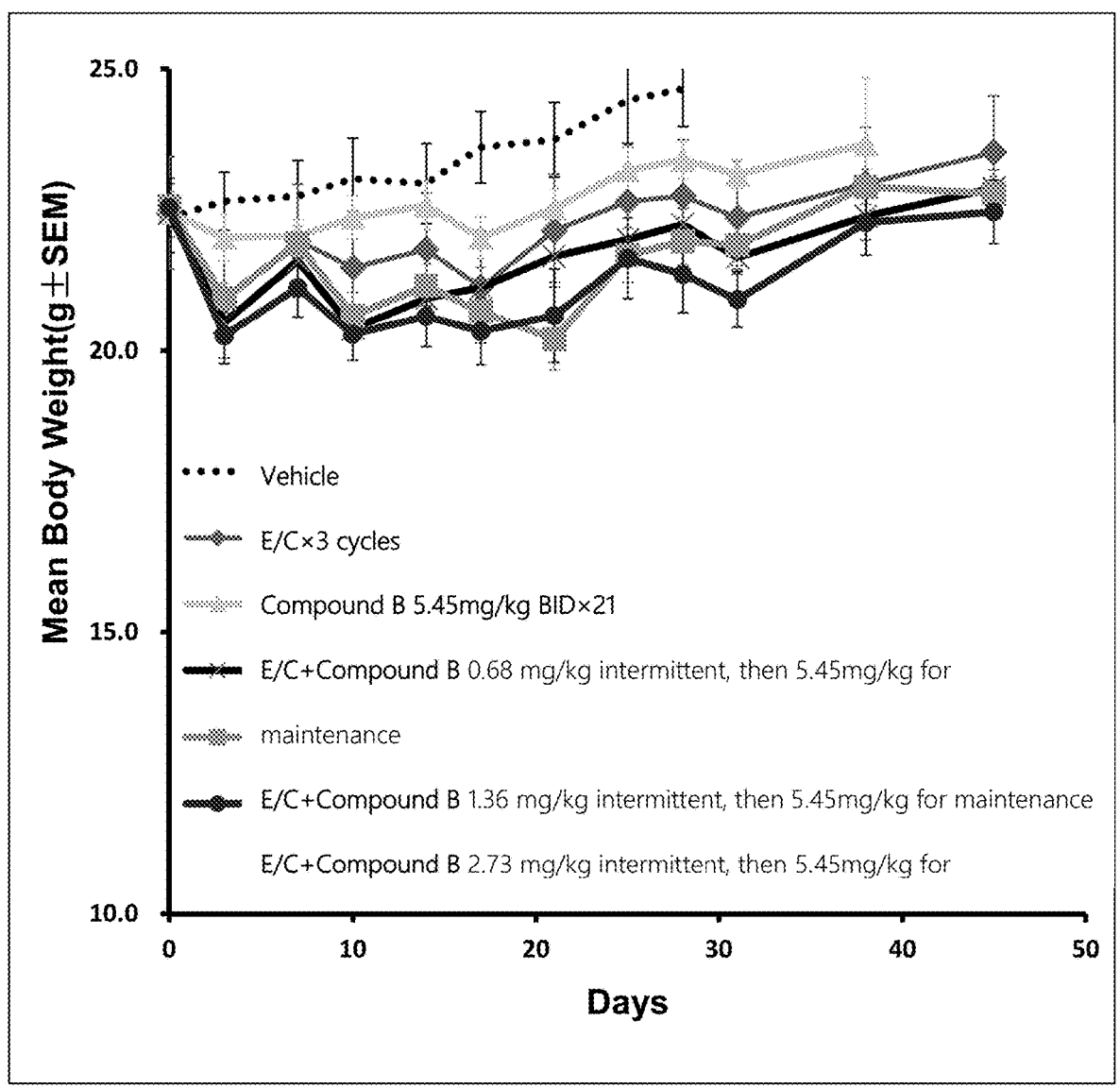
FIG. 10 shows the effect of Compound B, etoposide and carboplatin (E/C), and Compound B on body weight in primary human SCLC (extensive-stage) xenograft model.
Figure 11:
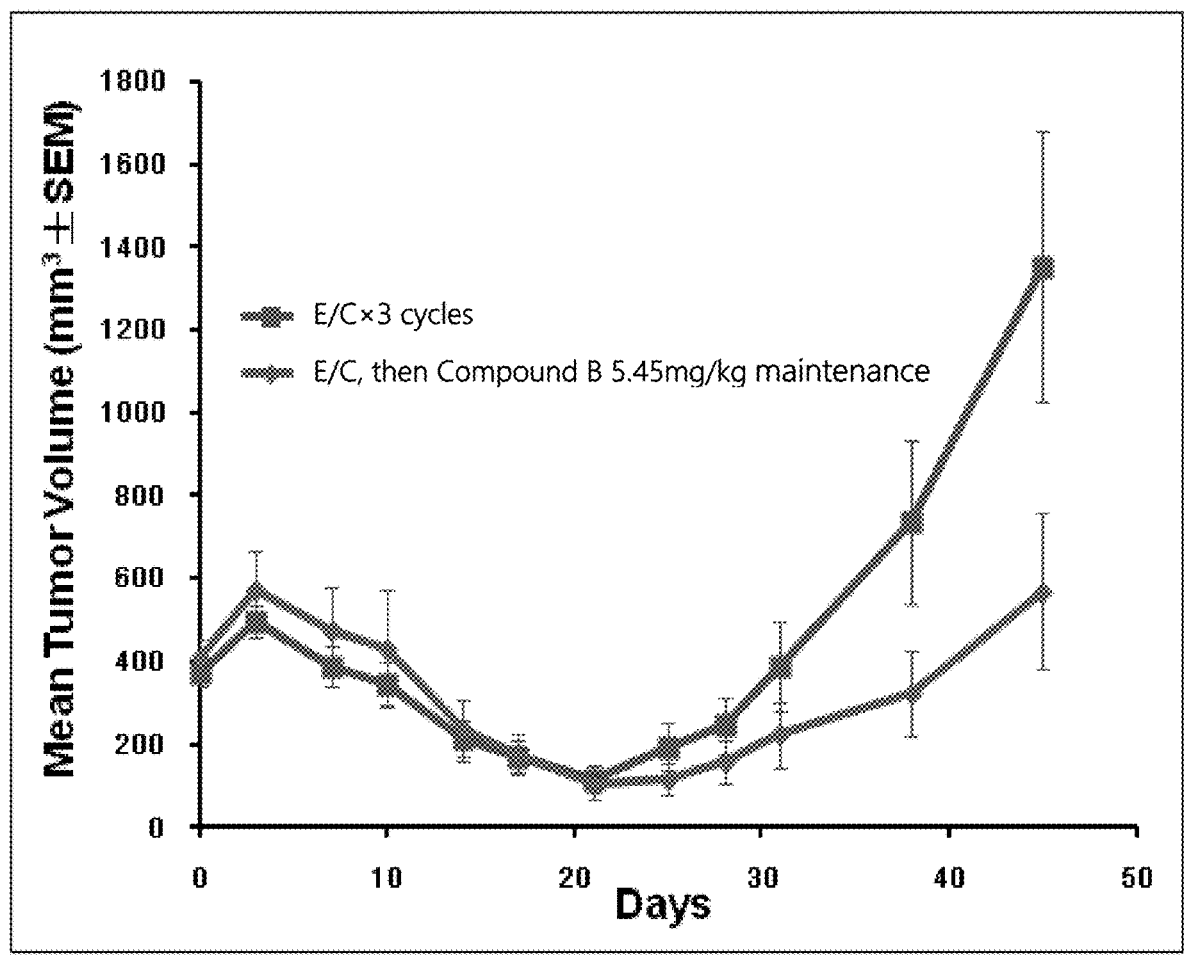
FIG. 11 shows the effect of Compound B as maintenance therapy after E/C on tumor growth in primary human SCLC (extensive-stage) xenograft model.
Figure 12:
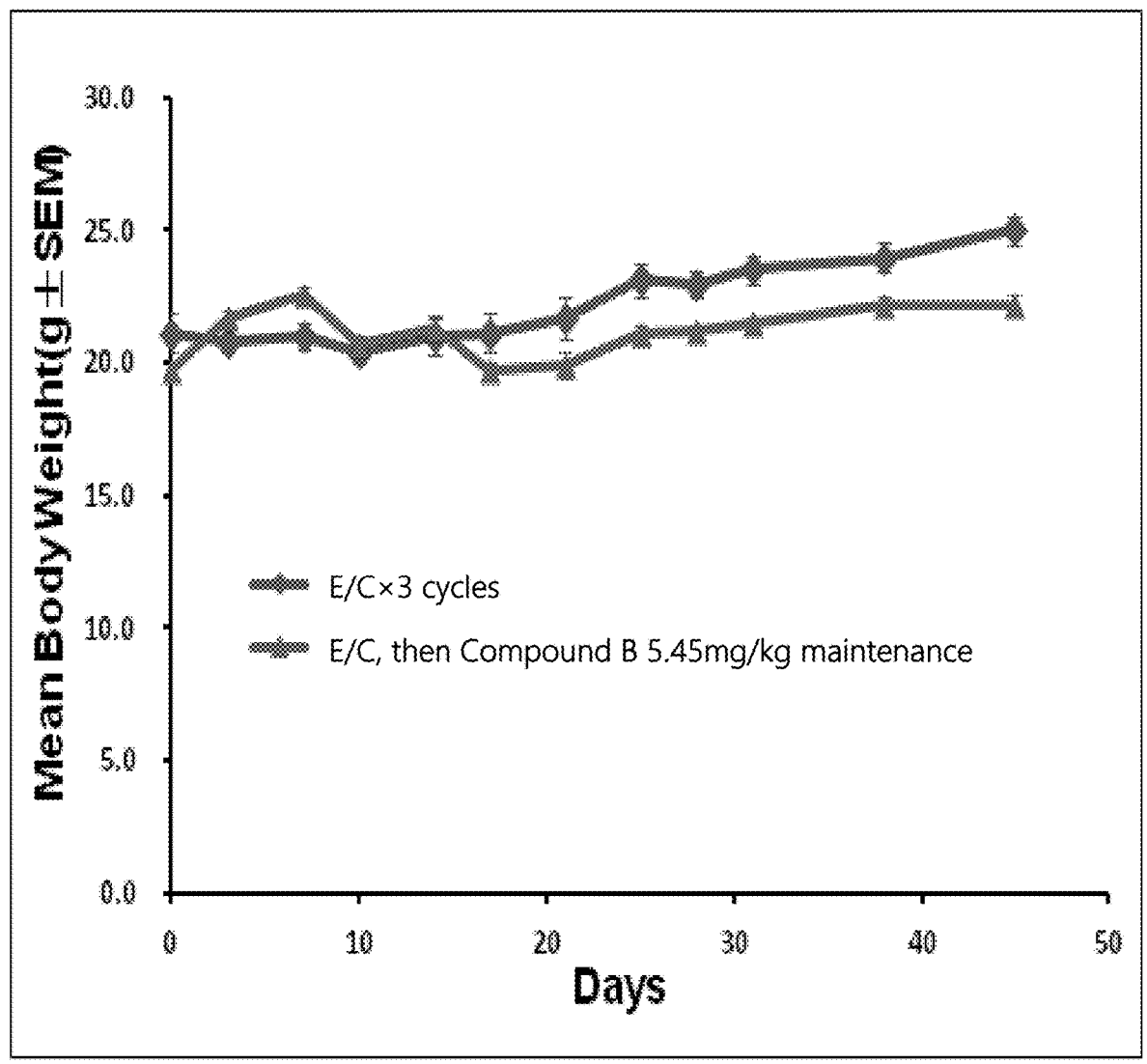
FIG. 12 shows the effect of Compound B as maintenance therapy after E/C on body weight in primary human SCLC (extensive-stage) xenograft model.

Statistical analysis was conducted using the student T-test. P<0.05 was considered statistically significant.
Result:
In vivo anti-tumor efficacy of the combination of Compound B and E/C was shown in FIGS. 7 and 8. Consistent with the clinical finding, PR was observed in the host patient after etoposide/carboplatin treatment, E/C for 3 cycles resulted in objective response in all animals treated (6PR/4CR/10). However, 7 of these 10 tumors had progressive disease after discontinuation of E/C treatment and mean tumor volume reached 246 mm$^3$ on day 72. Addition of Compound B at 1.36 mg/kg BID continuously (Day1-7) or intermittently (Day1-4) during the E/C treatment cycles and 5.45 mg/kg BID as maintenance therapy significantly enhanced anti-tumor activity with all animals becoming tumor free during the treatment (100% CRR). No relapse occurred while animals were on Compound B maintenance therapy, suggesting maintenance therapy with Compound B may provide further anti-tumor benefit. Thirty days after completion of maintenance treatment (day 72), most animals were still tumor-free. In all combination treatment groups, no significant effect on body weight was observed during the E/C concurrent administration phase compared to the E/C treatment group. During the maintenance phase, there was no significant body weight change in all treatment groups. Combination treatment of Compound B and E/C demonstrated better anti-tumor activity than E/C treatment alone, without severe toxicity.

Example 5 Effect of the Combination of PARP Inhibitor and E/C in a Primary Human SCLC Xenograft Model Method
Tumor tissues surgically removed from a patient with extensive-stage SCLC. Within 2 to 4 hours following patient biopsy, the tumor samples were subcutaneously engrafted into the scapular area of anesthetized NOD/SCID mice. After tumors grew to around 300-1000 mm$^3$, tumors were surgically removed and fragments were passaged in NOD/SCID mice by subsequent engraftments. Engraftment in BALB/c nude mice was conducted after 3 successfully passages in NOD/SCID mice. The right axilla region of each BALB/C nude mouse was cleaned with 70% ethanol prior to tumor fragments inoculation. Each animal was implanted subcutaneously with a fragment (around 3×3×3 mm$^3$) of the lung cancer in the right flank via 20-gauge trocar needle.

47 days after implantation, animals bearing tumor were divided to two cohorts, cohort 1used smaller tumors for combination setting and cohort 2 used bigger tumors for maintenance setting. In cohort1, animals with mean tumor size of ~150 mm$^3$ were assigned into 6 groups with 9 mice per group using a stratified randomization procedure. Mice were then treated with vehicle (0.5% methylcellulose) twice daily (BID) or Compound B at 5.45 mg/kg BID for 21 days, or E/C [etoposide at 12 mg/kg (Day1-3)+carboplatin at 60 mg/kg (Day1) of a 7 day cycle] for 3 cycles then vehicle BID for 21 days (Day22-42), or the combination of E/C with Compound B at 0.68, 1.36 or 2.73 mg/kg BID (Day1-4 of the 7 day cycle) for 3 cycles then Compound B maintenance therapy at 5.45 mg/kg BID for 21 days (Day22-42). In cohort2, animals with mean tumor size of ~400 mm$^3$ were treated with E/C for 3 cycles first. At day22, 20 animals were assigned into 2 groups with 10 mice per group using a stratified randomization procedure, then treated with vehicle (0.5% methylcellulose) twice daily (BID) for 21 days (Day22-42), or Compound B maintenance therapy at 5.45 mg/kg BID for 21 days (Day22-42). All doses were based on free-base weight. Treatments were administered by oral gavage (p.o.) for vehicle and Compound B, or intraperitoneal (ip) for etoposide, or intravenous for carboplatin in a volume of 10 ml/kg body weight. Body weight was assessed immediately before dosing and volume dosed was adjusted accordingly.

Individual body weight and tumor volume were recorded twice weekly from Day1-31 and then once weekly thereafter, with mice being monitored daily for clinical signs of toxicity for the duration of the study. Mice were euthanized using carbon dioxide once their tumor volume reached ≤2000 mm$^3$ or the tumor was ulcerated.

After implantation, primary tumor volume was measured in two dimensions using a caliper. Tumor volume was calculated using the formula: $V=0.5 \times (a \times b^2)$ where a and b are the long and short diameters of the tumor, respectively. Partial regression (PR) was defined as tumor volume smaller than 50% of the starting tumor volume on the first day of dosing in three consecutive measurements and complete regression (CR) was defined as tumor volume less than 14 mm$^3$ in three consecutive measurements. In animal with PR tumor, progressive disease was defined as tumor volume bigger than 50% of the starting tumor volume in two consecutive measurements. In animal with CR tumor, progressive disease was defined as tumor volume bigger than 14 mm$^3$ in two consecutive measurements. Tumor free was defined as tumor volume less than 14 mm$^3$ on the day 72 of end of the study.

Tumor growth inhibition (TGI) was calculated using the following formula:

$$\% \text{ growth inhibition} = 100\% \times \left(1 - \left(\frac{(\text{treated } t) - (\text{treated } t_0)}{(\text{placebo } t) - (\text{placebo } t_0)}\right)\right) \quad (3)$$

treated $t$ = treated tumor volume at time t treated $t_0$ = treated tumor volume at time 0 placebo $t$ = placebo tumor volume at time t placebo $t_0$ = placebo tumor volume at time 0

Statistical analysis was conducted using the student T-test. P<0.05 was considered statistically significant.
Result:
In vivo anti-tumor efficacy of the combination of Compound B and E/C was shown in FIGS. 9, 10, 11 and 12. Consistent with the clinical finding, PR was observed in the host patient after etoposide/carboplatin treatment but relapse was rapidly, E/C treatment resulted in objective response in both cohorts but tumors progressed after discontinuation of E/C treatment. In cohort1, E/C for 3 cycles resulted in objective response in animals treated (3PR/0CR/9) but the mean tumor volume rebounded to 1206 mm$^3$ on day 45. Addition of Compound B at 0.68, 1.36 or 2.73 mg/kg BID (Day 1-4) during the E/C treatment cycles, followed with 5.45 mg/kg BID as maintenance therapy, significantly enhanced anti-tumor activity with tumor regression (5PR/9, 4PR/4CR/9 and 2PR/6CR/9, respectively). At the completion of maintenance treatment (day45), 6 out of 9 animals were still tumor-free in Compound B 2.73 mg/kg group. In all combination treatment groups, no significant effect on body weight was observed during the E/C concurrent administration phase and the maintenance phase compared to the E/C treatment group. In cohort2 at the completion of 3 cycles E/C treatment, animals were divided into 2 groups and treated with vehicle or Compound B 5.45 mg/kg BID for 21 days. In vehicle group, the mean tumor volume rebounded to 1353 mm$^3$ on day 45. However, the mean tumor volume only reached 571 mm$^3$ after treated with Compound B, which demonstrated more sustained tumor growth inhibition than E/C alone. During the maintenance phase, there was no significant body weight change compared to the E/C treatment group. Combination treatment of Compound B and E/C demonstrated better anti-tumor activity than E/C treatment alone, without severe toxicity. Compound B as maintenance therapy also demonstrated significant anti-tumor activity.

Example 6 Clinical Trials of Compound B in Combination with Mab 1

Using Compound B to prepare capsules, a Phase Ia clinical safety study of Compound B combined with Mab 1 was completed on 43 subjects administered the doses of 10, 20, 40 and 60 mg BID of Compound B together with 2 mpk (mg/kg) or 200 mg Q3W. The results showed that all the combinations were safe and well tolerated.

The detailed study was illustrated as follows: Cohorts of 6 to 12 patients each received treatments at five planned dose levels (DLs). Mab 1 was administered at 2 mg/kg every three weeks (Q3W) with Compound B at 20, 40, or 60 mg twice daily (BID) in DLs 1, 2, and 3, respectively. Mab 1 was also administered at a fixed dose of 200 mg Q3W with Compound B at 40 or 60 mg BID in DLs 4 and 5, respectively.

Duration of treatment was greater than 200 days for 10 patients, and a total of seven patients remained on treatment as of the data cut-off (Mar. 31, 2017). The safety analysis suggested that the combination of Mab 1 and Compound B was generally well-tolerated in patients with advanced solid tumors, although dose-limiting toxicities occurred in three patients including nausea or vomiting at DL4 or DL5 or autoimmune hepatitis at DL5. However, no fatal adverse events have been reported and all events were reversible with or without corticosteroid treatment.

Co-administration of Mab-1 with Compound B did not have a significant impact on the pharmacokinetic profile of either compound. Either complete response or partial response were observed in patients with ovarian or fallopian tube cancer, patients with breast cancer, patients with pancreatic cancer, patients with uterine cancer; and those responses were durable and observed in patients with wild type and mutant gBRCA status. Stable diseases were observed in patients with prostate cancer and patients with bile duct cancer. Additional tumor types enrolled in the study include bladder, cervical, lung, and peripheral nerve sheath cancer.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

The invention claimed is:
1. A method for the delay of progression or treatment of cancer in a subject, wherein the cancer is selected from the group consisting of colorectal cancer, gastric cancer, lung cancer, small cell lung cancer, bladder cancer, breast cancer, ovarian cancer, fallopian tube carcinoma, cervical cancer, peritoneal carcinoma, prostate cancer, castration-resistant prostate, bile duct cancer, gastric/gastro-esophageal junction cancer, urothelial cancer, pancreatic cancer, peripheral nerve sheath cancer, uterine cancer, and melanoma, the method comprising administering to the subject in need thereof a therapeutically effective amount of a PARP inhibitor, in combination with a therapeutically effective amount of an immune checkpoint inhibitor, or a chemotherapeutic agent, wherein the PARP inhibitor is a compound of Formula (I),

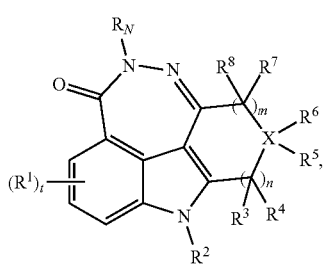

a stereoisomer thereof, or a pharmaceutically acceptable salts thereof, or a compound of Formula (III),

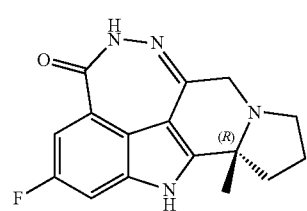

a pharmaceutically acceptable salt thereof, or a compound of Formula (IV),

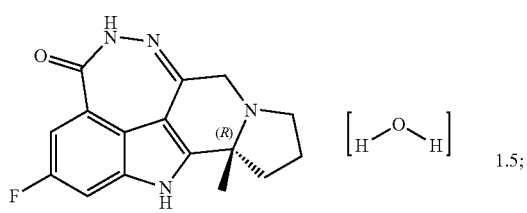

wherein:
$R_N$ is selected from the group consisting of hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

X is selected from the group consisting of C, N, O, and S;
m and n, which may be the same or different, are each an integer of 0, 1, 2, or 3;

t is an integer of 0, 1, 2, or 3;
$R^1$, at each occurrence, is independently selected from the group consisting of halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^2$ is selected from the group consisting of hydrogen, $COR^9$, $CONR^9R^{10}$, $CO_2R^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^6$, $R^7$ and $R^8$, which may be the same or different, are each independently selected from the group consisting of hydrogen, halogen, —$NR^9R^{10}$, —$OR^9$, oxo, —$COR^9$, —$CO_2R^9$, —$CONR^9R^{10}$, —$NR^9CONR^{10}R^{11}$, $NR^9CO_2R^{10}$, —$NR^9SO_2R^{10}$, —$SO_2R^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) they are attached, form a 3- to 8-membered saturated, partially or fully unsaturated ring having 0, 1 or 2 heteroatoms independently selected from the group consisting —$NR^{13}$—, —O—, —S—, —SO— and —$SO_2$—, and said ring is optionally substituted with at least one substituent $R^{12}$, provided that
when X is O, $R^5$ and $R^6$ are absent,
when X is N, $R^6$ is absent,
when X is S, $R^5$ and $R^6$ are absent, or at least one of $R^5$ and $R^6$ is oxo,
when one of $R^3$ and $R^4$ is oxo, the other is absent,
when one of $R^7$ and $R^8$ is oxo, the other is absent, and
when X is C and one of $R^5$ and $R^6$ is oxo, the other is absent;

$R^9$, $R^{10}$, and $R^{11}$, which may be the same or different, are each selected from the group consisting of hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^{12}$ is selected from the group consisting of CN, halogen, haloalkyl, $NO_2$, —NR'R'', —OR', oxo, —COR', —$CO_2R'$, —CONR'R'', —NR'CONR''R''', —$NR'CO_2R''$, —$NR'SO_2R''$, —$SO_2R'$, alkyl, alkenyl, alkynyl, cycloalkyl, heterocyclyl, aryl, and heteroaryl, wherein R', R'', and R''' are independently selected from the group consisting of hydrogen, haloalkyl, alkyl, arylalkyl, alkenyl, alkynyl, cycloalkyl, heterocyclyl, aryl, and heteroaryl, or (R' and R''), and/or (R'' and R''') together with the atoms to which they are attached, form a 3- to 8-membered saturated, partially or fully unsaturated ring having 0, 1 or 2 additional heteroatoms independently selected from the group consisting of —$NR^{13}$—, —O—, —S—, —SO— and —$SO_2$—, $R^{13}$ is selected from the group consisting of hydrogen, alkyl, cycloalkyl, aryl, heteroaryl, and heterocyclyl,
and wherein the immune checkpoint inhibitor is an antibody or fragment thereof that specifically binds to human PD-1, wherein the antibody or fragment thereof comprises a heavy chain variable region (Vh) and a light chain variable region (Vl), wherein the Vh comprises SEQ ID NO: 31(CDR1-H1), SEQ ID NO: 32(CDR2-H2), and SEQ ID NO: 33(CDR3-H3) respectively; and the Vl comprises SEQ ID NO: 34(CDR1-L1), SEQ ID NO: 35(CDR2-L2), and SEQ ID NO: 36(CDR3-L3), respectively;

and wherein the chemotherapeutic agent is paclitaxel or etopside plus carboplatin (E/C).

2. The method of claim 1, wherein the antibody that specifically binds to human PD-1 is a monoclonal antibody.

3. The method of claim 1, wherein the antibody or fragment thereof comprises a heavy chain variable region (Vh) amino acid sequence of SEQ ID No 24, and a light chain variable region (Vl) amino acid sequence of SEQ ID No 26.

4. The method of claim 1, wherein the cancer is selected from the group consisting of colorectal cancer, gastric cancer, lung cancer, small cell lung cancer, breast cancer, and ovarian cancer.

5. The method of claim 1, wherein the PARP inhibitor is the compound of Formula (III),

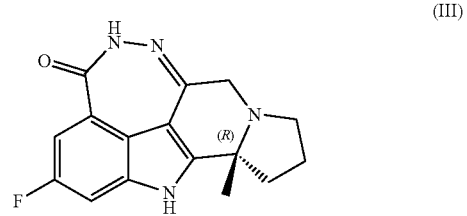

or a pharmaceutically acceptable salt thereof.

6. The method of claim 1, wherein the PARP inhibitor is the compound of Formula (IV),

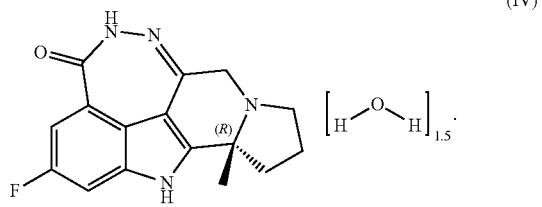

7. The method of claim 1, wherein the immune checkpoint inhibitor and the PARP inhibitor are administered simultaneously, sequentially or separately.

8. The method of claim 1, wherein the PARP inhibitor is administrated orally at a dose of 1-120 mg twice daily.

9. The method of claim 1, wherein the PARP inhibitor is administrated orally at a dose of 120-240 mg once a day.

10. The method of claim 1, wherein the immune checkpoint inhibitor is administered parenterally at a dose of 0.5-10 mg/kg once weekly, or every two weeks, or every three weeks, or every four weeks.

11. The method of claim 1, wherein the immune checkpoint inhibitor is administrated at a dose of 2 mg/kg every three weeks.

12. The method of claim 1, wherein the immune checkpoint inhibitor is administrated at a dose of 2 mg/kg every three weeks (Q3W), and the PARP inhibitor is administrated at a dose of 20 mg, 40 mg or 60 mg twice daily.

13. The method of claim 1, wherein the immune checkpoint inhibitor is administrated at a dose of 200 mg every three weeks, and the PARP inhibitor is administrated at a dose of 40 or 60 mg twice daily.

14. The method of claim 1, wherein the immune checkpoint inhibitor is an anti-PD-1 antibody.

15. The method of claim 1, wherein the wherein the antibody is a monoclonal antibody comprising a heavy chain variable region (Vh) amino acid sequence of SEQ ID No 24, a light chain variable region (Vl) amino acid sequence of SEQ ID No 26, and a IgG4 constant domain amino acid sequence of SEQ ID NO 88.

16. A pharmaceutical combination for use in the delay of progression or treatment of cancer, wherein the cancer is selected from the group consisting of colorectal cancer, gastric cancer, lung cancer, small cell lung cancer, bladder cancer, breast cancer, ovarian cancer, fallopian tube carcinoma, cervical cancer, peritoneal carcinoma, prostate cancer, castration-resistant prostate, bile duct cancer, gastric/gastro-esophageal junction cancer, urothelial cancer, pancreatic cancer, peripheral nerve sheath cancer, uterine cancer, and melanoma, the pharmaceutical combination comprising a PARP inhibitor and a chemotherapeutic agent, wherein the chemotherapeutic agent is selected from the group consisting of paclitaxel and etoposide/carboplatin (E/C), and wherein the PARP inhibitor is a compound of Formula (I),

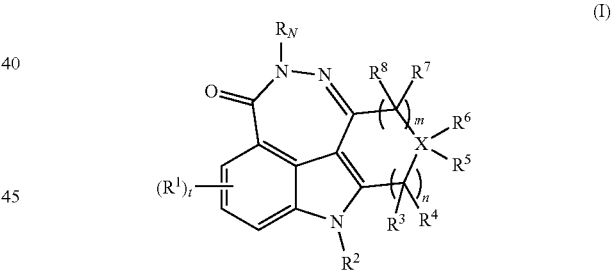

a stereoisomer thereof, or a pharmaceutically acceptable salts thereof, or a compound of Formula (III),

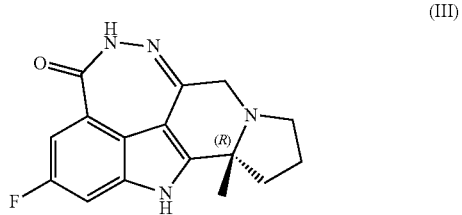

a pharmaceutically acceptable salt thereof or a compound of Formula (IV),

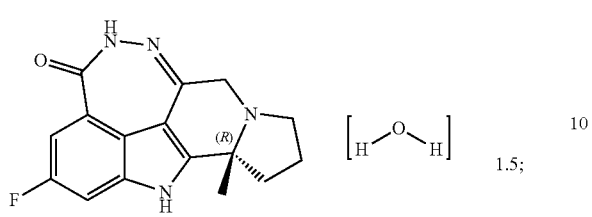

wherein:
$R_N$ is selected from the group consisting of hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

X is selected from the group consisting of C, N, O, and S;
m and n, which may be the same or different, are each an integer of 0, 1, 2, or 3;
t is an integer of 0, 1, 2, or 3;
$R^1$, at each occurrence, is independently selected from the group consisting of halogen, CN, $NO_2$, $OR^9$, $NR^9R^{10}$, $NR^9COR^{10}$, $NR^9SO_2R^{10}$, $CONR^9R^{10}$, $COOR^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^2$ is selected from the group consisting of hydrogen, $COR^9$, $CONR^9R^{10}$, $CO_2R^9$, $SO_2R^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^3$, $R^4$, $R^5$, $R^6$, $R^7$ and $R^8$, which may be the same or different, are each independently selected from the group consisting of hydrogen, halogen, —$NR^9R^{10}$, —$OR^9$, oxo, —$COR^9$, —$CO_2R^9$, —$CONR^9R^{10}$, —$NR^9CONR^{10}R^{11}$, —$NR^9CO_2R^{10}$, —$NR^9SO_2R^{10}$, —$SO_2R^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent $R^{12}$, or ($R^3$ and $R^4$), and/or ($R^4$ and $R^5$), and/or ($R^5$ and $R^6$), and/or ($R^6$ and $R^7$), and/or ($R^7$ and $R^8$), together with the atom(s) they are attached, form a 3- to 8-membered saturated, partially or fully unsaturated ring having 0, 1 or 2 heteroatoms independently selected from the group consisting of —$NR^{13}$—, —O—, —S—, —SO— and —$SO_2$—, and said ring is optionally substituted with at least one substituent $R^{12}$, provided that
when X is O, $R^5$ and $R^6$ are absent,
when X is N, $R^6$ is absent,
when X is S, $R^5$ and $R^6$ are absent, or at least one of $R^5$ and $R^6$ is oxo,
when one of $R^3$ and $R^4$ is oxo, the other is absent,
when one of $R^7$ and $R^8$ is oxo, the other is absent, and
when X is C and one of $R^5$ and $R^6$ is oxo, the other is absent;

$R^9$, $R^{10}$, and $R^{11}$, which may be the same or different, are each selected from the group consisting of hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent $R^{12}$;

$R^{12}$ is selected from the group consisting of CN, halogen, haloalkyl, $NO_2$, —NR'R'', —OR', oxo, —COR', —$CO_2R'$, —CONR'R'', —NR'CONR''R''', —$NR'CO_2R''$, —$NR'SO_2R''$, —$SO_2R'$, alkyl, alkenyl, alkynyl, cycloalkyl, heterocyclyl, aryl, and heteroaryl, wherein R', R'', and R''' are independently selected from the group consisting of hydrogen, haloalkyl, alkyl, arylalkyl, alkenyl, alkynyl, cycloalkyl, heterocyclyl, aryl, and heteroaryl, or (R' and R''), and/or (R'' and R''') together with the atoms to which they are attached, form a 3- to 8-membered saturated, partially or fully unsaturated ring having 0, 1 or 2 additional heteroatoms independently selected from the group consisting of —$NR^{13}$—, —O—, —S—, —SO— and —$SO_2$—, $R^{13}$ is selected from the group consisting of hydrogen, alkyl, cycloalkyl, aryl, heteroaryl, and heterocyclyl.

17. A pharmaceutical combination for use in the delay of progression or treatment of cancer, wherein the cancer is selected from the group consisting of colorectal cancer, gastric cancer, lung cancer, small cell lung cancer, bladder cancer, breast cancer, ovarian cancer, fallopian tube carcinoma, cervical cancer, peritoneal carcinoma, prostate cancer, castration-resistant prostate, bile duct cancer, gastric/gastro-esophageal junction cancer, urothelial cancer, pancreatic cancer, peripheral nerve sheath cancer, uterine cancer, and melanoma, the pharmaceutical combination comprising a PARP inhibitor, and an immune checkpoint inhibitor, wherein the PARP inhibitor is a compound of Formula (I),

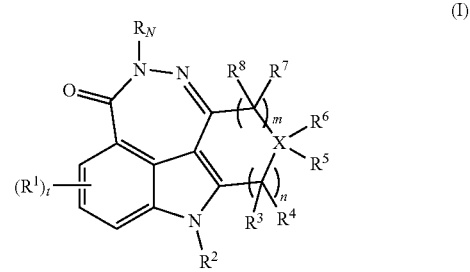

a stereoisomer thereof, or a pharmaceutically acceptable salts thereof, or a compound of Formula (III),

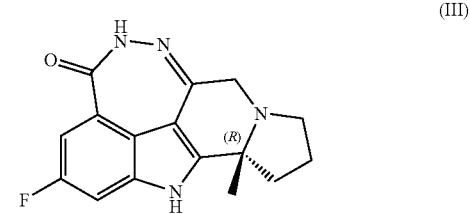

a pharmaceutically acceptable salt thereof, or a compound of Formula (IV),

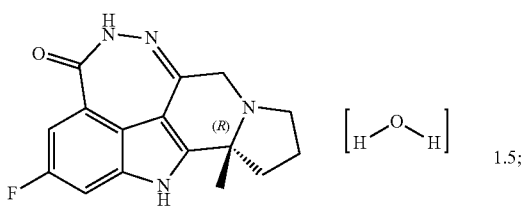

(IV)

wherein:
R$_N$ is selected from the group consisting of hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

X is selected from the group consisting of C, N, O, and S;
m and n, which may be the same or different, are each an integer of 0, 1, 2, or 3;
t is an integer of 0, 1, 2, or 3;
R$^1$, at each occurrence, is independently selected from the group consisting of halogen, CN, NO$_2$, OR$^9$, NR$^9$R$^{10}$, NR$^9$COR$^{10}$, NR$^9$SO$_2$R$^{10}$, CONR$^9$R$^{10}$, COOR$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

R$^2$ is selected from the group consisting of hydrogen, COR$^9$, CONR$^9$R$^{10}$, CO$_2$R$^9$, SO$_2$R$^9$, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

R$^3$, R$^4$, R$^5$, R$^6$, R$^7$ and R$^8$, which may be the same or different, are each independently selected from the group consisting of hydrogen, halogen, —NR$^9$R$^{10}$, —OR$^9$, oxo, —COR$^9$, —CO$_2$R$^9$, —CONR$^9$R$^{10}$, —NR$^9$CONR$^{10}$R$^{11}$, —NR$^9$CO$_2$R$^{10}$, —NR$^9$SO$_2$R$^{10}$, —SO$_2$R$^9$, alkyl, alkenyl, cycloalkyl, aryl, heterocyclyl, alkynyl, and heteroaryl, wherein each of the alkyl, alkenyl, alkynyl, cycloalkyl, aryl, heterocyclyl, and heteroaryl is independently optionally substituted with at least one substituent R$^{12}$, or (R$^3$ and R$^4$), and/or (R$^4$ and R$^5$), and/or (R$^5$ and R$^6$), and/or (R$^6$ and R$^7$), and/or (R$^7$ and R$^8$), together with the atom(s) they are attached, form a 3- to 8-membered saturated, partially or fully unsaturated ring having 0, 1 or 2 heteroatoms independently selected from the group consisting of —NR$^{13}$—, —O—, —S—, —SO— and —SO$_2$—, and said ring is optionally substituted with at least one substituent R$^{12}$, provided that
when X is O, R$^5$ and R$^6$ are absent,
when X is N, R$^6$ is absent,
when X is S, R$^5$ and R$^6$ are absent, or at least one of R$^5$ and R$^6$ is oxo,
when one of R$^3$ and R$^4$ is oxo, the other is absent,
when one of R$^7$ and R$^8$ is oxo, the other is absent, and
when X is C and one of R$^5$ and R$^6$ is oxo, the other is absent;

R$^9$, R$^{10}$, and R$^{11}$, which may be the same or different, are each selected from the group consisting of hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently optionally substituted with at least one substituent R$^{12}$;

R$^{12}$ is selected from the group consisting of CN, halogen, haloalkyl, NO$_2$, —NR'R", —OR', oxo, —COR', —CO$_2$R', —CONR'R", —NR'CONR"R'", —NR'CO$_2$R", —NR'SO$_2$R", —SO$_2$R', alkyl, alkenyl, alkynyl, cycloalkyl, heterocyclyl, aryl, and heteroaryl, wherein R', R", and R'" are independently selected from the group consisting of hydrogen, haloalkyl, alkyl, arylalkyl, alkenyl, alkynyl, cycloalkyl, heterocyclyl, aryl, and heteroaryl, or (R' and R"), and/or (R" and R'") together with the atoms to which they are attached, form a 3- to 8-membered saturated, partially or fully unsaturated ring having 0, 1 or 2 additional heteroatoms independently selected from the group consisting of —NR$^{13}$—, —O—, —S—, —SO— and —SO$_2$—, R$^{13}$ is selected from the group consisting of hydrogen, alkyl, cycloalkyl, aryl, heteroaryl, and heterocyclyl, and wherein the immune checkpoint inhibitor is an antibody or fragment thereof that specifically binds to human PD-1, wherein the antibody or fragment thereof comprises a heavy chain variable region (Vh) and a light chain variable region (Vl), wherein the Vh comprises SEQ ID NO: 31(CDR1-H1), SEQ ID NO: 32(CDR2-H2), and SEQ ID NO: 33(CDR3-H3) respectively; and the Vl comprises SEQ ID NO: 34(CDR1-L1), SEQ ID NO: 35(CDR2-L2), and SEQ ID NO: 36 (CDR3-L3), respectively.

18. The pharmaceutical combination of claim 17, wherein the antibody that specifically binds to human PD-1 is a monoclonal antibody.

19. The pharmaceutical combination of claim 18, wherein the antibody comprises a heavy chain variable region (Vh) amino acid sequence of SEQ ID No 24, a light chain variable region (Vl) amino acid sequence of SEQ ID No 26, and a IgG4 constant domain amino acid sequence of SEQ ID NO 88.

20. The pharmaceutical combination of claim 17, wherein the cancer is selected from the group consisting of colorectal cancer, gastric cancer, lung cancer, small cell lung cancer, breast cancer, and ovarian cancer.

21. The pharmaceutical combination of claim 17, wherein the PARP inhibitor is the compound of Formula (III),

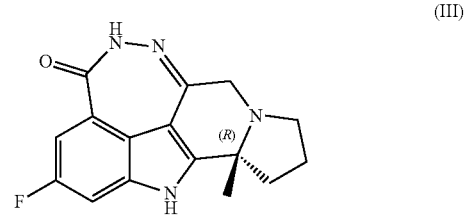

(III)

or a pharmaceutically acceptable salt thereof.

22. The pharmaceutical combination of claim 17, wherein the PARP inhibitor is the compound of Formula (IV),

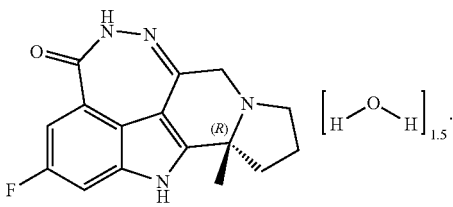

(IV)

23. The pharmaceutical combination of claim 16, wherein the immune checkpoint inhibitor and the PARP inhibitor are administered simultaneously, sequentially or separately.

24. The pharmaceutical combination of claim 17, wherein the PARP inhibitor is administered orally at a dose of 1-120 mg twice daily.

25. The pharmaceutical combination of claim 17, wherein the PARP inhibitor is administered orally at a dose of 1-80 mg twice daily.

26. The pharmaceutical combination of claim 17, wherein the anti-PD-1 antibody, which is administered parenterally at a dose of 0.5-10 mg/kg once weekly, or every two weeks, or every three weeks, or every four weeks.

27. The method of claim 1, wherein the PARP inhibitor is administrated orally at a dose of 1-80 mg twice daily.

28. The method of claim 1, wherein the PARP inhibitor is administrated orally at a dose of 60-120 mg once a day.

29. The pharmaceutical combination of claim 16, wherein the PARP inhibitor is the compound of Formula (IV),

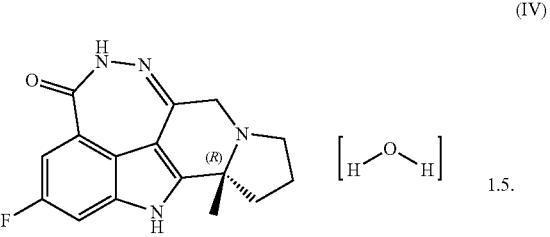

(IV)

* * * * *

SEQUENCE LISTING

```
<160> NUMBER OF SEQ ID NOS: 90

<210> SEQ ID NO 1
<211> LENGTH: 444
<212> TYPE: DNA
<213> ORGANISM: Homo sapiens

<400> SEQUENCE: 1
ccaggatggt tcttagactc cccagacagg ccctggaacc cccccacctt ctccccagcc      60
ctgctcgtgg tgaccgaagg ggacaacgcc accttcacct gcagcttctc caacacatcg     120
gagagcttcg tgctaaactg gtaccgcatg agccccagca accagacgga caagctggcc     180
gccttccccg aggaccgcag ccagcccggc caggactgcg gcttccgtgt cacacaactg     240
cccaacgggc gtgacttcca catgagcgtg gtcagggccc ggcgcaatga cagcggcacc     300
```

```
tacctctgtg gggccatctc cctggccccc aaggcgcaga tcaaagagag cctgcgggca    360
gagctcaggg tgacagagag aagggcagaa gtgcccacag cccaccccag cccctcaccc    420
aggccagccg gccagttcca aacc                                          444
```

```
<210> SEQ ID NO 2
<211> LENGTH: 148
<212> TYPE: PRT
<213> ORGANISM: Homo sapiens

<400> SEQUENCE: 2

Pro Gly Trp Phe Leu Asp Ser Pro Asp Arg Pro Trp Asn Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr
145
```

```
<210> SEQ ID NO 3
<211> LENGTH: 354
<212> TYPE: DNA
<213> ORGANISM: Mus musculus

<400> SEQUENCE: 3
caggtgcagc tgaaggagtc aggacctggc ctggtggcgc cctcaaagaa cctgtccatc     60
acttgcactg tctctgggtt ttcattaacc agctatggtg tacactggat tcgccagcct    120
ccaggaaagg gactggaatg gctgggagta atatgggccg gtggaagcac aaattataat    180
tcggctctca tgtccagact gagcatcagc aaagacaact ccaggagcca agtttttctta   240 agaatgaaca gtctgcaaac tgatgacaca gccatgtact actgtgccag agcctatggt    300
aactactggt acatcgatgt ctggggcgca gggaccacgg tcaccgtctc ctca          354
```

```
<210> SEQ ID NO 4
<211> LENGTH: 118
<212> TYPE: PRT
<213> ORGANISM: Mus musculus

<400> SEQUENCE: 4

Gln Val Gln Leu Lys Glu Ser Gly Pro Gly Leu Val Ala Pro Ser Lys
1               5                   10                  15

Asn Leu Ser Ile Thr Cys Thr Val Ser Gly Phe Ser Leu Thr Ser Tyr
            20                  25                  30
```

```
Gly Val His Trp Ile Arg Gln Pro Gly Lys Gly Leu Glu Trp Leu
            35                  40                  45

Gly Val Ile Trp Ala Gly Gly Ser Thr Asn Tyr Asn Ser Ala Leu Met
 50                  55                  60

Ser Arg Leu Ser Ile Ser Lys Asp Asn Ser Arg Ser Gln Val Phe Leu
 65                  70                  75                  80

Arg Met Asn Ser Leu Gln Thr Asp Asp Thr Ala Met Tyr Tyr Cys Ala
                 85                  90                  95

Arg Ala Tyr Gly Asn Tyr Trp Tyr Ile Asp Val Trp Gly Ala Gly Thr
            100                 105                 110

Thr Val Thr Val Ser Ser
            115

<210> SEQ ID NO 5
<211> LENGTH: 321
<212> TYPE: DNA
<213> ORGANISM: Mus musculus

<400> SEQUENCE: 5
gacattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gataaactat gcatttcatc gcttcactgg agtccctgat     180
cgtttcactg gcagtggata tgggacggat ttcattttca ccatcagcac tgtgcaggct     240
gaagacctgg cagtttattt ctgtcaccag gcttatagtt ctccgtacac gttcggaggg     300
gggaccaagc tggaaatgaa a                                               321

<210> SEQ ID NO 6
<211> LENGTH: 107
<212> TYPE: PRT
<213> ORGANISM: Mus musculus

<400> SEQUENCE: 6

Asp Ile Val Met Thr Gln Thr Pro Lys Phe Leu Leu Val Ser Ala Gly
  1               5                  10                  15

Asp Arg Val Thr Ile Thr Cys Lys Ala Ser Gln Ser Val Ser Asn Asp
             20                  25                  30

Val Ala Trp Tyr Gln Gln Lys Pro Gly Gln Ser Pro Lys Leu Leu Ile
         35                  40                  45

Asn Tyr Ala Phe His Arg Phe Thr Gly Val Pro Asp Arg Phe Thr Gly
     50                  55                  60

Ser Gly Tyr Gly Thr Asp Phe Ile Phe Thr Ile Ser Thr Val Gln Ala
 65                  70                  75                  80

Glu Asp Leu Ala Val Tyr Phe Cys His Gln Ala Tyr Ser Ser Pro Tyr
                 85                  90                  95

Thr Phe Gly Gly Gly Thr Lys Leu Glu Met Lys
            100                 105

<210> SEQ ID NO 7
<211> LENGTH: 342
<212> TYPE: DNA
<213> ORGANISM: Mus musculus

<400> SEQUENCE: 7
cagatccagt tggtgcagtc tggacctgag ctgaagaagc ctggagagac agtcaagatc      60
tcctgcaagg cttctgggta taccttcaca aactatggaa tgaactgggt gaagcaggct     120
```

```
ccaggaaagg gtttaaagtg gatgggctgg ataaacaata ataatggaga gccaacatat    180
gctgaagagt tcaagggacg gtttgccttc tctttggaaa cctctgccag cactgcctat    240
ttgcagatca acaacctcaa aaatgaggac acggctacat atttctgtgc aagagatgtt    300
atggactatt ggggtcaagg aacctcagtc accgtctcct ca                      342
```

<210> SEQ ID NO 8
<211> LENGTH: 114
<212> TYPE: PRT
<213> ORGANISM: Mus musculus

<400> SEQUENCE: 8

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Asn Asn Asn Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Val Met Asp Tyr Trp Gly Gln Gly Thr Ser Val Thr Val
            100                 105                 110

Ser Ser
```

<210> SEQ ID NO 9
<211> LENGTH: 330
<212> TYPE: DNA
<213> ORGANISM: Mus musculus

<400> SEQUENCE: 9

```
gacattgtgc tgacccaatc tccagcttct ttggctgtgt ctctagggca gagggccacc     60
atatcctgca gagccagtga aagtgttgat aattatggct atagttttat gcactggtac    120
cagcagaaac caggacagcc acccaaactc ctcatctatc gtgcatccaa cctagaatct    180
gggatccctg ccaggttcag tggcagtggg tctaggacag gcttcaccct caccattaat    240
cctgtggagg ctgatgatgt tgcaacctat tactgtcagc aaagtaaaga atatccgacg    300
ttcggtggag gcaccaagct ggaagtcaaa                                    330
```

<210> SEQ ID NO 10
<211> LENGTH: 110
<212> TYPE: PRT
<213> ORGANISM: Mus musculus

<400> SEQUENCE: 10

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Gln Leu Leu Ile Tyr Arg Ala Ser Asn Leu Glu Ser Gly Ile Pro Ala
    50                  55                  60
```

Arg Phe Ser Gly Ser Gly Ser Arg Thr Gly Phe Thr Leu Thr Ile Asn
 65                  70                  75                  80

Pro Val Glu Ala Asp Asp Val Ala Thr Tyr Tyr Cys Gln Gln Ser Lys
                 85                  90                  95

Glu Tyr Pro Thr Phe Gly Gly Gly Thr Lys Leu Glu Val Lys
            100                 105                 110

<210> SEQ ID NO 11
<211> LENGTH: 10
<212> TYPE: PRT
<213> ORGANISM: Mus musculus

<400> SEQUENCE: 11

Gly Phe Ser Leu Thr Ser Tyr Gly Val His
1               5                   10

<210> SEQ ID NO 12
<211> LENGTH: 16
<212> TYPE: PRT
<213> ORGANISM: Mus musculus

<400> SEQUENCE: 12

Val Ile Trp Ala Gly Gly Ser Thr Asn Tyr Asn Ser Ala Leu Met Ser
1               5                   10                  15

<210> SEQ ID NO 13
<211> LENGTH: 12
<212> TYPE: PRT
<213> ORGANISM: Mus musculus

<400> SEQUENCE: 13

Ala Arg Ala Tyr Gly Asn Tyr Trp Tyr Ile Asp Val
1               5                   10

<210> SEQ ID NO 14
<211> LENGTH: 11
<212> TYPE: PRT
<213> ORGANISM: Mus musculus

<400> SEQUENCE: 14

Lys Ala Ser Gln Ser Val Ser Asn Asp Val Ala
1               5                   10

<210> SEQ ID NO 15
<211> LENGTH: 7
<212> TYPE: PRT
<213> ORGANISM: Mus musculus

<400> SEQUENCE: 15

Tyr Ala Phe His Arg Phe Thr
1               5

<210> SEQ ID NO 16
<211> LENGTH: 9
<212> TYPE: PRT
<213> ORGANISM: Mus musculus

<400> SEQUENCE: 16

His Gln Ala Tyr Ser Ser Pro Tyr Thr
1               5

<210> SEQ ID NO 17
<211> LENGTH: 10
<212> TYPE: PRT

```
<213> ORGANISM: Mus musculus

<400> SEQUENCE: 17

Gly Tyr Thr Phe Thr Asn Tyr Gly Met Asn
1               5                   10

<210> SEQ ID NO 18
<211> LENGTH: 17
<212> TYPE: PRT
<213> ORGANISM: Mus musculus

<400> SEQUENCE: 18

Trp Ile Asn Asn Asn Gly Glu Pro Thr Tyr Ala Glu Glu Phe Lys
1               5                   10                  15

Gly

<210> SEQ ID NO 19
<211> LENGTH: 7
<212> TYPE: PRT
<213> ORGANISM: Mus musculus

<400> SEQUENCE: 19

Ala Arg Asp Val Met Asp Tyr
1               5

<210> SEQ ID NO 20
<211> LENGTH: 15
<212> TYPE: PRT
<213> ORGANISM: Mus musculus

<400> SEQUENCE: 20

Arg Ala Ser Glu Ser Val Asp Asn Tyr Gly Tyr Ser Phe Met His
1               5                   10                  15

<210> SEQ ID NO 21
<211> LENGTH: 7
<212> TYPE: PRT
<213> ORGANISM: Mus musculus

<400> SEQUENCE: 21

Arg Ala Ser Asn Leu Glu Ser
1               5

<210> SEQ ID NO 22
<211> LENGTH: 8
<212> TYPE: PRT
<213> ORGANISM: Mus musculus

<400> SEQUENCE: 22

Gln Gln Ser Lys Glu Tyr Pro Thr
1               5

<210> SEQ ID NO 23
<211> LENGTH: 354
<212> TYPE: DNA
<213> ORGANISM: Artificial Sequence
<220> FEATURE:
<223> OTHER INFORMATION: 317-4B6 cDNA-Vh

<400> SEQUENCE: 23
caggtgcagc tgcaggagtc gggaccagga ctggtgaagc cttcggagac cctgtccctc      60
acctgcactg tctctgggtt ttcattaacc agctatggtg tacactggat ccggcagccc    120
ccagggaagg gactggagtg gatcgggggtc atatacgccg atggaagcac aaattataat    180
```

```
cctcccctca agagtcgagt gaccatatca aaagacacct ccaagaacca ggtttccctg      240
aagctgagct ctgtgaccgc tgcggacacg gccgtgtatt actgtgcgag agcctatggt      300
aactactggt acatcgatgt ctggggccaa gggaccacgg tcaccgtctc ctca            354
```

<210> SEQ ID NO 24
<211> LENGTH: 118
<212> TYPE: PRT
<213> ORGANISM: Artificial Sequence
<220> FEATURE:
<223> OTHER INFORMATION: 317-4B6 pro-Vh

<400> SEQUENCE: 24

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Asp Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

<210> SEQ ID NO 25
<211> LENGTH: 321
<212> TYPE: DNA
<213> ORGANISM: Artificial Sequence
<220> FEATURE:
<223> OTHER INFORMATION: 317-4B6 cDNA-Vk

<400> SEQUENCE: 25

```
gacatcgtga tgacccagtc tccagactcc ctggctgtgt ctctgggcga gagggccacc      60
atcaactgca gtccagcga gagtgtgagt aatgatgtag cttggtacca gcagaaacca      120
ggacagcctc ctaagctgct cattaactat gcatttcatc gcttcactgg ggtccctgac      180
cgattcagtg gcagcgggta tgggacagat ttcactctca ccatcagcag cctgcaggct      240
gaagatgtgg cagttttatta ctgtcaccag gcttatagtt ctccgtacac gtttggccag      300
gggaccaagc tggagatcaa a                                                 321
```

<210> SEQ ID NO 26
<211> LENGTH: 107
<212> TYPE: PRT
<213> ORGANISM: Artificial Sequence
<220> FEATURE:
<223> OTHER INFORMATION: 317-4B6 pro-Vk

<400> SEQUENCE: 26

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30
```

```
Val Ala Trp Tyr Gln Gln Lys Pro Gly Gln Pro Pro Lys Leu Leu Ile
         35                  40                  45

Asn Tyr Ala Phe His Arg Phe Thr Gly Val Pro Asp Arg Phe Ser Gly
 50                  55                  60

Ser Gly Tyr Gly Thr Asp Phe Thr Leu Thr Ile Ser Ser Leu Gln Ala
 65                  70                  75                  80

Glu Asp Val Ala Val Tyr Tyr Cys His Gln Ala Tyr Ser Ser Pro Tyr
                 85                  90                  95

Thr Phe Gly Gln Gly Thr Lys Leu Glu Ile Lys
            100                 105
```

<210> SEQ ID NO 27
<211> LENGTH: 342
<212> TYPE: DNA
<213> ORGANISM: Artificial Sequence
<220> FEATURE:
<223> OTHER INFORMATION: 326-4A3 cDNA-Vh

<400> SEQUENCE: 27

```
caggtgcagc tggtgcagag cggcagcgag ctgaagaagc ccggcgccag cgtgaaggtg      60
agctgcaagg ccagcggcta caccttcacc aactacggca tgaactgggt gagacaggcc     120
cccggccagg gcctgaagtg gatgggctgg atcaacaaca acaacgccga gcccacctac     180
gcccaggact tcagaggcag attcgtgttc agcctggaca ccagcgccag caccgcctac     240
ctgcagatca gcagcctgaa gaccgaggac accgccgtgt actactgcgc cagagacgtg     300
atggactact ggggccaggg caccctggtg accgtgagca gc                       342
```

<210> SEQ ID NO 28
<211> LENGTH: 114
<212> TYPE: PRT
<213> ORGANISM: Artificial Sequence
<220> FEATURE:
<223> OTHER INFORMATION: 326-4A3 pro-Vh

<400> SEQUENCE: 28

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
             20                  25                  30

Gly Met Asn Trp Val Arg Gln Ala Pro Gly Gln Gly Leu Lys Trp Met
         35                  40                  45

Gly Trp Ile Asn Asn Asn Asn Ala Glu Pro Thr Tyr Ala Gln Asp Phe
 50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Leu Val Thr Val
            100                 105                 110

Ser Ser
```

<210> SEQ ID NO 29
<211> LENGTH: 330
<212> TYPE: DNA
<213> ORGANISM: Artificial Sequence
<220> FEATURE:
<223> OTHER INFORMATION: 326-4A3 cDNA-Vk

<400> SEQUENCE: 29

```
gacattgtgc tgacccagtc tccagcctcc ttggccgtgt ctccaggaca gagggccacc    60
atcacctgca gagccagtga aagtgttgat aattatggct atagttttat gcactggtat   120
cagcagaaac caggacaacc tcctaaactc ctgatttacc gtgcatccaa cctagaatct   180
ggggtcccag ccaggttcag cggcagtggg tctgggaccg atttcaccct cacaattaat   240
cctgtggaag ctgaggatac tgcaaattat tactgtcagc aaagtaaaga atatccgacg   300
ttcggcggag ggaccaaggt ggagatcaaa                                    330
```

<210> SEQ ID NO 30
<211> LENGTH: 110
<212> TYPE: PRT
<213> ORGANISM: Artificial Sequence
<220> FEATURE:
<223> OTHER INFORMATION: 326-4A3 pro-Vk

<400> SEQUENCE: 30

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110
```

<210> SEQ ID NO 31
<211> LENGTH: 10
<212> TYPE: PRT
<213> ORGANISM: Mus musculus

<400> SEQUENCE: 31

```
Gly Phe Ser Leu Thr Ser Tyr Gly Val His
1               5                   10
```

<210> SEQ ID NO 32
<211> LENGTH: 16
<212> TYPE: PRT
<213> ORGANISM: Artificial Sequence
<220> FEATURE:
<223> OTHER INFORMATION: 317-4B6 H-CDR2 or CDR-H2

<400> SEQUENCE: 32

```
Val Ile Tyr Ala Asp Gly Ser Thr Asn Tyr Asn Pro Ser Leu Lys Ser
1               5                   10                  15
```

<210> SEQ ID NO 33
<211> LENGTH: 12
<212> TYPE: PRT
<213> ORGANISM: Mus musculus

```
<400> SEQUENCE: 33

Ala Arg Ala Tyr Gly Asn Tyr Trp Tyr Ile Asp Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: 317-4B6 L-CDR1 or CDR-L1

<400> SEQUENCE: 34

Lys Ser Ser Glu Ser Val Ser Asn Asp Val Ala
1               5                   10

<210> SEQ ID NO 35
<211> LENGTH: 7
<212> TYPE: PRT
<213> ORGANISM: Mus musculus

<400> SEQUENCE: 35

Tyr Ala Phe His Arg Phe Thr
1               5

<210> SEQ ID NO 36
<211> LENGTH: 9
<212> TYPE: PRT
<213> ORGANISM: Mus musculus

<400> SEQUENCE: 36

His Gln Ala Tyr Ser Ser Pro Tyr Thr
1               5

<210> SEQ ID NO 37
<211> LENGTH: 10
<212> TYPE: PRT
<213> ORGANISM: Mus musculus

<400> SEQUENCE: 37

Gly Tyr Thr Phe Thr Asn Tyr Gly Met Asn
1               5                   10

<210> SEQ ID NO 38
<211> LENGTH: 17
<212> TYPE: PRT
<213> ORGANISM: Artificial Sequence
<220> FEATURE:
<223> OTHER INFORMATION: 326-4A3 H-CDR2 or CDR-H2

<400> SEQUENCE: 38

Trp Ile Asn Asn Asn Asn Ala Glu Pro Thr Tyr Ala Gln Asp Phe Arg
1               5                   10                  15

Gly

<210> SEQ ID NO 39
<211> LENGTH: 7
<212> TYPE: PRT
<213> ORGANISM: Mus musculus

<400> SEQUENCE: 39

Ala Arg Asp Val Met Asp Tyr
1               5
```

```
<210> SEQ ID NO 40
<211> LENGTH: 15
<212> TYPE: PRT
<213> ORGANISM: Mus musculus

<400> SEQUENCE: 40

Arg Ala Ser Glu Ser Val Asp Asn Tyr Gly Tyr Ser Phe Met His
1               5                   10                  15

<210> SEQ ID NO 41
<211> LENGTH: 7
<212> TYPE: PRT
<213> ORGANISM: Mus musculus

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Mus musculus

<400> SEQUENCE: 42

Gln Gln Ser Lys Glu Tyr Pro Thr
1               5

<210> SEQ ID NO 43
<211> LENGTH: 118
<212> TYPE: PRT
<213> ORGANISM: Artificial Sequence
<220> FEATURE:
<223> OTHER INFORMATION: 317-4B2 pro-Vh

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: 317-4B2 pro-Vk

<400> SEQUENCE: 44

Asp Ile Val Met Thr Gln Ser Pro Asp Ser Leu Ala Val Ser Leu Gly
1               5                   10                  15
```

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 45
<211> LENGTH: 118
<212> TYPE: PRT
<213> ORGANISM: Artificial Sequence
<220> FEATURE:
<223> OTHER INFORMATION: 317-4B5 pro-Vh

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: 317-4B5 pro-Vk

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 47
<211> LENGTH: 354
<212> TYPE: DNA
<213> ORGANISM: Artificial Sequence
<220> FEATURE:
<223> OTHER INFORMATION: 317-1 cDNA-Vh

<400> SEQUENCE: 47
caggtgcagc tgcaggagtc gggaccagga ctggtgaagc cttcggagac cctgtccctc      60
acctgcactg tctctgggtt ttcattaacc agctatggtg tacactggat ccggcagccc     120
ccagggaagg gactggagtg gctgggggtc atatgggccg gtggaagcac aaattataat     180
ccctccctca agagtcgact gaccatatca aagacaact ccaagagcca ggtttccctg      240
aagatgagct ctgtgaccgc tgcggacacg gccgtgtatt actgtgcgag agcctatggt     300
aactactggt acatcgatgt ctggggccaa gggaccacgg tcaccgtctc ctca           354

<210> SEQ ID NO 48
<211> LENGTH: 118
<212> TYPE: PRT
<213> ORGANISM: Artificial Sequence
<220> FEATURE:
<223> OTHER INFORMATION: 317-1 pro-Vh

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Pro Ser Leu Lys
    50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 49
<211> LENGTH: 321
<212> TYPE: DNA
<213> ORGANISM: Artificial Sequence
<220> FEATURE:
<223> OTHER INFORMATION: 317-1 cDNA-Vk

<400> SEQUENCE: 49
gacatcgtga tgacccagtc tccagactcc ctggctgtgt ctctgggcga gagggccacc      60
atcaactgca aggccagcca gagtgtgagt aatgatgtag cttggtacca gcagaaacca     120
ggacagcctc ctaagctgct cattaactat gcatttcatc gcttcactgg ggtccctgac     180
cgattcagtg gcagcgggta tgggacagat ttcactctca ccatcagcag cctgcaggct     240

```
gaagatgtgg cagtttatta ctgtcaccag gcttatagtt ctccgtacac gtttggcggg    300
gggaccaagc tggagatcaa a                                              321
```

<210> SEQ ID NO 50
<211> LENGTH: 107
<212> TYPE: PRT
<213> ORGANISM: Artificial Sequence
<220> FEATURE:
<223> OTHER INFORMATION: 317-1 pro-Vk

<400> SEQUENCE: 50

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gly Gly Thr Lys Leu Glu Ile Lys
            100                 105
```

<210> SEQ ID NO 51
<211> LENGTH: 114
<212> TYPE: PRT
<213> ORGANISM: Artificial Sequence
<220> FEATURE:
<223> OTHER INFORMATION: 326-3B1 pro-Vh

<400> SEQUENCE: 51

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser
```

<210> SEQ ID NO 52
<211> LENGTH: 110
<212> TYPE: PRT
<213> ORGANISM: Artificial Sequence
<220> FEATURE:
<223> OTHER INFORMATION: 326-3B1 pro-Vk

<400> SEQUENCE: 52

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 53
<211> LENGTH: 114
<212> TYPE: PRT
<213> ORGANISM: Artificial Sequence
<220> FEATURE:
<223> OTHER INFORMATION: 326-3G1 pro-Vh

<400> SEQUENCE: 53

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 54
<211> LENGTH: 110
<212> TYPE: PRT
<213> ORGANISM: Artificial Sequence
<220> FEATURE:
<223> OTHER INFORMATION: 326-3G1 pro-Vk

<400> SEQUENCE: 54

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

```
Arg Phe Ser Gly Ser Gly Ser Arg Thr Asp Phe Thr Leu Thr Ile Asn
 65                  70                  75                  80

Pro Val Glu Ala Asn Asp Thr Ala Asn Tyr Tyr Cys Gln Gln Ser Lys
                 85                  90                  95

Glu Tyr Pro Thr Phe Gly Gly Gly Thr Lys Val Glu Ile Lys
            100                 105                 110

<210> SEQ ID NO 55
<211> LENGTH: 342
<212> TYPE: DNA
<213> ORGANISM: Artificial Sequence
<220> FEATURE:
<223> OTHER INFORMATION: 326-1 cDNA-Vh

<400> SEQUENCE: 55
caggtgcagc tggtgcagag cggcagcgag ctgaagaagc ccggcgccag cgtgaaggtg     60
agctgcaagg ccagcggcta caccttcacc aactacggca tgaactgggt gagacaggcc    120
cccggccagg gcctggagtg gatgggctgg atcaacaaca acaacggcga gcccacctac    180
gcccagggct tcagaggcag attcgtgttc agcctggaca ccagcgccag caccgcctac    240
ctgcagatca gcagcctgaa gaccgaggac accgccgtgt acttctgcgc cagagacgtg    300
atggactact ggggccaggg caccaccgtg accgtgagca gc                       342

<210> SEQ ID NO 56
<211> LENGTH: 114
<212> TYPE: PRT
<213> ORGANISM: Artificial Sequence
<220> FEATURE:
<223> OTHER INFORMATION: 326-1 pro-Vh

<400> SEQUENCE: 56

Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Thr Phe Thr Asn Tyr
                 20                  25                  30

Gly Met Asn Trp Val Arg Gln Ala Pro Gly Gln Gly Leu Glu Trp Met
             35                  40                  45

Gly Trp Ile Asn Asn Asn Asn Gly Glu Pro Thr Tyr Ala Gln Gly Phe
 50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Phe Cys
                 85                  90                  95

Ala Arg Asp Val Met Asp Tyr Trp Gly Gln Gly Thr Thr Val Thr Val
            100                 105                 110

Ser Ser

<210> SEQ ID NO 57
<211> LENGTH: 330
<212> TYPE: DNA
<213> ORGANISM: Artificial Sequence
<220> FEATURE:
<223> OTHER INFORMATION: 326-1 cDNA-Vk

<400> SEQUENCE: 57
gacattgtgc tgacccagtc tccagcctcc ttggccgtgt ctccaggaca gagggccacc     60
atcacctgca gagccagtga aagtgttgat aattatggca tagttttat gcactggtat    120 cagcagaaac caggacaacc tcctaaactc ctgatttacc gtgcatccaa cctagaatct    180
```

```
ggggtcccag ccaggttcag cggcagtggg tctaggaccg atttcaccct cacaattaat    240
cctgtggaag ctaatgatac tgcaaattat tactgtcagc aaagtaaaga atatccgacg    300
ttcggcggag ggaccaaggt ggagatcaaa                                     330
```

<210> SEQ ID NO 58
<211> LENGTH: 110
<212> TYPE: PRT
<213> ORGANISM: Artificial Sequence
<220> FEATURE:
<223> OTHER INFORMATION: 326-1 pro-Vk

<400> SEQUENCE: 58

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110
```

<210> SEQ ID NO 59
<211> LENGTH: 16
<212> TYPE: PRT
<213> ORGANISM: Artificial Sequence
<220> FEATURE:
<223> OTHER INFORMATION: 317-1 H-CDR2 or CDR-H2

<400> SEQUENCE: 59

```
Val Ile Trp Ala Gly Gly Ser Thr Asn Tyr Asn Pro Ser Leu Lys Ser
1               5                   10                  15
```

<210> SEQ ID NO 60
<211> LENGTH: 16
<212> TYPE: PRT
<213> ORGANISM: Artificial Sequence
<220> FEATURE:
<223> OTHER INFORMATION: 317-4B2 H-CDR2 or CDR-H2

<400> SEQUENCE: 60

```
Val Ile Tyr Ala Gly Gly Ser Thr Asn Tyr Asn Pro Ser Leu Lys Ser
1               5                   10                  15
```

<210> SEQ ID NO 61
<211> LENGTH: 11
<212> TYPE: PRT
<213> ORGANISM: Artificial Sequence
<220> FEATURE:
<223> OTHER INFORMATION: 317-4B2 L-CDR1 or CDR-L1

<400> SEQUENCE: 61

```
Lys Ser Ser Glu Ser Val Ser Asn Asp Val Ala
1               5                   10
```

<210> SEQ ID NO 62

```
<211> LENGTH: 17
<212> TYPE: PRT
<213> ORGANISM: Artificial Sequence
<220> FEATURE:
<223> OTHER INFORMATION: 326-1 H-CDR2 or CDR-H2

<400> SEQUENCE: 62

Trp Ile Asn Asn Asn Asn Gly Glu Pro Thr Tyr Ala Gln Gly Phe Arg
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: 326-3G1 H-CDR2 or CDR-H2

<400> SEQUENCE: 63

Trp Ile Asn Asn Asn Asn Gly Glu Pro Thr Tyr Ala Gln Asp Phe Arg
1               5                   10                  15

Gly

<210> SEQ ID NO 64
<211> LENGTH: 118
<212> TYPE: PRT
<213> ORGANISM: Artificial Sequence
<220> FEATURE:
<223> OTHER INFORMATION: 317-3A1 pro-Vh

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: 317-3C1 pro-Vh

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30
```

Gly Val His Trp Ile Arg Gln Pro Gly Lys Gly Leu Glu Trp Leu
            35                  40                  45

Gly Val Ile Trp Ala Gly Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 66
<211> LENGTH: 118
<212> TYPE: PRT
<213> ORGANISM: Artificial Sequence
<220> FEATURE:
<223> OTHER INFORMATION: 317-3E1 pro-Vh

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
            35                  40                  45

Gly Val Ile Trp Ala Gly Gly Ser Thr Asn Tyr Asn Pro Ser Leu Lys
        50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 67
<211> LENGTH: 118
<212> TYPE: PRT
<213> ORGANISM: Artificial Sequence
<220> FEATURE:
<223> OTHER INFORMATION: 317-3F1 pro-Vh

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
            35                  40                  45

Gly Val Ile Trp Ala Gly Gly Ser Thr Asn Tyr Asn Pro Ser Leu Lys
        50                  55                  60

Ser Arg Val Thr Ile Ser Val Asp Thr Ser Lys Asn Gln Val Ser Leu
65                  70                  75                  80

```
Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 68
<211> LENGTH: 118
<212> TYPE: PRT
<213> ORGANISM: Artificial Sequence
<220> FEATURE:
<223> OTHER INFORMATION: 317-3G1 pro-Vh

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: 317-3H1 pro-Vh

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

-continued

```
<210> SEQ ID NO 70
<211> LENGTH: 118
<212> TYPE: PRT
<213> ORGANISM: Artificial Sequence
<220> FEATURE:
<223> OTHER INFORMATION: 317-3I1 pro-Vh

<400> SEQUENCE: 70
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

```
<210> SEQ ID NO 71
<211> LENGTH: 118
<212> TYPE: PRT
<213> ORGANISM: Artificial Sequence
<220> FEATURE:
<223> OTHER INFORMATION: 317-4B1 pro-Vh

<400> SEQUENCE: 71
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

```
<210> SEQ ID NO 72
<211> LENGTH: 118
<212> TYPE: PRT
<213> ORGANISM: Artificial Sequence
<220> FEATURE:
<223> OTHER INFORMATION: 317-4B3 pro-Vh

<400> SEQUENCE: 72
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
            35                  40                  45

Gly Val Ile Asn Ala Gly Gly Ser Thr Asn Tyr Asn Pro Ser Leu Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 73
<211> LENGTH: 118
<212> TYPE: PRT
<213> ORGANISM: Artificial Sequence
<220> FEATURE:
<223> OTHER INFORMATION: 317-4B4 pro-Vh

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
            35                  40                  45

Gly Val Ile Trp Ala Gly Gly Ser Thr Asn Tyr Asn Pro Ser Leu Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Pro Tyr Ile Asp Val Trp Gly Gln Gly Thr
                100                 105                 110

Thr Val Thr Val Ser Ser
            115

<210> SEQ ID NO 74
<211> LENGTH: 107
<212> TYPE: PRT
<213> ORGANISM: Artificial Sequence
<220> FEATURE:
<223> OTHER INFORMATION: 317-4A2 pro-Vk

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
            20                  25                  30

Val Ala Trp Tyr Gln Gln Lys Pro Gly Gln Pro Pro Lys Leu Leu Ile
            35                  40                  45

Asn Tyr Ala Phe His Arg Phe Thr Gly Val Pro Asp Arg Phe Ser Gly
 50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 75
<211> LENGTH: 114
<212> TYPE: PRT
<213> ORGANISM: Artificial Sequence
<220> FEATURE:
<223> OTHER INFORMATION: 326-3A1 pro-Vh

<400> SEQUENCE: 75

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
                100                 105                 110

Ser Ser

<210> SEQ ID NO 76
<211> LENGTH: 114
<212> TYPE: PRT
<213> ORGANISM: Artificial Sequence
<220> FEATURE:
<223> OTHER INFORMATION: 326-3C1 pro-Vh

<400> SEQUENCE: 76

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Val Thr Val
                100                 105                 110

Ser Ser

<210> SEQ ID NO 77
<211> LENGTH: 114

<212> TYPE: PRT
<213> ORGANISM: Artificial Sequence
<220> FEATURE:
<223> OTHER INFORMATION: 326-3D1 pro-Vh

<400> SEQUENCE: 77

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 78
<211> LENGTH: 114
<212> TYPE: PRT
<213> ORGANISM: Artificial Sequence
<220> FEATURE:
<223> OTHER INFORMATION: 326-3E1 pro-Vh

<400> SEQUENCE: 78

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser

<210> SEQ ID NO 79
<211> LENGTH: 114
<212> TYPE: PRT
<213> ORGANISM: Artificial Sequence
<220> FEATURE:
<223> OTHER INFORMATION: 326-3F1 pro-Vh

<400> SEQUENCE: 79

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Asn Asn Gly Glu Pro Thr Tyr Ala Gln Gly Phe
50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
            85                  90                  95

Ala Arg Asp Val Met Asp Tyr Trp Gly Gln Gly Thr Thr Val Thr Val
                100                 105                 110

Ser Ser

<210> SEQ ID NO 80
<211> LENGTH: 114
<212> TYPE: PRT
<213> ORGANISM: Artificial Sequence
<220> FEATURE:
<223> OTHER INFORMATION: 326-3B N55D pro-Vh

<400> SEQUENCE: 80

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Asn Asn Asp Gly Glu Pro Thr Tyr Ala Gln Asp Phe
50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
            85                  90                  95

Ala Arg Asp Val Met Asp Tyr Trp Gly Gln Gly Thr Leu Val Thr Val
                100                 105                 110

Ser Ser

<210> SEQ ID NO 81
<211> LENGTH: 110
<212> TYPE: PRT
<213> ORGANISM: Artificial Sequence
<220> FEATURE:
<223> OTHER INFORMATION: 326-4A1 pro-Vk

<400> SEQUENCE: 81

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
                20                  25                  30

Gly Tyr Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Val Pro Ala
        50                  55                  60

Arg Phe Ser Gly Ser Gly Ser Arg Thr Asp Phe Thr Leu Thr Ile Asn
65                  70                  75                  80

Pro Val Glu Ala Glu Asp Thr Ala Asn Tyr Tyr Cys Gln Gln Ser Lys
            85                  90                  95

```
Glu Tyr Pro Thr Phe Gly Gly Gly Thr Lys Val Glu Ile Lys
                100                 105                 110

<210> SEQ ID NO 82
<211> LENGTH: 110
<212> TYPE: PRT
<213> ORGANISM: Artificial Sequence
<220> FEATURE:
<223> OTHER INFORMATION: 326-4A2 pro-Vk

<400> SEQUENCE: 82

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
                100                 105                 110

<210> SEQ ID NO 83
<211> LENGTH: 327
<212> TYPE: PRT
<213> ORGANISM: Artificial Sequence
<220> FEATURE:
<223> OTHER INFORMATION: huIgG4mt1 pro

<400> SEQUENCE: 83

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 84
<211> LENGTH: 327
<212> TYPE: PRT
<213> ORGANISM: Artificial Sequence
<220> FEATURE:
<223> OTHER INFORMATION: huIgG4mt2 pro

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 85
<211> LENGTH: 327
<212> TYPE: PRT
<213> ORGANISM: Artificial Sequence
<220> FEATURE:
<223> OTHER INFORMATION: huIgG4mt6 pro

<400> SEQUENCE: 85

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 86
<211> LENGTH: 327
<212> TYPE: PRT
<213> ORGANISM: Artificial Sequence
<220> FEATURE:
<223> OTHER INFORMATION: huIgG4mt8 pro

<400> SEQUENCE: 86

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Pro Val Ala Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Thr Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 87
<211> LENGTH: 327
<212> TYPE: PRT
<213> ORGANISM: Artificial Sequence
<220> FEATURE:
<223> OTHER INFORMATION: huIgG4mt9 pro

<400> SEQUENCE: 87

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300
```

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 88
<211> LENGTH: 327
<212> TYPE: PRT
<213> ORGANISM: Artificial Sequence
<220> FEATURE:
<223> OTHER INFORMATION: huIgG4mt10 pro

<400> SEQUENCE: 88

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 89
<211> LENGTH: 367
<212> TYPE: PRT
<213> ORGANISM: Artificial Sequence
<220> FEATURE:
<223> OTHER INFORMATION: OS8 pro

<400> SEQUENCE: 89

```
Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
            35                  40                  45

Thr Arg Tyr Thr Met His Trp Val Lys Gln Arg Pro Gly Gln Gly Leu
 50                  55                  60

Glu Trp Ile Gly Tyr Ile Asn Pro Ser Arg Gly Tyr Thr Asn Tyr Asn
 65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Cys Leu Asp Tyr Trp
            115                 120                 125

Gly Gln Gly Thr Thr Leu Thr Val Ser Ser Gly Gly Gly Gly Ser Gly
        130                 135                 140

Gly Gly Gly Ser Gly Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

Glu Ile Asn Ser Ser Val Val Pro Val Leu Gln Lys Val Asn Ser Thr
            260                 265                 270

Thr Thr Lys Pro Val Leu Arg Thr Pro Ser Pro Val His Pro Thr Gly
        275                 280                 285

Thr Ser Gln Pro Gln Arg Pro Glu Asp Cys Arg Pro Arg Gly Ser Val
    290                 295                 300

Lys Gly Thr Gly Leu Asp Phe Ala Cys Asp Ile Tyr Ile Trp Ala Pro
305                 310                 315                 320

Leu Ala Gly Ile Cys Val Ala Leu Leu Leu Ser Leu Ile Ile Thr Leu
                325                 330                 335

Ile Cys Tyr His Arg Ser Arg Lys Arg Val Cys Lys Cys Pro Arg Pro
            340                 345                 350

Leu Val Arg Gln Glu Gly Lys Pro Arg Pro Ser Glu Lys Ile Val
        355                 360                 365
```

<210> SEQ ID NO 90
<211> LENGTH: 304
<212> TYPE: PRT
<213> ORGANISM: Artificial Sequence
<220> FEATURE:
<223> OTHER INFORMATION: P3Z pro

<400> SEQUENCE: 90

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Val Lys Phe Ser Arg Ser Ala Asp Ala Pro Ala Tyr Gln Gln Gly Gln
            195                 200                 205

Asn Gln Leu Tyr Asn Glu Leu Asn Leu Gly Arg Arg Glu Glu Tyr Asp
            210                 215                 220

Val Leu Asp Lys Arg Arg Gly Arg Asp Pro Glu Met Gly Gly Lys Pro
225                 230                 235                 240

Gln Arg Arg Lys Asn Pro Gln Glu Gly Leu Tyr Asn Glu Leu Gln Lys
                245                 250                 255

Asp Lys Met Ala Glu Ala Tyr Ser Glu Ile Gly Met Lys Gly Glu Arg
            260                 265                 270

Arg Arg Gly Lys Gly His Asp Gly Leu Tyr Gln Gly Leu Ser Thr Ala
            275                 280                 285

Thr Lys Asp Thr Tyr Asp Ala Leu His Met Gln Ala Leu Pro Pro Arg
290                 295                 300
```